US006228835B1

(12) United States Patent
Guo et al.

(10) Patent No.: US 6,228,835 B1
(45) Date of Patent: May 8, 2001

(54) DECORIN BINDING PROTEIN COMPOSITIONS

(75) Inventors: Betty Guo; Magnus Höök, both of Houston, TX (US)

(73) Assignee: The Texas A & M Unversity System, College Station, TX (US)

( * ) Notice: Subject to any disclaimer, the term of this patent is extended or adjusted under 35 U.S.C. 154(b) by 0 days.

(21) Appl. No.: 09/221,938

(22) Filed: Dec. 28, 1998

Related U.S. Application Data

(60) Division of application No. 08/589,711, filed on Jan. 22, 1996, now Pat. No. 5,853,987, which is a continuation-in-part of application No. 08/427,023, filed on Apr. 24, 1995, now abandoned.

(51) Int. Cl.$^7$ .............................. A61K 38/16; C07K 14/20

(52) U.S. Cl. .............................. 514/2; 530/350; 530/806; 530/825

(58) Field of Search ................................ 530/350, 388.1, 530/806, 825; 424/85.8; 514/2

(56) References Cited

U.S. PATENT DOCUMENTS

| 5,460,955 | 10/1995 | Mosher et al. | 435/69.7 |
|---|---|---|---|
| 5,853,987 | 12/1998 | Guo et al. | 435/6 |

FOREIGN PATENT DOCUMENTS

| WO 90/004411 | 5/1990 | (WO) | A61K/39/02 |
|---|---|---|---|
| WO 92/00055 | 1/1992 | (WO) | C12N/15/31 |
| WO 95/04145 | 2/1995 | (WO) | C12N/15/31 |
| WO96/34106 | 10/1996 | (WO) | C12N/15/30 |
| WO 97/27301 | 7/1997 | (WO) | C15N/15/30 |
| WO 98/06850 | 2/1998 | (WO) . | |

OTHER PUBLICATIONS

Barbour. A.G., "Isolation and Cultivation of Lyme Disease Spirochetes," *Yale J. Biol. Med.*, 57:521–525, 1984.
de Silva, et al.,"*Borrelia Burgdorferi* OspA is an Arthropod–Specific Transmission–Blocking Lyme Disease Vaccine," *J. Exp. Med.*, 183:271–275, 1996.
Genovese, et al., "Construction of DNA Sequences Complementary to Rat $\alpha_1$ and $\alpha_2$ Collagen mRNA and Their Use in Studying the Regulation of Type I Collagen Synthesis by 1,25–Dihydroxyvitamin D$^{+}$," *Biochemistry*, 23:6210–6216, 1984.
Jauris–Heipke, et al., "Genetic Heterogeneity of the Genes Coding for the Outer Surface Protein C(OspC) and the Flagellin of *Borrelia Burgdorferi*," *Med. Microbial. Immunol. (Berl)*, 182(1):37–50, 1993.
Oldberg, et al., "A Collagen–Binding 59–kd Protein (Fibromodulin) is Structurally Related to the Small Interstitial Proteoglycans PG–S1 and PG–S2 (Decorin)," *The EMBO Journal*, 6(9):2601–2604, 1989.

Schönherr, et al., "Interaction of Biglycan with Type I Collagen," *J. Biol. Chem.*, 270(6):2776–2783, 1995.
Schönherr et al., "Decorin–Type I Collagen Interaction," *J. Biol. Chem.*, 270(15):8877–8883, 1995.
Takeuchi, et al., "Bone Matrix Decorin Binds Transforming Growth Factor–β and Enhances its Bioactivity," *J. Biol. Chem.*, 269:32634–32638, 1994.
Guo, B., Höök, M., Norris, S. J. and Howell, J. *Borrelia burgdorferi*: Adherence of Two Outer Surface Proteins to the Proteoglycan, Decorin, *Meeting of the Texas Branch of The American Society for Microbiology*, Austin, Texas, Abstract No. 15, Nov. 11–13, 1993.
Alon, R., E.A. Bayer and M. Wilchek, Biotin–Containing Protein as a Cause of False Positive Clones in Gene Probing with Streptavidin/Biotin, *BioTechniques*, 14(2):209–210, 1993.
Isberg, Ralph R., Discrimination Between Intracellular Uptake and Surface Adhesion of Bacterial Pathogens, *Science*, 252:934–938, May 17, 1991.
"Immunological Screening of Expression Libraries", *Screening Expression Libraries with Antibodies and Oligonucleotides*, pp 12.16–12.14, 1989.
Kantor, Fred S., "Disarming Lyme Disease", *Scientific American*, pp. 34–39, Sep., 1994.
Kreis, Thomas, Vale, Ronald, "Guidebook to the Extracellular Matrix and Adhesion Proteins", *Decorin (DCN)*, pp. 48–49 Oct 7, 1993.
Langermann, Solomon, Palaszynski, Susan, Sadziene, Ariadna, Stover, C. Kendall, Koenig, Scott, Systemic and Mucosal Immunity Induced by BCG Vector Expressing Outer–Surface Protein A of *Borrelia burgdorferi*, *Nature*, 372:552–555, Dec. 8, 1994.
Philipp, Mario T., Johnson Barbara J.B., "Animal Models of Lyme Disease: Pathogensis and Immunoprophylaxis", *Trends in Microbiology*, 2(11):431–437, Nov., 1994.

(List continued on next page.)

Primary Examiner—Stephanie W. Zitomer
(74) Attorney, Agent, or Firm—Williams, Morgan and Amerson

(57) ABSTRACT

Disclosed are the dbp gene and dbp-derived nucleic acid segments from *Borrelia burgdorferi*, the etiological agent of Lyme disease, and DNA segments encoding dbp from related borrelias. Also disclosed are decorin binding protein compositions and methods of use. The DBP protein and antigenic epitopes derived therefrom are contemplated for use in the treatment of pathological Borrelia infections, and in particular, for use in the prevention of bacterial adhesion to decorin. DNA segments encoding these proteins and anti-(decorin binding protein) antibodies will also be of use in various screening, diagnostic and therapeutic applications including active and passive immunization and methods for the prevention of Borrelia colonization in an animal. These DNA segments and the peptides derived therefrom are contemplated for use in the preparation of vaccines and, also, for use as carrier proteins in vaccine formulations, and in the formulation of compositions for use in the prevention of Lyme disease.

24 Claims, 14 Drawing Sheets

OTHER PUBLICATIONS

Sharon, Nathan, Lis, Halina, "Carbohydrates in Cell Recognition", *Scientific American*, pp. 82–89, Jan., 1993.

Steere, Allen C., "Lyme Disease: A Growing Threat to Urban Populations", *Proc. Natl. Acad. Sci., USA*, 91:2378–2382, Mar., 1994.

Guo, B., Norris, S.J., Howell, J., Hook, M., Identification of Decorin Binding Proteins on the Outer Membrane Surface of *Borrelia burgdorferi, Abstr. Annu. Meet. Am. Soc. Microbiol.*, D–161, p. 124, May, 1994 (listed in C10).

Guo, B., Norris, S.J., Rosenberg, Lawrence C., Hook, M., Adherence of *Borrelia burgdorferi* to the Proteoglycan Decorin, *Infect. Immun.*, 63(9):3467–3472 (listed in C10), 1995.

Bidanset et al., "Binding of the Proteoglycan Decorin to Collagen Type VI," *J. Biol. Chem.* 267(8):5250–5256, Mar. 15, 1992.

Guo et al., "Evidence that the decorin binding protein of *Borrelia burgdorferi* is an adhesion," 96th General Meeting of the American Society for Microbiology, New Orleans, Louisiana, May 19–23, 1996, 248. ISSN: 1060–2011, XP 000618881, Abstract No. D–38.

Krumdieck et al., The proteoglycan decorin binds C1q and inhibits the activity of the C1 complex[1], *J. Immunol.*, 149(11):3695–3701, 1992.

Probert et al., "Immunization with the outer surface proteins of *Borrelia burgdorferi* provides limited cross–protection," *95th ASM General Meeting*, 144 ISSN 0067–2777, Abstract No. E–56, p. 290, May 21–25, 1995.

Yamaguchi et al., "Negative regulation of transforming growth factor–$\beta$ by the proteoglycan decorin," *Nature*, 346:281–284, Jul. 19, 1990.

O'Brien et al. HIV–1 tropism for mononuclear phagocytes can be determined by regions of gp120 outside the CD4–binding domain, Nature, vol. 348(1), p. 69–73, 1990.*

Stuber et al. Assessment of major histocompatibility complex class I interaction with Epstein–Barr virus and human immunodeficiency virus peptides by elevation of membrane H–2 and HLA in peptide loading–deficient cells, Eur. J. Immunol. vol. 22, p. 2697–, 1992.*

Yaron et al. Synthesis and immunological properties of the oligolysly–N'–dinitrophenyllysine and oligolysylalanylalanyl–N'–dinitrophenyllysine peptide series, Biochemistry, vol. 13(2), p. 347–354, 1974.*

Mayer et al. Block oligopeptides (L–Lysyl)m–(L–Alanyl)n–L–Tyrosyl–(L–Alanyl)n–(L–Lysyl)m. II. circular dichroism and pulsefluorimetry conformational studies, Biopolymers, vol. 17, p. 337–360, 1990.*

* cited by examiner

```
   1 CTCGATCTATTTTTTAAATATAATAAAATTAATAAAAATAAGTGGTAAAA   50
  51 GGAGAAAAGAATATTTAAAACAAAATATATTCTGTTGCCAGTAATAACAT  100
 101 TATTGTGTAATATGTATAGTGAGGTATTTACTCAAAGAGCAAGAAACAAA  150
 151 AATCAAAAAAATCGTTGTTAACGAACAAAATGAAAGATTAAAACGCTTAA  200
 201 TAAAAGCTTATGGAAAAATACATCTAGTAAAAGTTTAAAAGACATGACAA  250
 251 TTAAAGTAAAAAACAAAATAGCCTCAGGAGCAAGCAAAAAAGGATACTTC  300
 301 TTTAAAGGCCTAAAGGGTATTTTTATGCCTTTTAAGCCTGCCAATCCTTA  350
 351 TACTCCTAATTAAAAAAAATAAAGCAATATCAAAATAGTCAAAATACTCA  400
 401 AAAGAGAAGCCAATAAATTGCGGGAGATGGCTTCTCTTTTATTTTTAAGA  450
 451 CCTAATTATTTTAGACTTTGATTCAATTTGCAAAATAACCAATTTGAAAT  500
 501 ATTTTGGCAAACTGGAAACAAGTCTTAAAATACAAGCCAGATTGATAGAA  550
 551 ACTTGTAATTCCAAACAATGTTACTGCTATATTTGCATAAAACAAATTCA  600
 601 CACTAACAATAAAAATAATAAAATAAAACTTAAACTGATACGCTTTTAAA  650
 651 ATAAAAGTTTTAAACTTTAGTACAAATCTAGACATTATATTAACTTTTTA  700
 701 CATCAACATACTAACTAATTTATTTTATTTTATTTTTCATAAAGTGGGCT  750
 751 AAAATTTAAATTTAACTAAATTTAATAGAAGGAGGAAAAAATGAAAATTG  800
 801 GAAAGCTAAATTCAATAGTTATAGCCTTGTTTTTTAAACTATTGGTCGCA  850
 851 TGTAGTATTGGATTAGTAGAAAGAACAAATGCAGCTCTTGAATCGCTCTA  900
 901 AGGATTTAAAAACAAAATTTTAAAAATAAAAAAAGATGCCACGGGAAAAG  950
 951 GTGTACTTTTTGAAGCTTTTACAGGTCTTAAAACCGGTTCCAAGGTAACA 1000
1001 AGTGGTGGACTAGCCTTAAGAGAAGCAAAAGTACAAGCCATTGTTGAAAC 1050
1051 AGGAAAGTTCCTTAAGATAATAGAAGAAGAAGCTTTAAAGCTTAAAGAAA 1100
1101 CTGGAAACAGTGGTCAATTCTTGGCTATGTTTGACTTAATGCTTGAGGTT 1150
1151 GTAGAATCGCTAGAAGACGTTGGAATAATAGGCTTAAAAGCCCGTGTTTT 1200
1201 AGAGGAATCTAAAAATAATCTATAAACACAGCTGAAAGATTGCTTGCGGC 1250
1251 TAAAGCTCAAATAGAAAATCAACTTAAAGTGGTTAAGGAAAAACAAAATA 1300
1301 TTGAAAATGGTGGAGAGAAAAAAATAACAAAAGCAAAAAAAGAAATAA 1350
1351 ATATTAAAAATATTGTCATTAGAATGGACTAAAAGTAAAATTTTTGGCTC 1400
```

FIG. 10A

```
1401 GTCCTAATATTTACAATTTAATAATATTGGTTTATTGCTTTTATCTAAAA 1450
1451 TACAAAAAAAGGATAATGTTatgATTAAATGTAATAATAAAACTTTTAAC 1500
1501 AATTTACTTAAACTAACTATACTTGTTAACCTACTTATATCATGTGGACT 1550
1551 AACAGGAGCAACAAAAATCAAATTAGAATCATCAGCTAAAGCCATTGTAG 1600
1601 ATGAAATAGATGCAATTAAAAAAAAGGCTGCTTCTATGGGTGTAAATTTT 1650
1651 GATGCCTTTAAAGATAAAAAAACGGGTAGTGGGGTATCAGAAAATCCATT 1700
1701 CATACTTGAAGCAAAAGTGCGAGCTACTACAGTAGCGGAAAAATTCGTAA 1750
1751 TAGCAATAGAAGAGGAAGCTACTAAACTTAAAGAAACTGGAAGTAGTGGT 1800
1801 GAATTCTCAGCAATGTATGATTTAATGTTTGAAGTCTCAAAACCATTACA 1850
1851 AGAATTGGGAATACAAGAGATGACAAAAACAGTCTCAATGGCAGCTGAAG 1900
1901 AGAATCCTCCAACTACAGCTCAAGGAGTGCTTGAAATTGCAAAAAAAATG 1950
1951 AGAGAAAAATTACAAAGGGTTCACAAGAAAAACCAAGACACCTTAAAGAA 2000
2001 AAAAAATACCGAAGACAGCACTGCTAAATCGtaaTAAACACCATTTTTAT 2050
2051 ATGCAACTCAAAATAATAGACCAAACAACCACCTGTGTTGGGCTGTTTGG 2100
2101 TCTTACAATTTAAATGTTAATTCTGCAATGCAAAAAACAAATATTAAGCT 2150
2151 CTTCAACCAGCATTCAAAAGCTAAAATTAAGGTTAAAGCAATTAACCCAA 2200
2201 AGGATTTAAAATTTAAAAAATACTGTAATAAACATTAAAAGTTATAAAAT 2250
2251 GTAATTATTATTTTCAAACAAAATAATTAAATATCCTTTTTGATGTTATT 2300
2301 TGGAATTTCTTTCCTTTAGACTTTAAATCAAGACTGTCGTAAAGCACCTT 2350
2351 ATTATTATCCATTACAAGAAAATGCACAAAAACCCGACTTTACCTTAACT 2400
2401 CTGTTATTTCAAACTCTCAGCCAGCTTTAGGCAAATAAAGTGGACTCTCG 2450
2451 TATCTAACCTTGGAAAATATTTTATAACAACTAAGAATTTTACATGGATT 2500
2501 TAAAATATAACAATCCTTTCTAATGTAGCCTAATTCCAAAAACCGCTGAT 2550
2551 AATTTAAATTAACGTCTTTTGCTGTAAAATCAAACCCCTTTAAAACAAAT 2600
2601 ATCAATAGTGCAAAGACAAAAAATAACATCGGACTTTTGAATGTCTTTAA 2650
2651 ACA                                                 2653
```

FIG. 10B

```
  1 MIKCNNKTFNNLLKLTILVNLLISCGLTGATKIKLESSAK        40
 41 AIVDEIDAIKKAASMGVNFDAFKDKKTGSGVSENPFILE        80
 81 AKVRATTVAEKFVIAIEEEATKLKETGSSGEFSAMYDLMF       120
121 EVSKPLQELGIQEMTKTVSMAAEENPPTTAQGVLEIAKKM       160
161 REKLQRVHKKNQDTLKKKNTEDSTAKS                   187
```

FIG. 11

DECORIN BINDING PROTEIN COMPOSITIONS

The present application is a Divisional of application Ser. No. 08/589,711, filed Jan. 22, 1996, issued as U.S. Pat. No. 5,853,987 on Dec. 29, 1998, which is a continuation-in-part of U.S. Ser. No. 08/427,023, filed Apr. 24, 1995; now abandoned the entire text and figures of which disclosure are specifically incorporated herein by reference without disclaimer. The United States government has certain rights in the present invention pursuant to Grants AI20624, HL47313, and AR41507 from the National Institutes of Health.

BACKGROUND OF THE INVENTION

1. Field of the Invention

The present invention relates generally to the field of molecular biology. More particularly, certain embodiments concern methods and compositions comprising DNA segments, and proteins derived from bacterial species. More particularly, the invention provides gene compositions encoding a decorin (Dcn) binding protein (DBP) from *Borrelia burgdorferi* and the corresponding peptide epitopes and protein sequences comprising native and synthetically-modified Dcn binding site domains. Various methods for making and using these DNA segments, DNA segments encoding synthetically-modified ligand binding site domains, and native and synthetic proteins are disclosed, such as, for example, the use of DNA segments as diagnostic probes and templates for protein production, and the use of proteins, fusion protein carriers and peptides in various pharmacological and immunological applications.

2. Description of the Related Art

Lyme Disease

Lyme disease (Steere, 1989), or Lyme borreliosis, is transmitted by ticks, particularly of the genus Ixodes, and caused by spirochetes of the genus Borrelia. Lyme disease agents, that is borrelias isolated from humans or animals with clinical Lyme disease, are currently classified into at least three phylogenetic groups: *B. burgdorferi* sensu stricto, *B. garinii,* and *B. afzelii.* Strains potentially representing other phylogenetic groups of Lyme disease agents as well, such as group 25015, have been also isolated from ixodid ticks. Collectively these spirochetes are referred to as *B. burgdorferi* sensu lato, or simply *B. burgdorferi.* The genotypic and phenotypic variation among Lyme disease agents supporting the designation of these phylogenetic subgroupings is a major complicating factor for the design of effective vaccines or immunotherapeutic strategies for Lyme disease.

Lyme disease is transmitted through the bite of a tick which attaches itself to the host and, upon feeding, deposits the spirochetes into the dermis of the skin. In the skin, *B. burgdorferi* replicates before endovascular dissemination to organs. Typically, an annular spreading skin lesion, erythema migrans, forms from the site of the tick bite. Early symptoms of Lyme disease are flu-like and may include fatigue and lethargy. Left untreated, Lyme disease can develop into a chronic, multisystemic disorder involving the skin, joints, heart, and central nervous system.

Once deposited in the dermis, the spirochetes become associated with and appear to colonize the collagen fibers. Skin is the most consistent site of spirochete-positive culture. In persistent infection, the skin may provide a protective niche for replication, thereby acting as a reservoir of spirochetes for subsequent distribution to other tissues.

As *B. burgdorferi* disseminates to other organs, the organisms appear to localize to the extracellular spaces of these tissues as well. In several organs, including tendon (Barthold et al., 1993; 1991), ligament (Häupl et al., 1993), heart (Zimmer et al., 1990), and muscle (Barthold et al., 1992; Duray, 1992), *B. burgdorferi* spirochetes are found primarily in close association with collagen fibers, suggesting that this association is an important mechanism of tissue adherence in different stages of infection. Although the association of *B. burgdorfei* with collagen fibers has been reported previously by several investigators, the molecular mechanism responsible is not known. Lyme disease is typically treated with antibiotics, which are generally effective in the early stages of the disease. Later stages involving cardiac, arthritic, and nervous system disorders are often non-responsive.

Existing Vaccines for Prevention of Lyme Disease

Several proteins present on the outer surface of *B. burgdoreri* have been identified, including OspA (31 kDa), OspB (34 kDa), OspC (22 kDa), OspD, OspE, and OspF. Laboratory studies have shown that passively-administered antibodies (Schaible et al., 1990) reactive with the *B. burgdorferi* outer surface protein A (OspA), or immunization with recombinant OspA (Fikrig et al., 1990), protect mice from challenge with in vitro-grown or tick-borne *B. burgdorferi.* Based largely on the protective efficacy of experimental OspA vaccines in rodent models of Lyme borreliosis, three monovalent OspA-based vaccines are currently in clinical trials. However, recent findings suggest that broad, sustained protection of humans may be difficult to achieve with vaccines based solely on OspA.

Three observations, however, suggest that Osp-A-based vaccines may prove to have limited efficacy in treating Lyme disease in humans:

a) Modulation of OspA expression by *B. burgdorferi* may limit the site of action of OspA-specific antibodies to spirochetes residing in the tick midgut as these antibodies are ineffective shortly after infection;

b) Human immune responses to OspA subunit vaccines have not matched those of rodents in level or duration; and c) OspA is serologically diverse, particularly among European and Asian *B. garinii* and *B. afzeili* isolates. Reactivity with panels of OspA monoclonal antibodies (mAbs), and DNA sequence analysis has shown that as many as seven different OspA subgroups can be distinguished (Wilske et al., 1991; 1993).

Moreover, these variations will no doubt affect the cross-protection to be anticipated with OspA vaccines. Cross-protection was seen by one group using an immunocompetent mouse model (Fikrig et al., 1995), but cross-protection was weak or absent in SCID mouse or hamster models used by other (Schaible et al., 1993; Lovrich et al., 1995). An additional concern is that as many as 10% of *B. burgdorferi* isolates fail to express OspA in culture (Wilske et al., 1991; 1993).

Another problem with the use of OspA as antigens for stimulation of an immune response in an affected patient is the fact that OspA protein is either poorly immunogenic in humans, or not expressed by *B. burgdorferi* in vivo until late in infection. Lyme disease patients, mice, hamsters, and dogs infected by tick bite or low-doses of cultured *B. burgdorferi* fail to mount substantial anti-OspA immune responses for many months following infection although they do mount early responses to other *B. burgdorferi* antigens (flagellin, OspC, etc.) (Steere, 1989; Barthold and Bockenstedt, 1993). OspA is expressed by *B. burgdorferi* within ticks (Barbour et al., 1983), but detection of OspA on borrelia in tissue early after infection is difficult. Passive immunization of mice with OspA antibody (Schaible et al., 1990), or immunization with recombinant OspA, after challenge does not eliminate infection and only partially alters disease.

Unfortunately, OspA-immunized mice are not protected from a challenge with host-adapted spirochetes delivered in the form of skin biopsy transplants from infected mice (Barthold et al., 1995). The bacteria appear to express OspA in vivo only at later stages when the infection becomes disseminated. This would be explained by down-regulation of OspA expression by borrelia shortly after initiation of feeding by the tick.

Modulation of borrelia antigen expression within feeding ticks has recently been reported for OspC; initially low in resting ticks, OspC levels increase on *B. burgdorferi* after initiation of tick feeding (Schwan et al., 1995). OspC might appear to be a promising in vivo target, but its high level of antigenic variation complicates its development as a vaccine (Probert and LeFebvre, 1995).

In vitro cultivation of *B. burgdorferi* suggests that the genes for OspA and OspC are inversely regulated. Preliminary findings of some researchers do suggest that OspA levels similarly decrease after initiation of tick feeding. If these findings are confirmed, OspA antibodies will need to pre-exist at high levels in human or animal hosts prior to the tick bite to be effective against OspA-expressing borrelia in the tick, and may receive little or no boosting upon delivery of the spirochetes into the skin within the milieu of immunosuppressive components of the tick saliva (Urioste et al., 1994).

A recent publication (Telford et al., 1995) describes the efficacy of human Lyme disease vaccine formulations in a mouse model. The authors speculate that "(i)t is likely that titer of circulating antibody to OspA critically determines protection because of the unique mode of action of antispirochetal immunity, wherein antibody or other effectors interfere with the process of transmission within the gut of the infecting tick, before inoculation of the pathogen." Consistent with this hypothesis it has been shown that anti-borrelia serum can protect mice from infection by tick bite if administered within two days after initiation of feeding by borrelia-infected ticks, but not when passively administered at later times (Shih et al., 1995). The antibody levels in response to recombinant OspA subunit vaccinations seen to date in Phase II trials have been moderate, with serum ELISA titers <3,000, and drop off to near baseline levels within five months (Keller et al., 1994). The results in these studies indicate that it will be necessary to include additional antigens to achieve a protective vaccine for Lyme disease.

Deficiencies in the Prior Art

It is clear that while several approaches to the treatment of bacterial diseases have experienced some success, many problems remain, including antibiotic resistance, variability of antigens between species and species variation through mutation of antigens, as well as the need to protect susceptible groups such as young children, the elderly and other immunocompromised patients. Thus, there exists an immediate need for an effective treatment for *B. burgdorferi*, and vaccines against the causative agent of Lyme disease.

Although attempts have been made to utilize the Osps as vaccines to confer protection against *B. burgdorferi*, the results have been disappointing. Because these proteins have demonstrated strain specificity, e.g., variance among isolates and among different passages, and some lack of cross protection between strains, their potential use as vaccines remains very limited.

Because currently known antigens are not sufficient to elicit a protective immune response over a broad spectrum of *B. burgdorferi* strains, there continues to be an urgent need to develop novel prevention and treatment methods as well as novel antigens able to elicit a broad spectrum immune response and useful diagnostic methods for the prevention, treatment, and diagnosis of Lyme disease.

SUMMARY OF THE INVENTION

The present invention overcomes one or more of these and other drawbacks inherent in the prior art by providing novel compositions and methods for their use in the treatment of Lyme disease using non-antibiotic strategies. Disclosed are methods for the use of novel peptide and antibody compositions in the treatment of Lyme disease mediated by the inhibition of *B. burgdorferi* binding to the host cell ECM component, Dcn. Also disclosed are methods for active and passive immunization against *B. burgdorferi* and related borrelias including *B. afzelii* and *B. garinii* using novel native and site-specifically-altered DBP compositions and DBP-derived epitopic peptides from *B. burgdorferi*, *B. afzelii* and *B. garinii*. Particular aspects of the invention relate to novel nucleic acid segments encoding these peptides and epitopes, and methods for the use of such nucleic acid segments in a variety of diagnostic and therapeutic regimens.

dbp Nucleic Acid Compositions

The invention provides nucleic acid sequences encoding DBP. As used herein, a gene encoding DBP means a nucleic acid sequence encoding a DBP protein. A preferred nucleic acid sequence encoding a DBP gene is the nucleotide sequence of SEQ ID NO:1, and most preferably, the nucleotide sequence of the approximately 0.6 kb open reading frame of the *B. burgdorferi* dbp gene given in SEQ ID NO:3, or a strain variant or an active fragment thereof. It is expected that the gene encoding DBP will vary in nucleic acid sequence from strain to strain, but that the variation in nucleic acid sequence will not preclude hybridization between sequences encoding DBP of each strain under strict hybridization conditions.

As used herein, a strain variant of DBP means any polypeptide encoded, in whole or in part, by a nucleic acid sequence which hybridizes under strict hybridization conditions to a nucleic acid sequence of SEQ ID NO:1 encoding the DBP of strain 297, e.g., SEQ ID NO:2. One of skill in the art will understand that strain variants of DBP include those proteins encoded by nucleic acid sequences which may be amplified using the nucleic acid sequence of SEQ ID NO:1, and preferably from SEQ ID NO:3 encoding the 0.6 kb open reading frame.

SEQ ID NO:1 comprises the complete nucleotide sequence of a 2.5 kb insert of borrelia genomic DNA cloned in the pBlueScript™ vector. This recombinant clone, designated BG26:pB/2.5(5), has been deposited with the American Type Culture collection in *E. coli* strain JM101. This transformed host cell comprising the recombinant vector has been given the ATCC accession number ATCC69791. Contained within the 2.5-kb DNA insert from position 1471 to 2031 is the approximately 0.6 kb open reading frame comprising the *B. burgdorferi* dbp gene (SEQ ID NO:3). The deduced amino acid sequence of the 187-amino acid gene product is identified in SEQ ID NO:2.

In related embodiments, the invention also comprises strain variants of DBP and the dbp gene(s) encoding DBPs. Strain variants are those nucleic acid compositions and polypeptide compositions expressed by various strains of *B. burgdorferi* and related borrelias including *B. afzelii* and *B. garinii* which specifically encode DBPs. These DBPs also bind Dcn and related proteoglycans and share similarity of structure and function with the DBP of *B. burgdorferi* strain 297 encoded by the nucleic acid sequence of SEQ ID NO:1.

Aspects of the invention concern the identification of such strain variants using diagnostic methods and kits described herein. In particular, methods utilizing dbp gene sequences as nucleic acid hybridization probes and/or anti-DBP antibodies in western blots or related analyses are useful for the identification of such strain variants. The identity of potential strain variants of DBP may be confirmed by Dcn binding assays, e.g., by blot analysis with labeled Dcn, or alternatively by the demonstrating the ability of the strain-variant DBP to lessen or prevent adherence of *B. burgdorferi* and related borrelias including *B. afzelii* and *B. garinii* to Dcn.

Recombinant Expression of DBP

The present invention also concerns recombinant host cells for expression of an isolated dbp gene. It is contemplated that virtually any host cell may be employed for this purpose, but certain advantages may be found in using a bacterial host cell such as *E. coli, S. typhimurium, B. subtilis*, or others. Expression in eukaryotic cells is also contemplated such as those derived from yeast, insect, or mammalian cell lines. These recombinant host cells may be employed in connection with "overexpressing" DBP proteins, that is, increasing the level of expression over that found naturally in *B. burgdorferi*.

Proteins of amino acid sequence derived, from or similar to, DBP from strain 297 are anticipated to have affinity for Dcn and can be purified from other constituents of *B. burgdorferi* or recombinant host cells by chromatography on matrices containing Dcn, so-called "affinity chromatography." DBPs may also be purified by methodologies not relying on affinity for Dcn such as ion exchange chromatography, size exclusion chromatography, metal chelation chromatography, or the like. Buffer, detergent, and other conditions may be dissimilar from those optimal for "affinity chromatography." In a preferred embodiment, an affinity matrix comprising Dcn or a related proteoglycan may be used for the isolation of DBPs from solution, or alternatively, isolation of intact bacteria expressing DBPs, or even membrane fragments of bacteria expressing DBPs.

A particular aspect of this invention provides novel ways in which to utilize recombinant DBPs or DBP-derived peptides, nucleic acid segments encoding these peptides, recombinant vectors and transformed host cells comprising dbp or dbp-derived DNA segments, recombinant vectors and transformed host cells comprising dbp or dbp-derived DNA segments, and recombinant vectors and transformed host cells comprising *B. burgdorferi* dbp-derived DNA segments. As is well known to those of skill in the art, many such vectors and host cells are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a protein or peptide of interest (e.g., a DBP from Borrelia, and particularly a DBP from *B. burgdorferi, B. afzelii*, or *B. garinii*, and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various regulatory sequences.

After identifying an appropriate epitope-encoding nucleic acid molecule, it may be inserted into any one of the many vectors currently known in the art, so that it will direct the expression and production of the protein or peptide epitope of interest (e.g., a DBP from Borrelia and in particular, from *B. burgdorferi, B. afzelii, B. garinii*, or *B. japonica*) when incorporated into a host cell. In a recombinant expression vector, the coding portion of the DNA segment is positioned under the control of a promoter. The promoter may be in the form of the promoter which is naturally associated with a DBP-encoding nucleic acid segment, as may be obtained by isolating the 5' non-coding sequences located upstream of the coding segment, for example, using recombinant cloning and/or PCR™ technology, in connection with the compositions disclosed herein. Direct amplification of nucleic acids using the PCR™ technology of U.S. Pat. Nos. 4,683,195 and 4,683,202 (herein incorporated by reference) are particularly contemplated to be useful in such methodologies.

In certain embodiments, it is contemplated that particular advantages will be gained by positioning the DBP-encoding DNA segment under the control of a recombinant, or heterologous, promoter. As used herein, a recombinant or heterologous promoter is intended to refer to a promoter that is not normally associated with a dbp or dbp-like gene segment in its natural environment. Such promoters may include those normally associated with other MSCRAMM-encoding genes, and/or promoters isolated from any other bacterial, viral, eukaryotic, or mammalian cell. Naturally, it will be important to employ a promoter that effectively directs the expression of the DNA segment in the particular cell containing the vector comprising the DBP-encoding nucleic acid segment.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. For eukaryotic expression, the currently preferred promoters are those such as CMV, RSV LTR, the SV40 promoter alone, and the SV40 promoter in combination with the SV40 enhancer. In preferred embodiments, the expression of recombinant DBPs is carried out using prokaryotic expression systems, and in particular bacterial systems such as *E. coli*. Such prokaryotic expression of nucleic acid segments of the present invention may be performed using methods known to those of skill in the art, and will likely comprise expression vectors and promotor sequences such as those provided by tac, tip, lac, lacUV5 or T7 promotors.

For the expression of DBP and DBP-derived epitopes, once a suitable clone or clones have been obtained, whether they be native sequences or genetically-modified, one may proceed to prepare an expression system for the recombinant preparation of DBP or DBP-derived peptides. The engineering of DNA segment(s) for expression in a prokaryotic or eukaryotic system may be performed by techniques generally known to those of skill in recombinant expression. It is believed that virtually any expression system may be employed in the expression of DBP or DBP-derived epitopes.

Alternatively, it may be desirable in certain embodiments to express DBP or DBP-derived epitopes in eukaryotic expression systems. The DNA sequences encoding the desired DBP or DBP-derived epitope (either native or mutagenized) may be separately expressed in bacterial systems, with the encoded proteins being expressed as fusions with β-galactosidase, ubiquitin, *Schistosoma japonicum* glutathione S-transferase, *S. aureus* Protein A, maltose binding protein, and the like. It is believed that bacterial expression will ultimately have advantages over eukaryotic expression in terms of ease of use and quantity of materials obtained thereby.

It is proposed that transformation of host cells with DNA segments encoding such epitopes will provide a convenient means for obtaining DBP or DBP-derived peptides. Genomic sequences are suitable for eukaryotic expression, as the host cell will, of course, process the genomic transcripts to yield functional mRNA for translation into protein.

It is similarly believed that almost any eukaryotic expression system may be utilized for the expression of DBP and DBP-derived epitopes, e.g., baculovirus-based, glutamine synthase-based or dihydrofolate reductase-based systems may be employed. In preferred embodiments it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes nucleic acid sequences encoding DBP or DBP-derived peptides, an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

It is contemplated that virtually any of the commonly employed host cells can be used in connection with the expression of the DBP and DBP-derived epitopes in accordance herewith. Examples include cell lines typically employed for eukaryotic expression such as 239, AtT-20, HepG2, VERO, HeLa, CHO, WI 38, BHK, COS-7, RIN and MDCK cell lines.

It is further contemplated that the DBP or epitopic peptides derived from native or recombinant DBPs may be "overexpressed", i.e., expressed in increased levels relative to its natural expression in human cells, or even relative to the expression of other proteins in a recombinant host cell containing DBP-encoding DNA segments. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural DBP-producing cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a DBP has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a single structural gene, an entire genomic clone comprising a structural gene and flanking DNA, or an operon or other functional nucleic acid segment which may also include genes positioned either upstream and/or downstream of the promotor, regulatory elements, or structural gene itself, or even genes not naturally associated with the particular structural gene of interest.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive eukaryotic promoters include viral promoters such as the cytomegalovirus (CMV) promoter, the Rous sarcoma long-terminal repeat (LTR) sequence, or the SV40 early gene promoter. The use of these constitutive promoters will ensure a high, constant level of expression of the introduced genes. The inventors have noticed that the level of expression from the introduced genes of interest can vary in different clones, or genes isolated from different strains or bacteria. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

Immunological Detection of DBP and Bacteria Expressing DBPs

A further aspect of the invention is the preparation of immunological compositions, and in particular anti-DBP antibodies for diagnostic and therapeutic methods relating to the detection and treatment of infections caused by *B. burgdorferi* and related-borrelias-including *B. afzelii* and *B. garinii*.

Methods for Diagnosing Lyme Disease Using dbp Gene Compositions

Methods for diagnosing Lyme disease, and the detection of *B. burgdorferi* in clinical samples using nucleic acid compositions are also provided by the invention. The nucleic acid sequences encoding DBP are useful as diagnostic probes to detect the presence of *B. burgdorferi*, and related borrelias including *B. afzelii* and *B. garinii* in a test sample, using conventional techniques. In one such method of diagnosing Borrelial infection, dbp nucleic acid segments may be used in Southern hybridization analyses or Northern hybridization analyses to detect the presence of dbp nucleic acid segments within a clinical sample from a patient suspected of having such a disease. In a preferred embodiment, nucleic acid sequences as disclosed in SEQ ID NO:1 or SEQ ID NO:3 are preferable as probes for such hybridization analyses.

Methods for Producing an Immune Response

Also disclosed in a method of generating an immune response in an animal.

The method generally involves administering to an animal a pharmaceutical composition comprising an immunologically effective amount of a peptide composition disclosed herein. Preferred peptide compositions include the peptide disclosed in SEQ ID NO:2.

The invention also encompasses DBP and DBP-derived peptide antigen compositions together with pharmaceutically-acceptable excipients, carriers, diluents, adjuvants, and other components, such as additional peptides, antigens, or outer membrane preparations, as may be employed in the formulation of particular vaccines.

The nucleic acid sequences of the present invention encode DBP and are useful to generate pure recombinant DBP for administration to a host. Such administration is useful to prevent adherence of *B. burgdorferi* to the host's tissues or as a vaccine to induce therapeutic antibodies.

It is shown herein that antisera raised against and reactive with DBP is inhibitory to in vitro and in vivo growth of various *B. burgdorferi* strains. Thus, it is contemplated that administration of antibodies reactive with DBP to at-risk subjects will be effective for prophylaxis of, and in the case of infected subjects for therapy of, Lyme disease.

Antibodies may be of several types including those raised in heterologous donor animals or human volunteers immunized with DBPs, monoclonal antibodies (mAbs) resulting from hybridomas derived from fusions of B cells from DBP-immunized animals or humans with compatible myeloma cell lines, so-called "humanized" mAbs resulting from expression of gene fusions of combinatorial determining regions of mAb-encoding genes from heterologous species with genes encoding human antibodies, or DBP-reactive antibody-containing fractions of plasma from human donors residing in Lyme disease-endemic areas. It is contemplated that any of the techniques described above might be used for the vaccination of subjects for the purpose of antibody production. Optimal dosing of such antibodies is highly dependent upon the pharmacokinetics of the specific antibody population in the particular species to be treated, but it is anticipated that it will be necessary to maintain in these subjects a serum concentration of DBP-reactive- antibodies that is at least twice that required for inhibition of in vitro growth of endemic borrelia strains. It is contemplated that the duration of dosing maintaining anti-DBP levels at these inhibitory antibody concentrations would be for at least four to eight weeks following presumptive exposure to *B. burgdorferi*, or throughout the duration of symptoms of Lyme disease and for at least four to eight weeks after cessation of these symptoms.

Using the peptide antigens described herein, the present invention also provides methods of generating an immune response, which methods generally comprise administering to an animal, a pharmaceutically-acceptable composition comprising an immunologically effective amount of a DBP peptide composition. Preferred animals include mammals, and particularly humans. Other preferred animals include murines, bovines, equines, porcines, canines, and felines. The composition may include partially or significantly purified DBP peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 10 and about 50, even between about 50 and about 100 amino acids in length will often be preferred., The antigenic proteins or peptides may also be combined with other agents, such as other borrelial peptide or nucleic acid compositions, if desired.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments. Therefore, although these methods for the stimulation of an immune response include vaccination regimens designed to prevent or lessen significant infections caused by borrelias or other bacteria expressing a DBP, and treatment regimens that may lessen the severity or duration of any infection, it will be understood that achieving either of these end results is not necessary for practicing these aspects of the invention. Such treatment methods may be used particularly for the treatment of infections caused by pathogens such as *B. burgdorferi, B. afzelii, B.garinii*, related borrelial species, and other bacteria which express DBPs and adhere to Dcn.

Further means contemplated by the inventors for generating an immune response in an animal includes administering to the animal, or human subject, a pharmaceutically-acceptable composition comprising an immunologically effective amount of a nucleic acid composition encoding a DBP epitope, or an immunologically effective amount of an attenuated live organism that includes and expresses such a nucleic acid composition. The "immunologically effective amounts" are those amounts capable of stimulating a B cell and/or T cell response.

Immunoformulations of this invention, whether intended for vaccination, treatment, or for the generation of antibodies useful in the detection of borrelias and in particular *B. burgdorferi*, the prevention of bacterial adhesion, or in the case of bacterial colonization, promotion of bacterial adhesion to ECM components such as Dcn, may comprise native, or synthetically-derived antigenic peptide fragments from these proteins. As such, antigenic functional equivalents of the proteins and peptides described herein also fall within the scope of the present invention. An "antigenically functional equivalent" protein or peptide is one that incorporates an epitope that is immunologically cross-reactive with one or more epitopes derived from any of the particular MSCRAMM proteins disclosed (e.g., DBPs), and particularly the DBP of *B. burgdorferi* Antigenically functional equivalents, or epitopic sequences, may be first designed or predicted and then tested, or may simply be directly tested for cross-reactivity.

The identification or design of suitable DBP epitopes, and/or their functional equivalents, suitable for use in immunoformulations, vaccines, or simply as antigens (e.g., for use in detection protocols), is a relatively straightforward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences, for example, Chou and Fasman (1974a,b; 1978a,b; 1979); Jameson and Wolf (1988); Wolf et al. (1988); and Kyte and Doolittle (1982) address this subject. The amino acid sequence of these "epitopic core sequences" may then be readily incorporated into peptides, either through the application of peptide synthesis or recombinant technology.

It is proposed that the use of shorter antigenic peptides, e.g., about 25 to about 50, or even about 15 to 25 amino acids in length, that incorporate epitopes of the DBP will provide advantages in certain circumstances, for example, in the preparation of vaccines or in immunologic detection assays. Exemplary advantages include the ease of preparation and purification, the relatively low cost and improved reproducibility of production, and advantageous biodistribution.

In still further embodiments, the present invention concerns immunodetection methods and associated kits. It is contemplated that the proteins or peptides of the invention may be employed to detect antibodies having reactivity therewith, or, alternatively, antibodies prepared in accordance with the present invention, may be emmpoyed to detect DBP or peptides. Either type of kit may be used in the immunodetection of compounds, present within clinical samples, that are indicative of Lyme disease or related infections caused by borrelias, and in particular *B. burgdorferi*. The kits may also be used in antigen or antibody purification, as appropriate.

In general, the preferred immunodetection methods will include first obtaining a sample suspected of containing a DBP-reactive antibody, such as a biological sample from a patient, and contacting the sample with a first DBP or peptide under conditions effective to allow the formation of an immunocomplex (primary immune complex). One then detects the presence of any primary immunocomplexes that are formed.

Contacting the chosen sample with the DBP or peptide under conditions effective to allow the formation of (primary) immune complexes is generally a matter of simply adding the protein or peptide composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies and the remaining bound label is then detected.

For diagnostic purposes, it is proposed that virtually any sample suspected of containing the antibodies of interest may be employed. Exemplary samples include clinical samples obtained from a patient such as blood or serum samples, bronchoalveolar fluid, ear swabs, sputum samples, middle ear fluid or even perhaps urine samples may be employed. This allows for the diagnosis of Lyme disease and related infections caused by borrelias, and in particular, *B. burgdorferi*. Furthermore, it is contemplated that such embodiments may have application to non-clinical samples, such as in the titering of antibody samples, in the selection of hybridomas, and the like. Alternatively, the clinical samples may be from veterinary sources and may include such domestic animals as cattle, sheep, and goats. Samples from feline, canine, and equine sources may also be used in accordance with the methods described herein.

In related embodiments, the present invention contemplates the preparation of kits that may be employed to detect the presence of DBP-specific antibodies in a sample. Generally speaking, kits in accordance with the present invention will include a suitable protein or peptide together with an immunodetection reagent, and a means for containing the protein or peptide and reagent.

The immunodetection reagent will typically comprise a label associated with a DBP or peptide, or associated with a secondary binding ligand. Exemplary ligands might include a secondary antibody directed against the first DBP or peptide or antibody, or a biotin or avidin (or streptavidin) ligand having an associated label. Detectable labels linked to antibodies that have binding affinity for a human antibody are also contemplated, e.g., for protocols where the first reagent is a DBP peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

Methods for Inhibiting Bacterial Adhesion to Dcn

In addition, the DBP is useful as an agent to block *B. burgdorferi* adherence to Dcn, and proteoglycans which are structurally similar to Dcn such as Lmn, Fmn, Epn, and Bgn. In a preferred embodiment of the invention, a therapeutically effective dose of DBP is administered to a subject to prevent or block adhesion of *B. burgdorferi* to the host's tissues by conventional methods. The DBP is preferably systemically administered, but may be applied topically, e.g., to a localized lesion. The term therapeutically effective dose means that amount of DBP which is sufficient to lessen or prevent adherence of *B. burgdorferi* to a subject or to neutralize the known deleterious effects of *B. burgdorferi* infection and may be determined by known clinical methods. Absent adhesion of the bacteria to the tissues, the disease-inducing effects of the microorganism are halted, thus the DBP of the present invention is useful as a therapeutic agent to prevent adhesion of *B. burgdorferi* and thereby lessen or prevent disease induced by this microorganism.

Nucleic Acid Sequences Encoding DBP

As used herein, DBP means a purified and isolated protein including a strain variant or an active fragment thereof, derived form *B. burgdorferi* or a similar species which induces Lyme disease in a similar way, and having the ability to bind Dcn. Preferably, DBP is a recombinant protein encoded by a nucleic acid sequence contained within the *B. burgdorferi* DNA insert shown in FIG. 10A and 10B (SEQ ID NO:1), and most preferably is comprises the amino acid sequence of FIG. 11 (SEQ ID NO:2), or a strain variant or an active fragment thereof.

Alternatively, DBP means a protein selected from the group consisting of:

(a) polypeptides that are immunologically reactive with antibodies generated against *B. burgdorferi* and also immunologically reactive with DBP encoded by a nucleic acid sequence contained in SEQ ID NO:1 or with SEQ ID NO:3, or a strain variant thereof;

(b) polypeptides that are capable of eliciting antibodies that are immunologically reactive with DBP encoded by a nucleic acid sequence contained in SEQ ID NO:1 or SEQ ID NO:3 or a strain variant thereof; and (c) polypeptides that elicit in a treated mammal an immune response that is effective to lessen or prevent symptomatic disorders associated with Lyme disease, which polypeptides are also capable of eliciting antibodies that are immunologically reactive with DBP encoded by a nucleic acid sequence of SEQ ID NO:1 or SEQ ID NO:3 or with a strain variant thereof.

As used herein, an active fragment of DBP includes DBP which is modified by conventional techniques, e.g., by addition, deletion, or substitution, but which active fragment exhibits substantially the same structure and function as DBP as described herein. For example, portions of the protein not required to block adherence of *B. burgdorferi* to Dcn may be deleted or altered; additions to the protein may be made to enhance the protein's antigenicity according to conventional methods.

As used herein, DBP which confer protection against Lyme disease means DBP or fragments thereof which prevent or lessen adhesion of *B. burgdorferi* to Dcn, or prevent or lessen adhesion the severity of any of the disorders associated with *B. burgdorferi* infection, including erythema migrans, arthritis, carditis, neurological disorders, and any other Lyme disease related disorder.

Other aspects of the present invention concern isolated DNA segments and recombinant vectors encoding DBP, and the creation and use of recombinant host cells through the application of DNA technology, that express DBP gene products. As such, the invention concerns DNA segment comprising an isolated gene that encodes a protein or peptide that includes an amino acid sequence essentially as set forth by a contiguous sequence from SEQ ID NO:2. These DNA segments are represented by those that include a nucleic acid sequence essentially as set forth by a contiguous sequence from SEQ ID NO:1 (FIG. 10A and FIG. 10B). Compositions that include a purified protein that has an amino acid sequence essentially as set forth by the amino acid sequence of SEQ ID NO:2 (FIG. 11) are also encompassed by the invention.

Regarding the novel protein DBP, the present invention concerns DNA segments, that can be isolated from virtually any bacterial source, that are free from total genomic DNA and that encode proteins having DBP-like activity. DNA segments encoding DBP-like species may prove to encode proteins, polypeptides, subunits, functional domains, and the like.

As used herein, the term "DNA segment" refers to a DNA molecule that has been isolated free of total genomic DNA of a particular species. Therefore, a DNA segment encoding DBP refers to a DNA segment that contains DBP coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified DBP gene refers to a DNA segment including DBP coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, extra-genomic and plasmid-encoded sequences and smaller engineered gene segments that express, or may be adapted to express, proteins, polypeptides or peptides. Such segments may be naturally isolated, or modified synthetically by the hand of man.

"Isolated substantially away from other coding sequences" means that the gene of interest, in this case, a gene encoding DBP, forms the significant part of the coding region of the DNA segment, and that the DNA segment does not contain large portions of naturally-occurring coding DNA, such as large chromosomal fragments or other functional genes or polypeptide coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a DBP species that includes within its amino acid sequence an amino acid sequence essentially as set forth in SEQ ID NO:2. In other particular embodiments, the invention concerns isolated DNA segments and recombinant vectors incorporating DNA sequences that include within their sequence a nucleotide sequence essentially as set forth in SEQ ID NO:1.

The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO:2. The term "biologically functional equivalent" is well understood in the art and is further defined in detail herein (for example, see Illustrative Embodiments). Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 will be sequences that are "essentially as set forth in SEQ ID NO:2".

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1 and has relatively few codons that are not identical, or functionally equivalent, to the codons of SEQ ID NO:1. Again, DNA segments that encode proteins exhibiting DBP-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various upstream or downstream regulatory or structural genes.

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1, such as about 14 nucleotides, and that are up to about 10,000 or about 5,000 base pairs in length, with segments of about 3,000 being preferred in certain cases. DNA segments with total lengths of about 2,000, about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid and amino acid sequences as disclosed in SEQ ID NO:1 and SEQ ID NO:2, respectively. Recombinant vectors and isolated DNA segments may therefore variously include the DBP coding regions themselves, coding regions bearing selected alterations or modifications in the basic coding region, or they may encode larger polypeptides that nevertheless include DBP coding regions or may encode biologically functional equivalent proteins or peptides that have variant amino acids sequences.

The DNA segments of the present invention encompass biologically functional equivalent DBP proteins and peptides, in particular those DBP proteins isolated from prokaryotic sources, and particularly bacteria. DNA segments isolated from species of Borrelia and related bacteria which are shown to bind Dcn are particularly preferred for use in the methods disclosed herein. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the DBP coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a DBP gene, as may be obtained by isolating the 5' non-coding sequences located upstream of the coding segment, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DBP gene in its natural environment. Such promoters may include DBP promoters normally associated with other genes, and/or promoters isolated from any bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989 The promoters employed may be constitutive, or inducible, and can be used under the appropriate conditions to direct high level expression of the introduced DNA segment, such as is advantageous in the large-scale production of recombinant proteins or peptides.

Prokaryotic expression of nucleic acid segments of the present invention may be performed using methods known to those of skill in the art, and will likely comprise expression vectors and promotor sequences such as those provided by tac, trp, lac, lacUVS or T7. When expression of the recombinant DBP proteins is desired in eukaryotic cells, a number of expression systems are available and known to those of skill in the art. An exemplary eukaryotic promoter system contemplated for use in high-level expression is the Pichia expression vector system (Pharmacia LKB Biotechnology).

In connection with expression embodiments to prepare recombinant DBP and peptides, it is contemplated that longer DNA segments will most often be used, with DNA segments encoding the entire DBP or functional domains, epitopes, ligand binding domains, subunits, etc. being most preferred. However, it will be appreciated that the use of shorter DNA segments to direct the expression of DBP peptides or epitopic core regions, such as may be used to generate anti-DBP antibodies, also falls within the scope of the invention. DNA segments that encode peptide antigens from about 15 to about 100 amino acids in length, or more preferably, from about 15 to about 50 amino acids in length are contemplated to be particularly useful.

The dbp gene and DNA segments may also be used in connection with somatic expression in an animal or in the creation of a transgenic animal. Again, in such embodiments, the use of a recombinant vector that directs the expression of the full length or active DBP protein is particularly contemplated. Expression of dbp transgene in animals is particularly contemplated to be useful in the production of Anti-DBP antibodies for use in passive immunization methods for prevention of borrelial adhesion to Dcn, and treatment of infections due to Borrelia invasion, and particularly invasion by *B. burgdorferi.*

In addition to their use in directing the expression of DBP, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:1 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to DBP-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to SEQ ID NO:1, are particularly contemplated as hybridization probes for use in, e.g., Southern and Northern blotting. This would allow DBP structural or regulatory genes to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 14 and about 100 nucleotides, but larger contiguous complementarity stretches may be used, according to the length complementary sequences one wishes to detect.

The use of a hybridization probe of about 14–25 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1 and to select any continuous portion of the sequence, from about 14–25 nucleotides in length up to and including the full length sequence, that one wishes to utilize as a probe or primer. The choice of probe and primer sequences may be governed by various factors, such as, by way of example only, one may wish to employ primers from towards the termini of the total sequence.

The process of selecting and preparing a nucleic acid segment that includes a contiguous sequence from within SEQ ID NO:1 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of the entire dbp gene or gene fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of 50° C. to 70° C. Such selective conditions tolerate little, if any, mismatch between the probe and the template or target strand, and would be particularly suitable for isolating DBP genes.

Of course, for some applications, for example, where one desires to prepare mutants employing a mutant primer strand hybridized to an underlying template or where one seeks to isolate DBP-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

Anti-DBP Antibody Compositions

In a preferred embodiment, administration of a therapeutically effective dose of DBP to a subject induces in the subject antibodies which bind and neutralize *B. burgdorferi* present in the subject, thereby preventing the deleterious effects of this microorganism. Alternatively, anti-*B. burgdorferi* antibodies generated in a first host animal provide antibodies which can be administered to a second subject for passive immunization or treatment against *B. burgdorferi* infection. Such anti-*B. burgdorferi* antibodies are also useful as a diagnostic screen for the presence of *B. burgdorferi* in a test sample, using conventional immunoassay techniques.

In the present invention, a novel nucleic acid sequence (SEQ ID NO:1) encodes DBP of *B. burgdorferi* strain 297. Strain variants are prepared and screened by amplification of nucleic acid sequences of other strains of *B. burgdorferi* or similar Lyme-disease inducing bacteria using oligonucleotide probes derived from the 2.5 kb insert of *B. burgdorferi* strain 297 (SEQ ID NO:1) and preferably from the approximate 0.6 kb open reading frame. Clones obtained from the amplification procedures are then used as hybridization probes to isolate the full length nucleic acid encoding strain variants. Alternatively, DNA libraries for each strain are constructed and screened for clones expressing a DBP, e.g., by their affinity for Dcn.

In certain aspects, the present invention concerns novel antibody compositions which inhibit Dcn binding to bacteria. In particular, antibodies to native and synthetically-modified epitopes from DBPs have been developed which inhibit Dcn binding to DBPs both in vitro and in vivo. In particular, proteins, peptides and peptide epitopes have been produced to provide vaccine compositions useful in the prevention of Lyme disease and antibody compositions useful in the prevention of Dcn binding to Borrelias.

In other embodiments, the present invention encompasses antibody compositions which enhance Dcn binding to bacterial cells. These aspects provide methods and compositions for producing bacterial colonization of an animal host with attenuated, or avirulent Borrelias expressing cell surface DBP epitopes.

In one aspect, the invention discloses an antibody that interacts with a DBP domain of a bacteria dbp gene product, and particularly, a DBP domain of a *B. burgdorferi* dbp gene product. Such antibody may be monoclonal, or preferably polyclonal. In another aspect, the invention discloses an antibody which inhibits bacterial adhesion, and the binding of the gene product to Dcn.

Also disclosed is a method for detecting a bacterium expressing a DBP in a sample. The method generally involves obtaining a sample suspected of containing a bacterium expressing such a protein, then contacting the sample with an antibody composition disclosed herein, and detecting the formation of immune complexes. In preferred embodiments, the bacterium is a borrelia, and most preferably, a *B. burgdorferi, B. afzelii,* or *B. garinii* strain.

Methods of Use for dbp Nucleic Acid Segments

Another aspect of the invention are immunodetection kits containing antibodies of the present invention and suitable immunodetection reagents such as a detectable label linked to a protein, peptide or the antibody itself. Alternatively, the detectable label may be linked to a second antibody which binds to an antibody of the invention.

Related embodiments include diagnostic and therapeutic kits which include pharmaceutically-acceptable formulations of either the antibodies or peptide antigens disclosed herein. Such kits are useful in the detection of borrelias in clinical samples, and also useful for inhibiting or promoting the binding of borrelias to the ECM component, Dcn. In preferred embodiments, the bacteria detected using such kits include borrelias, and in particular, *B. burgdorferie, B. afzelii, B. garinii,* or related species.

Other aspects of the invention include methods of inhibiting bacterial colonization, and particularly colonization by borrelias, in an animal by administering to the animal an antibody of the present invention which prevents or significantly reduces the binding of Dcn to the DBP expressed by the bacteria. Administration of the antibody composition may be prophylactically prior to and/or following diagnosis of Lyme disease or other multisystemic disorders caused by Borrelioses which may involve the skin, joints, heart, and central nervous system. The administration may also be made in passive immunization protocols designed to prevent and/or ameliorate systemic infections by susceptible pathogens, and in particular, to ameliorate the effects of infections by pathogenic *B. burgdorferi*.

Nucleic Acid Segments and Vectors

The present invention includes proteins expressed from genes encoding a DBP such as that protein expressed from the DNA insert of recombinant clone BG26:pB/2.5(5). Also included are strain variants of the gene derived from *B. burgdorferi* strain 297 present in the recombinant clone BG26:pB/2.5(5) which also encode proteins capable of binding Dcn, which may hybridize to DNA derived from BG26:pB/2.5(5) under conditions of moderate or high stringency, or which may serve as templates for gene amplification by PCR™ using oligonucleotide primers derived from BG26:pB/2.5(5). It is understood that these variants may include genes containing codons not identical in nucleotide sequence to those of the dbp gene of strain 297, but encoding the same, or functionally equivalent amino acid, as is anticipated by those practiced in the art who understand the degeneracy of the genetic code. These variants may also include those genes similar to the dbp gene from strain 297, but having codons specifying relatively few amino acids that are different from those of the protein(s) encoded by BG26:pB/2.5(5), or having somewhat fewer or greater numbers of these codons. Accordingly such sequences include those that have between about 60% and about 80%; or more preferably, between about 81% and about 90%; or even more preferably, between about 91% and about 99%; of amino acids that are identical or functionally equivalent to those of protein(s) encoded by BG26:pB/2.5(5).

It is also understood that amino acid sequences and nucleic acid sequences may include additional residues, such as additional N- or C-terminal amino acids, or 5' or 3' nucleic acid sequences, and yet still be as set forth herein, so long as the sequence meets the criteria set forth above including the expression of a DBP protein. These additional sequences may, for example, include various transcriptional promoters, enhancers, or terminators, various secretion-directing leader peptides, various amino acid sequences directing posttranslational modifications, amino acids or peptides which may facilitate isolation and purification of DBP(s), and the like. Naturally, alterations and additions to these sequences will be made given consideration of the cell type, organism, or animal that will be chosen for expression of DBP(s).

Formulation as Vaccites

It is expected that to achieve an "immunologically effective formulation" it may be desirable to administer DBPs to the human or animal subject in a pharmaceutically acceptable composition comprising an immunologically effective amount of DBPs mixed with other excipients, carriers, or diluents which may improve or otherwise alter stimulation of B cell and/or T cell responses,or immunologically inert salts, organic acids and bases, carbohydrates, and the like, which promote stability of such mixtures. Immunostimulatory excipients, often referred to as adjuvants, may include salts of aluminum (often referred to as Alums), simple or complex fatty acids and sterol compounds, physiologically acceptable oils, polymeric carbohydrates, chemically or genetically modified protein toxins, and various particulate or emulsified combinations thereof. DBPs or peptides within these mixtures, or each variant if more than one are present, would be expected to comprise about 0.0001 to 1.0 milligrams, or more preferably about 0.001 to 0.1 milligrams, or even more preferably less than 0.1 milligrams per dose.

It is also contemplated that attenuated organisms may be engineered to express recombinant DBP gene products and themselves be delivery vehicles for the invention. Particularly preferred are attenuated bacterial species such as Mycobacterium, and in particular *M. bovis, M. smegmnatis,* or BCG. Alternatively, pox-, polio-, adeno-, or other viruses, and bacteria such as Salmonella, Shigella, Listeria, Streptococcus species may also be used in conjunction with the methods and compositions disclosed herein.

The naked DNA technology, often referred to as genetic immunization, has been shown to be suitable for protection against infectious organisms. Such DNA segments could be used in a variety of forms including naked DNA and plasmid DNA, and may administered to the subject in a variety of ways including parenteral, mucosal, and so-called microprojectile-based "gene-gun" inoculations. The use of dbp nucleic acid compositions of the present invention in such immunization techniques is thus proposed to be useful as a vaccination strategy against Lyme disease.

It is recognized by those skilled in the art that an optimal dosing schedule of a vaccination regimen may include as many as five to six, but preferably three to five, or even more preferably one to three administrations of the immunizing entity given at intervals of as few as two to four weeks, to as long as five to ten years, or occasionally at even longer intervals.

Recombinant Host Cells and Vectors

Particular aspects of the invention concern the use of plasmid vectors for the cloning and expression of recombinant peptides, and particular peptide epitopes comprising either native, or site-specifically mutated DBP epitopes. The generation of recombinant vectors, transformation of host cells, and expression of recombinant proteins is well-known to those of skill in the art. Prokaryotic hosts are preferred for expression of the peptide compositions of the present invention. An example of a preferred prokaryotic host is *E. coli*, and in particular, *E. coli* strains ATCC69791, BL21(DE3), JM101, XL1-Blue™, RR1, LE392, B, X1776 (ATCC No. 31537), and W3110 (F-, lambda-, prototrophic, ATCC273325). Alternatively, other Enterobacteriaceae species such as *Salmonella typhimurium* and *Serratia marcescens,* or even other Gram-negative hosts including various Pseudomonas species may be used in the recombinant expression of the genetic constructs disclosed herein. Borrelias themselves may be used to express these constructs, and in particular, *B. burgdorferi, B. afzelii, B. japonica* and *B. garinii.*

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be typically transformed using vectors such as pBR322, or any of its derivatives (Bolivar et al., 1977). pBR322 contains genes for ampicillin and tetracycline resistance and thus provides easy means for identifying transformed cells. pBR322, its derivatives, or other microbial plasmids or bacteriophage may also contain, or be modified to contain, promoters which can be used by the microbial organism for expression of endogenous proteins. A preferred vector for cloning the dbp constructs is pBlueScript™, and in particular the construct BG26:pB/2.5(5), or alternatively, vectors based on the pET vector series (Novagen, Inc., Madison, Wis.).

In addition; phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). The use of recombinant and native microbial promoters is well-known to those of skill in the art, and details concerning their nucleotide sequences and specific methodologies are in the public domain, enabling a skilled worker to construct particular recombinant vectors and expression systems for the purpose of producing compositions of the present invention.

In addition to the preferred embodiment expression in prokaryotes, eukaryotic microbes, such as yeast cultures may also be used in conjunction with the methods disclosed herein. *Saccharomyces cerevisiae,* or common bakers' yeast is the most commonly used among eukaryotic microorganisms, although a number of other species may also be employed for such eukaryotic expression systems. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4–1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the Bg/I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently-, or colloidal gold-tagged. Means for the labeling and detection of such two-step secondary antibody techniques are well-known to those of skill in the art.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 10A. DNA sequence of a 2.5 kb insert of *B. burgdorferi* strain 297 DNA contained in the plasmid BG26:pB/2.5(5), which comprises a nucleic acid sequence which encodes DBP. The deduced amino acid sequence is shown in FIG. 11. Shown in this panel are nucleotides 1–1400. The DNA sequence from position 1401 to 2653is continued in FIG. 10B.

FIG. 10B. Continuation of the nucleotide sequence of the dbp gene from *B. burgdorferi* strain 297 starting at nucleotide 1401 and continuing to the end of the clone, position 2653.

FIG. 11. Amino acid sequence of the 187 amino-acid DBP from *B. burgdorferi* strain 297.

DESCRIPTION OF ILLUSTRATIVE EMBODIMENTS

Figure 1A:
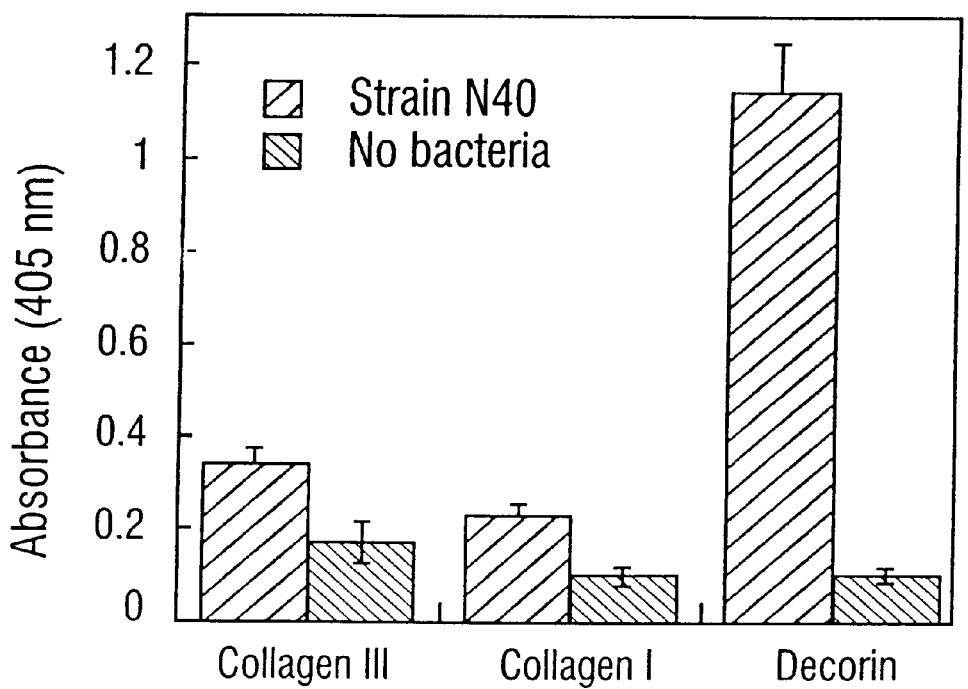
FIG. 1A. Attachment of bacterial strains to microtiter wells coated with type III collagen, type I collagen, or Dcn. Protein-coated microtiter wells were incubated with *B. burgdorferi* N40 or no bacteria. Attachment to the substrate was quantitated by an ELISA. Error bars represent the standard deviations of three separate determinations.

The technology described herein is used to develop methods and compositions that specifically interfere with bacterial adhesion and the subsequent colonization host tissues, thus resulting in the prevention of infection. The technology is broadly applicable, has the potential to increase the effectiveness of antibiotic therapy in many situations, and replace antibiotic therapy in a number of other applications. The technology is anticipated to be especially effective in treatment regimens for Lyme disease, and as a cost-effective prophylaxis for prevention of borrelial infections.

Some Advantages of the Invention

Those of ordinary skill having the benefit of this disclosure will appreciate that the invention provides a number of advantages, including the following:

DBP-Derived Antigens are Superior to OspA Antigens

The data from the biochemical and immunological characterization of the *B. burgdorferi* DBP herein show that Lyme disease vaccines derived from DBP do not suffer the limitations of the prior art, particularly with respect to OspA and other antigens previously investigated as antigens for development of borrelia vaccines. Indeed, vaccine compositions comprising DBPs are likely to be superior to those previously available containing OspA alone.

Serological Variation of DBP

The serological variation of DBP appears to be less than that of OspA as antibodies reactive with DBP derived from *B. burgdorferi* sensu stricto are also growth-inhibitory to strains of *B. garinii* and *B. afzelii*.

rDBP Immunization Protects Against Heterologous Strains

The data of the present invention demonstrate that immunization of mice with recombinant DBP protects against challenge from heterologous strains of *B. burgdorferi*.

DBP Vaccines Provide Superior Efficacy

Unlike OspA, DBP remains a target for immune intervention for several days after initiation of infection, and is the only antigen shown to date to possess this desirable property with respect to potential vaccine efficacy.

Anti-DBP Antibodies Eliminate Borrelias From Infected Animals

DBP-targeted antibodies administered several days after initiation of infection can eliminate viable spirochetes from infected mice, suggesting that this antigen is also a potential target for immunotherapy of Lyme disease as well as for immunoprophylaxis. Biochemical data is provided showing that DBP is a lipoprotein, and is exposed at the surface of the spirochetal outer membrane.

dbp Nucleic Acid Segments Useful in Identifying Borrelial Isolates

The novel dbp genes disclosed herein may be used to identify and isolate molecular clones of alleles of this gene present in different phylogenetic groups of Lyme disease spirochetes including *B. garinii* and *B. afzelii* by utilization of such techniques as PCR™.

MSCRAMMs

Bacterial adherence to host tissue involves specific microbial surface adhesins of which a subfamily termed MSCRAMMs (microbial surface components recognizing adhesive matrix molecules, Patti et al., 1994; Patti and Hook, 1994) specifically recognize extracellular matrix components. Many pathogenic bacteria have been shown to specifically recognize and bind to various components of the extracellular matrix in an interaction which appears to represent a host tissue colonization mechanism.

MSCRAMMs (on the bacterial cell surface) and ligands (within the host tissue) are the molecules that interact in a lock and key fashion resulting in the adherence of bacteria to the host. Complete blockage of microbial adhesion is not required to prevent infection. It is only necessary to keep the bacterial inoculum below a critical mass. Several strategies have been developed which are particularly useful in combatting bacterial infections, such as infection by *B. burgdorferi*, by preventing bacterial adhesion to Dcn substrata including the extracellular matrix (ECM) of susceptible host cells. Such strategies are contemplated to be useful in the diagnosis, treatment, and prophylaxis of Lyme disease.

Extracellular Matrix

The ECM contains numerous glycoproteins and proteoglycans which, through inter- and intramolecular interactions, form insoluble matrices. The ECM has a structural function in the tissues but also affects the cellular physiology of the organism. Perhaps the best characterized biological functions of the ECM are related to its ability to serve as a substrata for the adhesion of host tissue cells. This process involves the integrins, a family of heterodimeric ($\alpha/\beta$) cell surface receptors which recognize specific structures in many of the ECM proteins. It is clear that many bacteria also have taken advantage of the ECM as a substrate for adhesion. Like most eukaryotic tissue cells, many bacteria have developed several parallel adhesion mechanisms and this apparent redundancy may reflect the importance of host tissue adherence for the prosperity of the bacteria.

The adherence of microbes to various cell-surface and extracellular matrix components has been widely reported (Abraham et al., 1983; Coburn et al., 1993; Fröman et al., 1984; Isaacs, 1994; Maxe et al., 1986; Van Nhieu and Isber, 1993). The present invention has identified a new bacterial MSCRAMM which promotes bacterial adhesion to Dcn and other proteoglycans which are structurally similar to Dcn, which are found in conjunction with ECM components such as collagen.

Collagen

Collagenous proteins are the major constituents of the ECM (Bornstein and Sage, 1980). Most collagens are synthesized intracellularly as precursor molecules and undergo extensive posttranslational processing prior to secretion and incorporation into the ECM or other collagen-rich tissues such as cartilage (Ramachandran and Reddi, 1976). To date over 18 different type of collagens have been defined, and they are loosely categorized into five groups (Vanderrest and Garrone, 1991). These groups are:

1) collagen types I, II, III, V, and XI which participate in quarter-staggered fibrils;
2) collagen types XII, XIV, and IX which are fibril-associated with interrupted triple helices;
3) collagen types IV, VIII, and X which form sheets;
4) collagen type VI which forms beaded filaments; and
5) collagen type VII, which forms anchoring fibrils.

The collagen network in skin is composed predominantly of collagens type I and type III. Dcn can inhibit transforming growth factor beta activity (TGFβ) (Yamaguchi et al., 1990) and inactivate the complement component C1q (Krumdieck et al., 1992) and has been proposed to act as an anti-inflammatory agent through these interactions.

Proteoglycans

Decorin

Dcn, also known as PG-40, PG-II, PG-S2 and CSIDS-PGII, is a small proteoglycan with a single chondroitin or dermatan sulfate chain attached to the fourth amino acid of the secreted 36–38 kDa protein (Chopra et al., 1985). Dcn has been found associated with collagen fibrils in virtually all connective tissues (Bianco et al., 1990), perhaps near the d and e bands in the D period (Pringle and Dodd, 1990). In vitro studies have shown that Dcn can change the kinetics of collagen fibril formation (Vogel et al., 1984, affect the morphology of forming collagen fibrils (Vogel and Trotter, 1987) and bind to TGF-β (Yamaguchi et al., 1990).

Dcn, so named because it "decorates" collagen fibers in the intracellular matrix, has been shown to bind different collagen types and is believed to act as a regulator of collagen fiber formation. The proteoglycan can be isolated from many different tissues, including skin, cartilage, and tendon.

Dcn consists of a 36 kDa core protein, a single, serine-linked glycosaminoglycan (GAG) chain of the chondroitin/dermatan sulfate type, and up to three N-linked oligosaccharide. The GAGs are unbranched polysaccharides consisting of repeating disaccharide units, highly sulfated and therefore highly negatively charged. Dcn containing a chondroitin-4-sulfate chain is isolated from developing bone (Fisher et al., 1987) while Dcn containing a dermatan sulfate chain is generally isolated from articular cartilage (Choi et al., 1989) or tendon (Vogel and Heinegard, 1985). The Dcn is heterogenous with respect to glycosaminoglycan chain size and the average size of the chains differ with tissue and developmental age, however, the Alcian blue or StainsAll band generally are centered from 100 to 250 kDa. While Dcn size may differ in different tissues, it is almost always smaller than the biglycan (Bgn) proteoglycan in the same tissue. Both the human (Krusius and Ruoslahti, 1986) and bovine (Day et al., 1987) cDNA have been published and show a ~36–38 kDa core protein. Dcn changes the kinetics of the generation of collagen fibrils in vitro (Vogel et al., 1984) and affects the final morphology of the resulting fibrils (Vogel and Trotter, 1987). While these results suggest that Dcn may play an important role in collagen fibril formation, it is still unknown why the small proteoglycan is maintained on the fibrils throughout life, well after the fibrils are crosslinked and stabilized. When the expression of high levels of Dcn is induced in Chinese hamster ovary (CHO) cells, their morphology and growth properties are dramatically changed (Yamaguchi and Ruoslahti, 1988).

The gene encoding Dcn has been localized to human chromosome 12 (McBride et al., 1990), and Dcn itself shows obvious homology to other small proteoglycans, including Bgn (Fisher et al., 1989), and Fmn (Oldberg et al., 1989), Epn, and Lmn. These proteoglycans are predominantly composed of 10–12 tandem repeats with each nominal 24 amino acid repeat having a pattern of hydrophobic amino acids (Fisher et al., 1989; Oldberg et al., 1989). These repeat sequences have been used many times in evolution when protein-protein, protein-cell or cell-cell interactions are required. While Dcn, like Fmn, is found associated with collagen fibrils (Oldberg et al., 1989), Bgn appears to be associated on or very near cell surfaces and not collagen bundles (Bianco et al., 1990).

Biglycan (Bgn)

Bgn (Fisher et al., 1989) is a small proteoglycan whose primary gene product is found associated with the cell surface or pericellular matrix of a variety of cells including specific subsets of developing mesenchymal (skeletal muscle, bone and cartilage), endothelial (blood vessels), and epithelial (keratinocytes cells) (Bianco et al., 1990). Other names for this proteoglycan includes; PG-1, PG-I, DS-PGI, PG-S1 and DS-I. Bgn is composed of two chondroitin (CS) or dermatan sulfate (DS) chains on a 38 kDa core protein that is predominantly made of 12 tandem 24 amino acid repeat structures, each characterized by ordered hydrophobic residues. Similar tandem repeat structures have been used throughout evolution when a protein is destined to bind another protein or perhaps a cell surface (Fisher et al., 1989; Patthy, 1987). The function of Bgn is unknown, but, like the homologous proteoglycan, Dcn, it may also bind to TGF-β.

The chondroitin sulfate containing Bgn is most commonly isolated from fetal or young bone (Fisher et al., 1987; 1983), while the dermatan sulfate containing form is isolated from articular cartilage (Choi et al., 1989). The Bgn is heterogeneous with respect to the size of the glycosaminoglycan chains which results in a broad band on SDS-PAGE centered anywhere from 200–350 kDa. Although Bgn may differ in size between tissues and developmental stage, it is almost always larger than the other small proteoglycan, Dcn, when Dcn is also present. Bgn may occasionally be present with a single CSIDS chain, thus making it the same size as Dcn. Removal of the glycosaminoglycan chains with the enzyme chondroitin ABC-lyase results in a 45 kDa band. The gene for Bgn is on the human X chromosome (Xq27ter) (Fisher et al., 1989) and its mRNA encodes a 42.5 kDa preproprotein. The human (cDNA) (Fisher et al., 1989), bovine protein (Neame et al., 1989) and rat (Dreher et al., 1990) sequences have been reported. Bgn probably contains three disulfide bonds. Unlike its close relatives, Dcn and Fmn, purified Bgn does not bind to collagen fibrils in vitro, nor is it found associated with classic collagen bundles in tissues. Bgn (both protein and mRNA) is expressed in a range of specialized cell types in developing human tissues including bone, cartilage, blood vessel endothelial cells, skeletal myofibrils, renal tubular epithelia, and differentiating keratinocytes (Bianco et al., 1990). Generally, the Bgn is immunolocalized to the cell surface or pericellular matrices, but in a tissue such as bone, the protein is detected in the matrix proper. This localization in the extracellular matrix may be due to the adsorption of the Bgn to hydroxylapatite crystals after having been shed from the osteoblasts. Localization of Bgn by immunoelectron microscopy has not yet been performed. The human Bgn gene has been cloned and partially sequenced.

Fibromodulin (Fmn)

Fmn (or 59 kDa cartilage protein) is a keratan/sulfate proteoglycan present in many types of connective tissues, e.g. cartilage, tendon and skin. Fmn is structurally related to the dermatan sulfate/chondroitin sulfate proteoglycans Dcn and Bgn. Fmn binds to collagen and affects the collagen fibrillogenesis in vitro (Heinegard and Oldberg, 1989).

The Fmn protein backbone consists of 357 amino acid residues (42 kDa) which can be divided into three structural domains (Oldberg et al., 1989). The N-terminal domain has four cysteine residues of which two are involved in an intrachain disulfide bond. This region of the protein also contains five to seven closely spaced tyrosine sulfate residues. The central domain, which constitutes 60% of the protein, consists of ten repeats of 25 amino acid residues. This central repeat domain, with preferentially leucine residues in conserved positions, is homologous to similar repeats in a number of proteins including the interstitial proteoglycans Dcn and Bgn (Oldberg et al., 1989). The C-terminal domain contains two cysteine residues which form an intrachain disulfide bond.

Fmn from cartilage, tendon and sclera contains asparagine-linked keratan sulfate chains (Oldberg et al., 1989; Plaas et al., 1990). Four of the five potential N-glycosylation sites in Fmn from bovine articular cartilage is substituted with keratan sulfate chains (Plaas et al., 1990). Fmn binds to type I and II collagen with a $K_d$ of 35 nM. The protein also delays the collagen fibrillation in vitro and causes the formation of thinner fibrils. This collagen binding property is shared by Dcn but not by the structurally related Bgn (Hedbom and HeinegArd, 1989; Brown and Vogel, 1989).

Epiphycan (Epn)

A small dermatan sulfate proteoglycan containing leucine-rich repeats has been isolated from fetal bovine epiphyseal cartilage. This proteoglycan is referred to as Epn based on its preparation from that tissue. This proteoglycan which seems to have restricted expression is closely similar to other leucine-rich repeat containing proteoglycans, Dcn and Bgn (Krusius and Ruoslahti, 1986; Day et al. 1987; Fisher et al., 1989; Neame et al., 1989), as well as to osteoglycin (formerly osteoinductive factor) (Bentz et al., 1990), and is the mammalian equivalent to chick proteoglycan PG-Lβ (Shinomura and Kimata, 1992). Determination of the molecular weight of the intact proteoglycan, the core protein, as well as the glycosaminoglycan (GAG) chains was determined by radiolabeling by either iodination of the protein or tritiation of the GAG chain and subsequent analysis over FPLC chromatography and SDS-PAGE. The molecular weight of the intact proteoglycan was approximately 133 kDa while the core protein was ~46 kDa and the GAG chains were ~23–34 kDa. This analysis was determined in comparison with the fetal bovine epiphyseal Dcn and Bgn produced during the same preparation of Epn. Iodinated proteoglycan was analyzed for its ability to interact with collagens. Furthermore, tryptic peptides from this preparation of Epn were used to determine residues that have undergone posttranslational modification.

Lumican (Lmn)

A recent publication has identified a 1.9-kb cDNA clone encoding the chick Lmn (corneal keratan sulfate proteoglycan) (Blochberger et al., 1992). The CDNA clone contained an open reading frame coding for a 343-amino acid protein, $M_r$=38,640. The deduced sequence shows five potential N-linked glycosylation sites, four of which are in the leucine-rich region. These sites are also potential keratan sulfate attachment sites. The cDNA clone to Lmn hybridized to a 2.0-kb mRNA found in tissues other than cornea, predominantly muscle and intestine. The primary structure of lumican is similar to Fmn, Dcn, and Bgn.

DBP Binding to Dcn Requires Intact Proteoglycan

*B. burgdorferi* has now been found to adhere to Dcn, but does not directly adhere to collagen types I or III. The binding of *B. burgdorferi* to Dcn is specific and appears to require the intact proteoglycan, rather than the isolated core protein or GAG chain. Partial purification of the membrane constituents of *B. burgdorferi* and affinity chromatography using Dcn bound to a solid support has permitted visualization of a DBP having an apparent molecular weight of about 18–20 kDa. However, due to the copurification of the DBP with other *B. burgdorferi* proteins, complete purification of native DBP from borrelias in pure form has not been achieved.

dbp-Encoding Nucleic Acid Segments

As used herein, the term "DBP gene" is used to refer to a gene or DNA coding region that encodes a protein, polypeptide or peptide that is capable of binding Dcn, Fmn, Bgn, Epn, or Lmn.

The definition of a "DBP gene", as used herein, is a gene that hybridizes, under relatively stringent hybridization conditions (see, e.g., Maniatis et al., 1982), to DNA sequences presently known to include DBP gene sequences. It will, of course, be understood that one or more than one genes encoding DBPs or peptides may be used in the methods and compositions of the invention. The nucleic acid compositions and methods disclosed herein may entail the administration of one, two, three, or more, genes or gene segments. The maximum number of genes that may be used is limited only by practical considerations, such as the effort involved in simultaneously preparing a large number of gene constructs or even the possibility of eliciting a significant adverse cytotoxic effect.

In using multiple genes, they may be combined on a single genetic construct under control of one or more promoters, or they may be prepared as separate constructs of the same or different types. Thus, an almost endless combination of different genes and genetic constructs may be employed. Certain gene combinations may be designed to, or their use may otherwise result in, achieving synergistic effects on formation of an immune response, or the development of antibodies to gene products encoded by such nucleic acid segments, or in the production of diagnostic and treatment protocols for borrelia infection, and in particular, infection with *B. burgdorfieri*, *B. afzelii*, or *B. garinii*, and those infections leading to Lyme disease. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g., proteins or polypeptides or various pharmaceutically active agents. So long as genetic material forms part of the composition, there is virtually no limit to other components which may also be included, given that the additional agents do not cause a significant adverse effect upon contact with the target cells or tissues.

Therapeutic and Diagnostic Kits Comprising Dcn Compositions

Therapeutic kits comprising, in suitable container means, a DBP composition of the present invention in a pharmaceutically acceptable formulation represent another aspect of the invention. The DBP composition may be native DBP, truncated DBP, site-specifically mutated DBP, or DBP-encoded peptide epitopes, or alternatively antibodies which bind native DBP, truncated DBP, site-specifically mutated DBP, or DBP-encoded peptide epitopes. In other embodiments, the DBP composition may be nucleic acid segments encoding native DBP, truncated DBP, site-specifically mutated DBP, or DBP-encoded peptide epitopes. Such nucleic acid segments may be DNA or RNA, and may be either native, recombinant, or mutagenized nucleic acid segments.

The kits may comprise a single container means that contains the DBP composition. The container means may, if desired, contain a pharmaceutically acceptable sterile excipient, having associated with it, the DBP composition and, optionally, a detectable label or imaging agent. The formulation may be in the form of a gelatinous composition, e.g., a collagenous-DBP composition, or may even be in a more fluid form that nonetheless forms a gel-like composition upon administration to the body. In these cases, the container means may itself be a syringe, pipette, or other such like apparatus, from which the DBP composition may be applied to a tissue site, skin lesion, wound area, or other site of borrelial infection. However, the single container means may contain a dry, or lyophilized, mixture of a DBP composition, which may or may not require pre-wetting before use.

Alternatively, the kits of the invention may comprise distinct container means for each component. In such cases, one container would contain the DBP composition, either as a sterile DNA solution or in a lyophilized form, and the other container would include the matrix, which may or may not itself be pre-wetted with a sterile solution, or be in a gelatinous, liquid or other syringeable form.

The kits may also comprise a second or third container means for containing a sterile, pharmaceutically acceptable buffer, diluent or solvent. Such a solution may be required to formulate the DBP component into a more suitable form for application to the body, e.g., as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The matrix and gene components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the ultimate matrix-gene composition within the body of an animal. Such an instrument may be a syringe, pipette, forceps, or any such medically approved delivery vehicle.

Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of antibodies from solution wherein the matrix contains DBPs or peptide epitopes derived from DBPs such as those derived from the DBP of *B. burgdorferi*, covalently-coupled to a Sepharose CL6B or CL4B. This matrix binds the antibodies of the present invention directly and allows their separation by elution with an appropriate gradient such as salt, GuHCl, pH, or urea. Another preferred embodiment of the present invention is an affinity chromatography method for the purification of DBPs and peptide epitopes from solution.- The matrix binds the amino acid compositions of the present invention directly, and allows their separation by elution with a suitable buffer as described above.

Methods of Nucleic Acid Delivery and DNA Transfection

In certain embodiments, it is contemplated that the nucleic acid segments disclosed herein will be used to transfect appropriate host cells. Technology for introduction of DNA into cells is well-known to those of skill in the art. Four general methods for delivering a nucleic segment into cells have been described:

(1) chemical methods (Graham and VanDerEb, 1973);
(2) physical methods such as microinjection (Capecchi, 1980), electroporation (Wong and Neumann, 1982; Fromm et al., 1985) and the gene gun (Yang et al., 1990);
(3) viral vectors (Clapp, 1993; Eglitis and Anderson, 1988); and
(4) receptor-mediated mechanisms (Curiel et al., 1991; Wagner et al., 1992).

Liposomes and Nanocapsules

In certain embodiments, the inventors contemplate the use of liposomes and/or nanocapsules for the introduction of particular peptides or nucleic acid segments into host cells. Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977 which describes the use of liposomes and nanocapsules in the targeted antibiotic therapy of intracellular baeterial infections and diseases). Recently, liposomes were developed with improved serum stability and circulation half-times (Gabizon and Papahadjopoulos, 1988; Allen and Choun, 1987).

Nanocapsules can generally entrap compounds in a stable and reproducible way (Henry-Michelland et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1977; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

In addition to the teachings of Couvreur et al. (1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

Methods for Preparing Antibody Compositions

In another aspect, the present invention contemplates an antibody that is immunoreactive with a polypeptide of the invention. As stated above, one of the uses for DBPs and DBP-derived epitopic peptides according to the present invention is to generate antibodies. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. In a preferred embodiment, an antibody is a polyclonal antibody. Means for preparing and characterizing antibodies are well known in the art (See, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for DBP and DBP-derived epitopes may be prepared using conventional immunization techniques, as will be generally known to those of skill in the art. A composition containing antigenic epitopes of particular DBPs can be used to immunize one or more experimental animals, such as a rabbit or mouse, which will then proceed to produce specific antibodies against DBP peptide. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i.e., B-cells of different lineage. mAbs, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

To obtain mAbs, one would also initially immunize an experimental animal, often preferably a mouse, with a DBP-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting mAbs against DBP. Hybridomas which produce mAbs to the selected antigens are identified using standard techniques, such as ELISA and Western blot methods. Hybridoma clones can then be cultured in liquid media and the culture supernatants purified to provide the DBP-specific mAbs.

It is proposed that the mAbs of the present invention will also find useful application in immunochemical procedures, such as ELISA and Western blot methods, as well as other procedures such as immunoprecipitation, immunocytological methods, etc. which may utilize antibodies specific to DBPs. In particular, DBP antibodies may be used in immunoabsorbent protocols to purify native or recombinant DBPs or DBP-derived peptide species or synthetic or natural variants thereof.

The antibodies disclosed herein may be employed in antibody cloning protocols to obtain cDNAs or genes encoding DBPs from other species or organisms, or to identify proteins having significant homology to DBP. They may also be used in inhibition studies to analyze the effects of DBP in cells, tissues, or whole animals. Anti-DBP antibodies will also be useful in immunolocalization studies to analyze the distribution of bacteria expressing DBPs during cellular-infection, for example, to determine the cellular or tissue-specific distribution of borrelias under different physiological conditions. A particularly useful application of such antibodies is in purifying native or recombinant DBPs, for example, using an antibody affinity column. The operation of all such immunological techniques will be known to those of skill in the art in light of the present disclosure.

DBP Compositions for Treating Borrelia Infections

DBP-specific antibody compositions are used to bind to the bacteria and prevent adhesion to host tissues. Moreover, antibody coated bacteria are more easily recognized by the immune system resulting in more efficient killing of the bacteria. Dcn, Lmn, Epn, Fmn, Bgn, etc., or other molecules mimicking specific structure(s) within host tissues that pathogenic bacteria attach, may be used to saturate the DBPs on the surface of the bacteria, thereby preventing adhesion. Alternatively, DBP derivatives, or other molecules mimicking DBP may be used to saturate the binding site within host tissues, resulting in the inhibition of bacterial adhesion. A third alternative provided by the invention is anti-DBP antibody compositions which bind to DBP both in vitro and in vivo. Such antibodies make the DBPs unavailable for attachment to Dcn, and therefore, the bacteria expressing cell surface DBPs are unable to adhere to host tissues via Dcn binding.

Recombinant Expression of DBP

Recombinant clones expressing the dbp nucleic acid segments may be used to prepare purified recombinant DBP (rDBP), purified rDBP-derived peptide antigens as well as mutant or variant recombinant protein species in significant quantities. The selected antigens, and variants thereof, are proposed to have significant utility in diagnosing and treating infections cause by borrelias and in particular, *B. burgdorferi, B. garinii* and *B. afzelii*. For example, it is proposed that rDBPs, peptide variants thereof, and/or antibodies against such rDBPs may also be used in imnmunoassays to detect borrelias or as vaccines or immunotherapeutics to treat borrelia infections, and to prevent bacterial adhesion to ECM components such as Dcn in the same manner as native DBP compositions.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of blocking antibodies which prevent bacterial adhesion to Dcn, as outlined herein.

Antibody Compositions and Formulations Thereof

Means for preparing and characterizing antibodies are well known in the art (See, e.g., Harlow and Lane (1988); incorporated herein by reference). The methods for generating mAbs generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5\times10^7$ to about $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729–6 are all useful in connection with human cell fusions.

One preferred murine myeloma cell is the NS-1 myeloma cell line (also termed P3-NS-1-Ag4–1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1\times10^{-6}$ to about $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific mAb produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

Inmunoassays

As noted, it is proposed that native and synthetically-derived peptides and peptide epitopes of the invention will find utility as inmmunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of DBP-derived proteins and peptides is not limited to such assays, and that other useful embodiments include RIAs and other non-enzyme linked antibody binding assays and procedures.

In preferred ELISA assays, proteins or peptides incorporating DBP, rDBP, or DBP-derived protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween™. These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween™, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween™).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

ELISAs may be used in conjunction with the invention. In one such ELISA assay, proteins or peptides incorporating antigenic sequences of the present invention are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

Immunoprecipitation

The anti-DBP antibodies of the present invention are particularly useful for the isolation of DBP antigens by immunoprecipitation. Immunoprecipitation involves the separation of the target antigen component from a complex mixture, and is used to discriminate or isolate minute amounts of protein. For the isolation of cell-surface localized proteins such as DBP, peptides must be solubilized from the bacterial cell wall by treatment with enzymes such as lysozyme, lysostaphin or mutanolysin, or alternatively, into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

In a related embodiment, antibodies of the present invention are useful for promoting the binding of Dcn to dbp gene products. Such binding is readily measured by monitoring ligand binding using well-known procedures. Detection of the binding may be accomplished by using radioactively labeled antibodies or alternatively, radioactively-labeled Dcn. Alternatively, assays employing biotin-labeled antibodies are also well-known in the art as described (Bayer and Wilchek, 1980).

Western Blots

The compositions of the present invention will find great use in immunoblot or western blot analysis. The anti-DBP antibodies may be used as high-affinity primary reagents for the identification of proteins immobilized onto a solid support matrix, such as nitrocellulose, nylon or combinations thereof. In conjunction with inunnoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods in conjunction with Western blotting (including enzymatically-, radiolabel-, or fluorescently-tagged secondary antibodies against the toxin moiety) are considered to be of particular use in this regard.

Vaccines

The present invention contemplates vaccines for use in both active and passive immunization embodiments. Immunogenic compositions proposed to be suitable for use as a vaccine may be prepared most readily directly from the novel immunogenic proteins and/or peptide epitopes described herein. Preferably the antigenic material is extensively dialyzed to remove undesired small molecular weight molecules and/or lyophilized for more ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

A composition comprising DBP or DBP-derived proteins and/or native or modified epitopic peptides therefrom could also be the basis for human vaccines. The preparation of such compositions that are essentially free from endotoxin can be achieved by following the published methodology, for example, U.S. Pat. No. 4,271,147 (incorporated herein by reference) discloses methods for the preparation of *Neisseria meningitidis* membrane proteins for use in vaccines.

DBP and DBP-derived epitope-based vaccines may be conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered will be readily determinable by the skilled practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol®) used as 0.25% solution, aggregation of the protein in the vaccine by heat treatment with temperatures ranging between about 70° and about 101° C. for 30 second to 2 minute periods respectively. Aggregation by reactivating with pepsin treated F(ab) antibodies to albumin, mixture with bacterial cells such as *C. parvum* or endotoxins or lipopolysaccharide components of gram-negative bacteria, emulsion in physiologically acceptable oil vehicles such as mannide monooleate (Aracel-A™) or emulsion with 20 percent solution of a perfluorocarbon (Fluosol-DA™) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Of course, in light of the new technology on DNA vaccination, it will be understood that virtually all such vaccination regimens will be appropriate for use with DNA vectors and constructs, as described by Ulmer et al. (1993), Tang et al. (1992), Cox et al. (1993), Fynan et al. (1993), Wang et al. (1993) and Whitton et al. (1993), each incorporated herein by reference. In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun could be used to deliver an effectively immunizing amount of DNA to the epidermis (Fynan et al., 1993).

The present invention contemplates vaccines for use in both active and passive immunization embodiments. Immunogenic compositions, proposed to be suitable for use as a vaccine, may be prepared most readily directly from immunogenic peptides prepared in a manner disclosed herein. Preferably the antigenic material is extensively dialyzed to remove undesired small molecular weight molecules and/or lyophilized for more ready formulation into a desired vehicle. The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tables, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharnaceutical-forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "phannaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Screening Assays

Host cells that have been transformed could be used in the screening of natural and artificially derived compounds or mixtures to select those that are capable of complexing with the DBP and DBP-derived proteins of the present invention. This could be useful in the search for compounds that inhibit or otherwise disrupt, or even enhance the ability of the microorganism to bind Dcn. It is contemplated that effective pharmaceutical agents could be developed by identifying compounds that complex with the particular DBP epitopes, including, for example, compounds isolated from natural sources, such as plant, animal and marine sources, and various synthetic compounds. Natural or man-made compounds that may be tested in this manner could also include various minerals and proteins, peptides or antibodies.

Epitopic Core Sequences

The present invention is also directed to protein or peptide compositions, free from total cells and other peptides, which comprise a purified protein or peptide which incorporates an epitope that is immunologically cross-reactive with one or more of the antibodies of the present invention.

As used herein, the term "incorporating an epitope(s) that is immunologically cross-reactive with one or more anti-DBP antibodies" is intended to refer to a peptide or protein antigen which includes a primary, secondary or tertiary structure similar to an epitope located within a DBP polypeptide. The level of similarity will generally be to such a degree that monoclonal or polyclonal antibodies directed against the DBP polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of DBP epitopes such as those derived from dbp or dbp-like gene products and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to DBP and DBP-related sequences, or other domains which bind Dcn or related proteoglycans. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on DBP epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et- al., 1988). Computerize peptide sequence analysis programs (e.g., DNAStar® software, DNAStar, Inc., Madison, Wis.) may also be useful in designing synthetic DBP peptides and peptide analogs in accordance with the present disclosure.

The peptides provided by this invention are ideal targets for use as vaccines or immunoreagents for the treatment of various borrelia-related diseases, and in particular, those caused by species which contain DBP and DBP-encoding genes, and hence those which express either dbp or dbp-like gene product(s) on the cell surface and in turn interact with ECM components such as Dcn to promote bacterial adhesion to host cells. In this regard, particular advantages may be realized through the preparation of synthetic peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

In the case of preventing bacterial adhesion, the preparation of epitopes which produce antibodies which inhibit the interaction of a Dcn-specific gene product and Dcn or proteoglycans which are structurally similar to Dcn such as Lmn, Bgn, Epn, or Fmn is particularly desirable.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the DBP-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between a DBP and any test antigen, one would first label DBP with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to an antibody of the present invention. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody as DBP, for example, will be able to effectively compete for binding to and thus will significantly reduce DBP binding, as evidenced by a reduction in the amount of label detected.

The reactivity of the labeled antigen, e.g., a DBP composition, in the absence of any test antigen would be the control high value. The control low value would be obtained by incubating the labeled antigen with an excess of unlabeled DBP antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

Site-Specific Mutagenesis

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

The PCR™-based strand overlap extension (SOE) (Ho et al., 1989) for site-directed mutagenesis is particularly preferred for site-directed mutagenesis of the nucleic acid compositions of the present invention. The techniques of PCR™ are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into *E. coli* JM101, XL1-Blue™ (Stratagene, LaJolla, Calif.), JM105, or TG1 (Carter et al., 1985) cells. Clones are isolated and the mutations are confirmed by sequencing of the isolated plasmids. Beginning with the native dbp gene sequence, suitable clones and subclones may be made in BG26:pB/2.5(5), from which site-specific mutagenesis may be performed. Alternatively, the use of pET vectors (Novagen, Inc., Madison, Wis.; U.S. Pat. No. 4,952,496, disclosed herein by reference) is contemplated in the recombinant production of DBP and DBP-derived polypeptides.

Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
Adherence of *B. burgdorferi* to Decorin
Materials and Methods
Bacterial Strains and Culture Low-passage (fewer than 10 in vitro passages) *B. burgdorferi* N40 was used for all studies unless specified otherwise. High-passage *B. burgdorferi* B31 (ATCC 35210) has undergone numerous in vitro passages. *B. burgdorferi* was cultured in BSKII medium at 34° C. (Barbour, 1984). Cultures were incubated in a GasPak chamber (BBL, Baltimore, Md. with 3 to 6% $O_2$ until the cells reached the mid-to late-log phase. Cells were harvested by centrifugation at 14, 500×g for 30 min and gently washed in sterile, filtered phosphate-buffered saline (PBS; pH 7.4; 0.137 M NaCl, 3 mM KCl, 4 mM $Na_2HPO_4$, 1 mM $KH_2PO_4$) three times. The spirochetes were resuspended in PBS, and the cell density was adjusted to $10^9$ organisms per ml by use of a reference standard curve relating the $A_{600}$ to the organism number as determined by dark-field microscopy. The spirochetes were stored at 4° C. and retained Dcn-binding activity for up to 1 month.

*Staphylococcus aureus* Phillips (clinical osteomyelitis isolate) and PH100 (collagen adhesion-negative isogenic mutant of strain Phillips) were grown in brain heart fusion broth (Difco Laboratories, Detroit, Mich.) overnight at 37° C. without antibiotics (Patti et al., 1994). The cells were washed and resuspended in PBS.

Labeling of Dcn

Bovine Dcn from fetal skin was purified as described previously (Choi et al, 1989). Dcn was labeled with NHS-LC-Biotin (Pierce, Rockford, Ill.) as described in the manufacturer's directions and stored at −20° C.

Dcn was iodinated by the chloramine T method as described by Hunter (1978). Five microliters (0.5 mCi) of $Na^{125}I$ [Amersham Life Science, Arlington Heights, Ill.) was used to label 100 μg of Dcn in 1 ml of PBS. The specific activity of the radiolabeled proteoglycan was estimated to be approximately $2×10^6$ cpm/μg.

Attachment Assay

Immulon-1® microtiter plate wells (Dynatech Labs, Chantilly, Va.) were coated with Dcn, collagen type I from rat tail (Collaborative Biomedical Products, Bedford, Mass.), or collagen type III from calf skin (Sigma Chemical Co., St. Louis, Mo.). Dcn was dissolved in PBS, and collagens type I and III were dissolved in 20 mM acetic acid and adjusted to a concentration of 1 mg/ml. Two micrograms of each protein in a total volume of 50 μl was incubated in the microtiter plate wells at 4° C. overnight. The wells were decanted and washed with 200 μl of PBS containing 0.1% bovine serum albumin (BSA) three times for 5 min each. Additional protein-binding sites were blocked by incubating the microtiter wells with 100 μl of a 1-mg/ml concentration of BSA in PBS for 2 h. The wells were washed and incubated for 1 h with 25 μl of a suspension containing $10^9$ organisms per ml of PBS-0.1% bovine serum albumin (BSA) three times for 5 min each. Additional protein-binding sites were blocked by incubating the microtiter wells with 100 μl of a 1 mg/ml concentration of BSA in PBS for 2 h. The wells were washed and incubated for 1 h with 25 μl of a suspension containing $10^9$ organisms per ml of PBS-0.1% BSA. After washing the wells to remove unattached bacteria, the wells were incubated for 1 h with 100 μl of a 1:1,000 dilution of anti-*B. burgdorferi* rabbit serum (rabbits were inoculated with $10^8$ organisms of washed *B. burgdorferi* B31 per ml, and serum was collected 3 weeks postinoculation) in PBS-0.1% BSA. This step was omitted when assaying *S. aureus* attachment because protein A on the surface of *S. aureus* binds the secondary antibody directly. The wells were washed and subsequently incubated with100μl of a 1:1,000 dilution of goat anti-rabbit alkaline phosphatase conjugate (Bio-Rad, Hercules, Calif.) in PBS-0.1% BSA for 1 h and then washed and subsequently incubated with 100 μl of a 1-mg/ml concentration of Sigma 104 phosphatase substrate dissolved in 1 M diethanolamine-0.5 mM $MgCl_2$ (pH 9.8) at 37° C. for 30 to 45 min. The $A_{405}$ was determined in a microplate reader (Molecular Devices, Menlo Park, Calif.).

To assay inhibition of attachment, 100-μl suspensions containing $10^9$ organisms of *B. burgdorferi* N40 per ml were preincubated with 2 μg of the potential competitor (or as otherwise stated) for 1 h at room temperature. The potential competitors included Dcn, BSA (The Binding Site, San Diego, Calif., or ICN, Costa Mesa, Calif.), fetuin type IV (Sigma), thyroglobulin type II (Sigma), fibrinogen (KabiVitrium, Stockholm, Sweden), aggrecan (Isolated from bovine cartilage), heparin (Sigma), and chondroitin sulfate type A (from whale and shark cartilage; Sigma). One microliter of 10% BSA was added to obtain a final concentration of 1% BSA. The suspensions were added to protein-coated microtiter wells, and the assay was continued as described above.

Binding Assay

*B. burgdorferi* N40 cells ($1.5×10^8$) were incubated with approximately 50,000 cpm of $^{125}$I-labeled Dcn in a final volume of 0.5 ml of PBS containing 1% BSA for 1 h at room temperature. The reaction was stopped by the addition of 3 ml of PBS containing 1% B A; centrifugation at 6,000×g for 30 min followed. Radiolabeled Dcn associated with the bacterial pellet was quantitated in a Cobra II Auto-Gamma Counter (Packard Instruments, Meriden, CN). Radioactivity recovered in tubes incubated as described above, but without bacteria, was regarded as background and subtracted from the values obtained with bacteria. Time dependence of binding was assayed by incubating *B. burgdorferi* with $^{125}$I-labeled Dcn as described above and stopping the reaction at the specified times.

Inhibition of binding was assayed by preincubating washed *B. burgdorferi* N40 ($10^8$ organisms per ml) with 5 μg of unlabeled competitor for 30 min. Radiolabeled Dcn (50,000 cpm) was added, and the incubation was continued for another 30 min. The reaction was stopped by the addition of 3 ml of PBS containing 1% BSA, and the assay was continued as described above.

SDS-PAGE and Western Blot-Type Assay

Figure 1B:
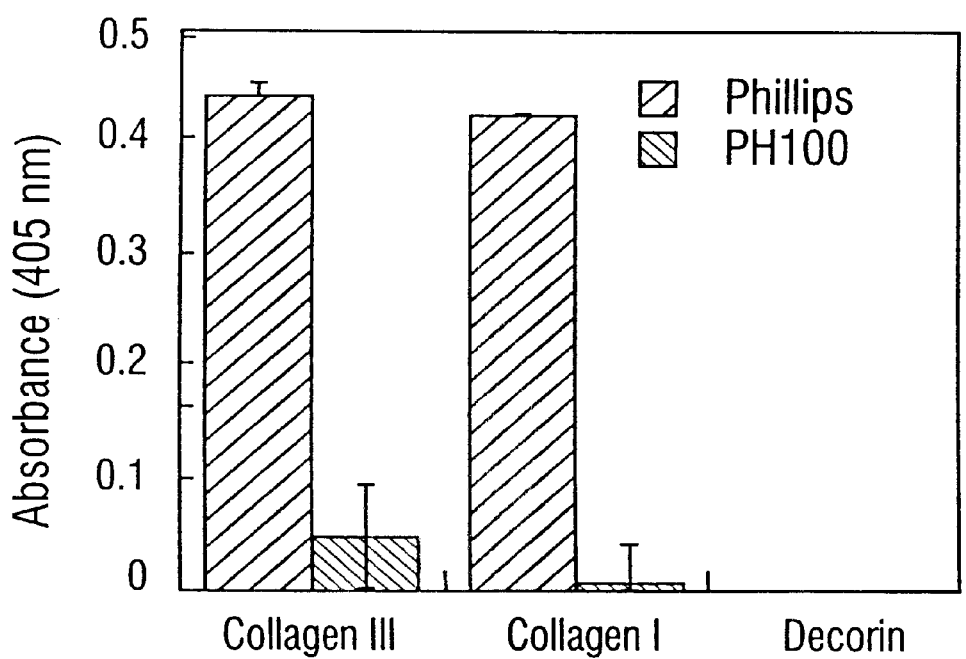
FIG. 1B. Attachment of bacterial strains to microtiter wells coated with type III collagen, type I collagen, or Dcn. Protein-coated microtiter wells were incubated with *S. aureus* Phillips (collagen adhesin positive) or *S. aureus* PH100 (collagen adhesin negative)(B). Attachment to the substrate was quantitated by an ELISA. Error bars represent the standard deviations of three separate determinations.

Proteins from *B. burgdorferi* whole-cell lysates were subjected to sodium dodecyl sulfate-polyacrylamide gel electrophoresis (SDS-PAGE) (Laemmli, 1970) and probed with a Western blot-type assay. For SDS-PAGE, $2×10^7$ *B. burgdorferi* cells were lysed by boiling SDS under reducing conditions and subjected to electrophoresis through a 5 to 15% gradient acrylamide slab gel at 175 V for 30 min. For Western blot-type assays, the proteins were transferred from the polyacrylamide gel to a nitrocellulose membrane (Schleicher & Schuell, Inc., Keene, N.H.) by electroblot for 1.5 h at 4° C. Additional protein-binding sites on the membrane were blocked by incubating in 3% nonfat dry milk in TBST (0.15 M NaCl, 20 mM Tris-HCl, 0.05% Tween 20 [pH 7.4]) for 2 h at room temperature or overnight at 4° C. The membrane was incubated at room temperature with 0.1 μg of biotin-labeled Dcn per ml of TBST for 1 h, washed, and incubated with a 1:3,000 dilution of avidin D horseradish peroxidase conjugate (Vector Laboratories, Burlingame, Calif.) in TBST for 1 h. The membrane was washed and incubated in 1 ml of Enhanced Chemi- Luminescence detection reagents 1 and 2 (Amersham Life Science) for 1 min and exposed to X-ray film for 1 to 5 s.
Results
B. burgdorferi Adheres to Dcn To determine whether any of the major macromolecular components of the dermal collagen fibers (i.e. collagens type I and III and Dcn) can support the adherence of *B. burgdorferi*, the inventors used an in vitro attachment assay. Microtiter wells were coated with Dcn or collagens, and a suspension of spirochetes was incubated for 1 h in the protein-coated wells. Adherent spirochetes were detected by an immunological method after nonadherent organisms were removed by washing. *B. burgdorferi* N40 adhered to wells coated with Dcn (FIG. 1A), whereas spirochete adherence to collagen-coated wells was only marginally greater than adherence to BSA-coated wells. Adherent spirochetes were detected by an immunological method after nonadherent organisms were removed by washing. *B. burgdorferi* N40 adhered to wells coated with Dcn (FIG. 1A and FIG. 1B), whereas spirochete adherence to collagen-coated wells was only marginally greater than adherence to BSA-coated controls wells. Furthermore, in this enzyme-linked immunosorbent assay (ELISA)-type test, the signals from the collagen-coated wells incubated with *B. burgdorferi* were comparable to those from protein-coated wells incubated in the absence of bacteria (FIG. 1A). As a control, the inventors demonstrated (FIG. 1B) that the collagen-coated wells could support adherence of *S. aureus* Phillips, which expresses a collagen adhesin, but could not support adherence of strain PH100, a collagen adhesin-negative mutant. These data demonstrate that *B. burgdorferi* N40 adhered to Dcn but not to the other main components of dermal collagen fibers.

Figure 2:
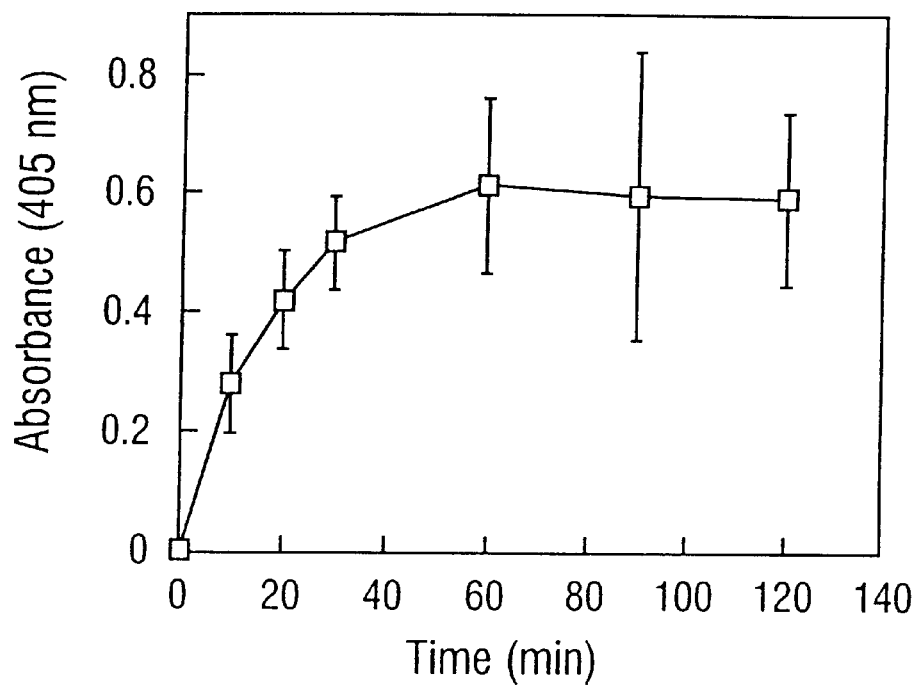
FIG. 2. Time dependence of the attachment of *B. burgdorferi* N40 to Dcn substrata. *B. burgdorferi* was incubated in Dcn-coated microtiter wells for various time intervals. Attachment to the substrate was quantitated by an ELISA. Error bars represent the standard deviations of three separate determinations.

When the adherence of *B. burgdorferi* to Dcn-coated microtiter wells was assayed as a function of time, a time-dependent process in which maximal adherence was reached at ~1 h was observed (FIG. 2). Continuing the incubation for another hour did not result in an increased number of adhering bacteria.

Figure 3:
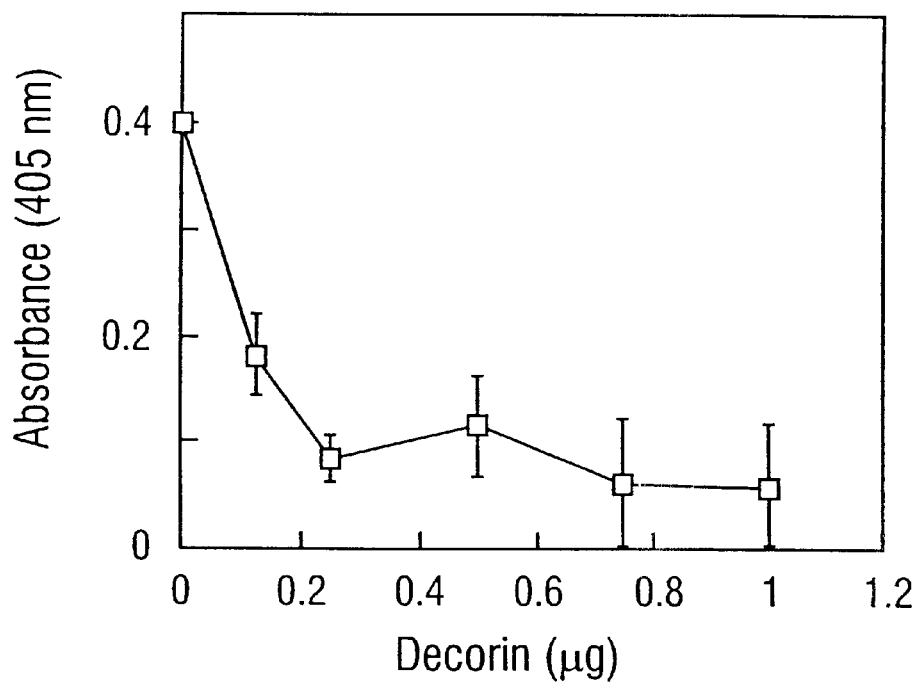
FIG. 3. Inhibition of the attachment of *B. burgdorferi* N40 to Dcn substrata. *B. burgdorferi* was incubated with increasing concentrations of Dcn before being transferred to Dcn-coated microtiter wells. Attachment to the substrate was quantitated by an ELISA. Error bars represent the standard deviations of three separate determinations.

*B. burgdorferi* also appears to recognize soluble Dcn. Preincubation of the spirochetes with increasing concentrations of soluble Dcn resulted in a progressively reduced adherence to the Dcn substrate. A 50% reduction in attachment was observed when $2.5 \times 10^7$ spirochetes were preincubated with 0.1 μg of Dcn (FIG. 3).

Figure 4:
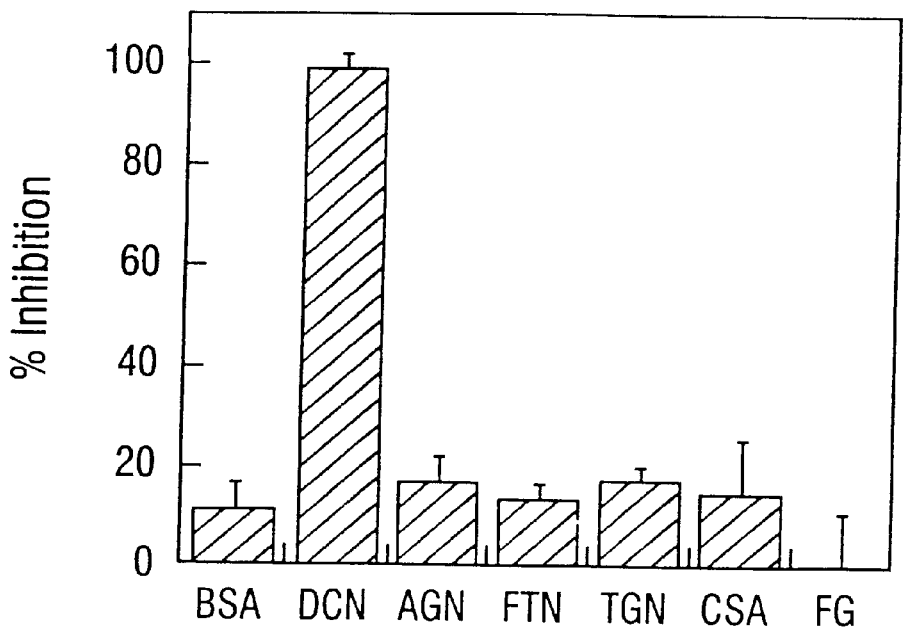
FIG. 4. Specificity of the attachment of *B. burgdorferi* N40 to Dcn substrata. *B. burgdorferi* was incubated with various potential inhibitors before being transferred to Dcn-coated microtiter wells. Potential inhibitors were BSA, Dcn (DCN), aggrecan (AGN), fetuin (FTN), thyroglobulin (TGN), chondroitin sulfate type A (CSA), and fibrinogen (FG). Attachment to the substrate was quantitated by an ELISA. Error bars represent the standard deviations of three separate determinations.

To determine the specificity of *B. burgdorferi* attachment to Dcn-coated wells, the inventors attempted to inhibit such attachment by preincubation of the spirochetes with various soluble extracellular components, such as fetuin, thyroglobulin, fibrinogen, aggrecan, and chondroitin sulfate chains. *B. burgdorferi* was preincubated with each component individually for 1 h, and the suspensions were transferred to microtiter wells whether the spirochetes were allowed to attach to Dcn-coated wells. Dcn inhibited attachment by 100%, whereas the other potential inhibitors only marginally affected attachment of the spirochetes, resulting in less than 20% inhibition (FIG. 4). *B. burgdorferi* attachment to Dcn thus appears to be highly specific.

*B. burgdorferi* Binds Soluble $^{125}$I-labeled Dcn

A modified in vitro binding assay was used to determine whether *B. burgdorferi* binds to soluble $^{125}$I-labeled Dcn. Spirochetes were incubated in a suspension containing PBS, 1% BSA, and $^{125}$I-labeled Dcn. At the end of the incubation, the bacteria were collected by centrifugation and the amount of Dcn bound was assayed by measuring radioactivity in the pellet.

Figure 5:
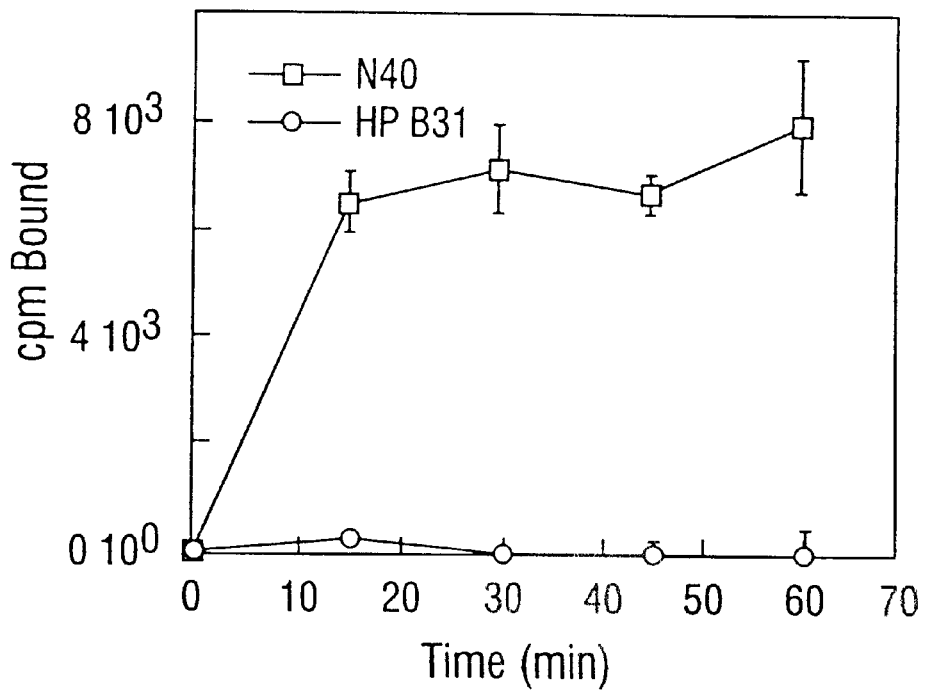
FIG. 5. Time dependence of the binding of *B. burgdorferi* to soluble Dcn. *B. burgdorferi* N40 and HP B31 (high passage) were incubated with Dcn for various time intervals. Binding to Dcn was determined by measuring binding of $^{125}$I-labeled Dcn. Error bars represent the standard deviations of three separate determinations.

When binding was assayed as a function of time from 0 to 120 min, maximum binding was achieved in 15 min and remained constant for up to 2 h (FIG. 5). Prolonged incubation for 3 to 4 h often resulted in a decrease of binding. A high-passage isolate of *B. burgdorferi* B31 showed no binding at any time points (FIG. 5).

Figure 6:
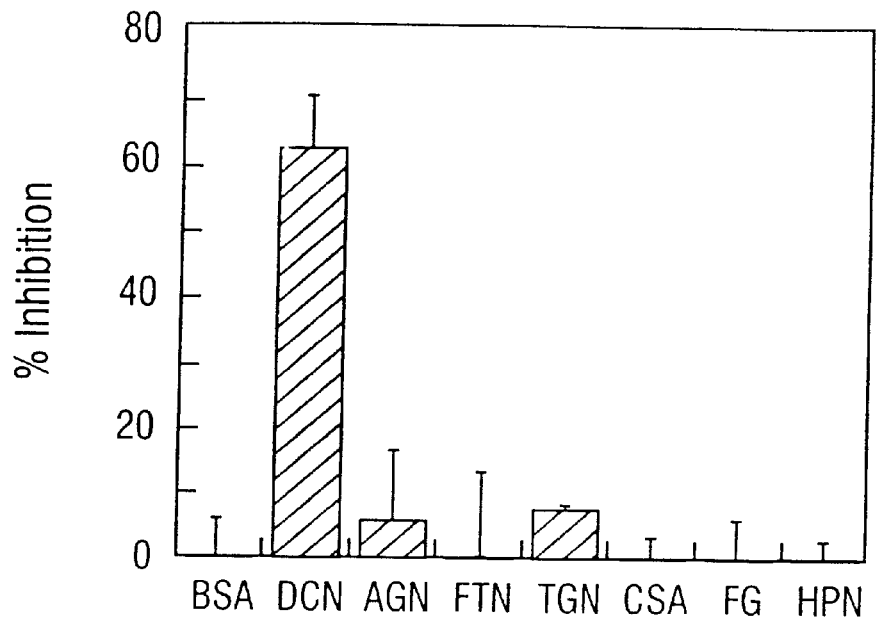
FIG. 6. Specificity of the binding of *B. burgdorferi* N40 to soluble Dcn. *B. burgdorferi* was incubated with various potential inhibitors before being allowed to bind to Dcn. Potential inhibitors were BSA, Dcn (DCN), aggrecan (AGN), fetuin (FTN), thyroglobulin (TGN), chondroitin sulfate type A (CSA), fibrinogen (FG), and heparin (HPN). Binding to Dcn was determined by measuring binding of $^{125}$I-labeled Dcn. Error bars represent the standard deviations of three separate determinations.

To correlate these results with the results of the attachment assay, inhibition of *B. burgdorferi* binding of $^{125}$I-labeled Dcn with different unlabeled components in suspension was attempted. The spirochetes were preincubated with the unlabeled potential competitor for 30 min in the absence of radiolabeled Dcn. After the addition of $^{125}$I-labeled Dcn, the incubation was continued for another 30 min. Dcn inhibited the binding of the radiolabeled ligand by 63%, whereas the other potential inhibitors tested (aggrecan, thyroglobulin, BSA, fetuin, chondroitin sulfate, fibrinogen, and heparin) were essentially without effect, all reducing binding by less than 10% (FIG. 6). Thus, the effect of the unlabeled inhibitors on bacterial binding of soluble $^{125}$I-labeled Dcn is similar to that on the attachment of *B. burgdorferi* to Dcn substrates, indicating that the same bacterial molecule(s) is involved.

Figure 7:
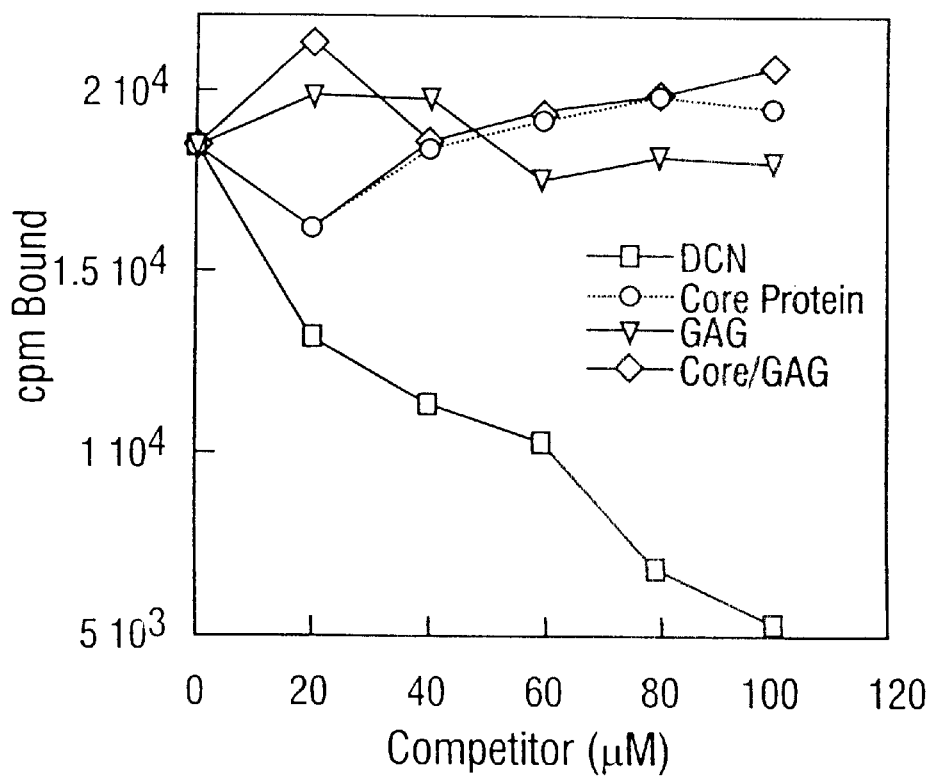
FIG. 7. Involvement of core protein and GAG chain in Dcn binding. *B. burgdorferi* N40 was incubated with unlabeled intact Dcn, isolated core protein, isolated GAG chain, and a mixture of isolated core and GAG before being incubated with radiolabeled intact Dcn. Binding of bacteria to Dcn in the presence of potential inhibitors was quantitated by measuring $^{125}$I-Dcn bound. All datum points were measured in triplicate.

In attempts to determine which domain of Dcn is involved in binding to the spirochete, the inventors attempted to inhibit *B. burgdorferi* binding to intact 125I-labeled Dcn by use of isolated core protein, isolated GAG chain, or an equimolar mixture of both (Bidanset et al., 1992). Binding was inhibited by intact proteoglycan (containing the GAG chain covalently attached to the core protein) but was not inhibited by isolated core protein, isolated GAG chain, or a mixture of both (FIG. 7).

Figure 8:
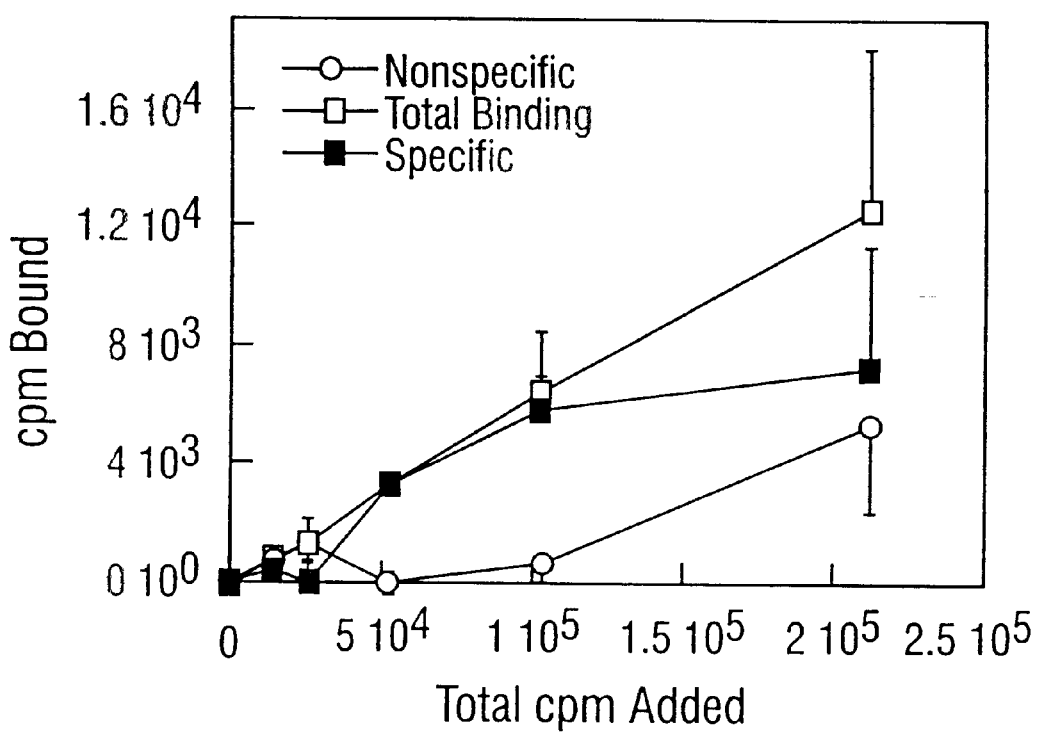
FIG. 8. Saturation of Dcn binding to *B. burgdorferi* N40. *B. burgdorferi* was incubated with increasing concentrations of radiolabeled Dcn in the presence and absence of excess unlabeled Dcn. The binding of *B. burgdorferi* to $^{125}$I-labeled Dcn in the presence (nonspecific binding) and absence (total binding) of excess unlabeled Dcn was measured. Specific binding was calculated by subtracting nonspecific binding from total binding. Error bars represent the standard deviations of three separate determinations.

When *B. burgdorferi* was incubated with increasing amounts of $^{125}$I-labeled Dcn, a concentration-dependent binding of the ligand was observed (FIG. 8). Radioactivity recovered in tubes incubated in the absence of bacteria (nonspecific binding) also increased as the amount of labeled Dcn increased. Specific bacterial binding (total binding minus nonspecific binding) of $^{125}$I-labeled Dcn appeared to approach saturation. From these data, an approximate $K_d$ value was estimated for the interaction as well as the number (n) of Dcn-binding sites per bacteria. $[S]_{bound}/[S]_{free}$ was plotted versus $[S]_{bound}$, where the substrate, S, is Dcn. The $k_d$ was calculated at $3 \times 10^{-7}$ M$^{-1}$, indicating a moderate affinity, and n was calculated to be approximately $5 \times 10^4$ Dcn-binding sites per organism, indicating a small copy number. Although the standard deviation for Dcn bound (FIG. 8) is large, these values are semi-quantitative estimates of $K_d$ and n.

Identification of DBPs from *B. burgdorferi*

Figure 9A:
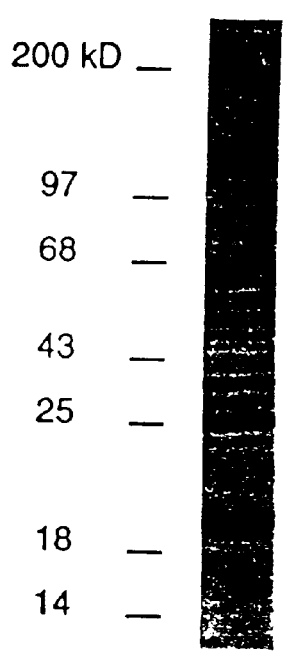
FIG. 9A. Identification of DBPs of *B. burgdorferi* N40. *B. burgdorferi* whole-cell lysate was subjected to SDS-PAGE (5 to 15%) under reducing conditions and stained with Coomassie brilliant blue. The same gel was transferred to a nitrocellulose membrane (FIG. 9B).
Figure 9B:
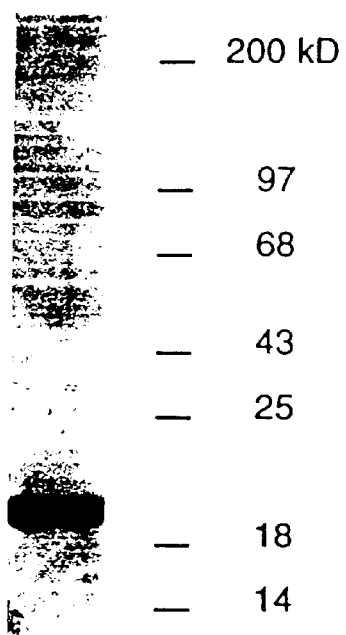
FIG. 9B. Identification of DBPs of *B. burgdorferi* N40. *B. burgdorferi* whole-cell lysate was subjected to SDS-PAGE (5 to 15%) under reducing conditions (FIG. 9A), then transferred to a nitrocellulose membrane. After blocking additional protein-binding sites, proteins on the membrane were probed with biotin-labeled Dcn and visualized by chemiluminescence. The migration of standard proteins with known molecular masses (in kDa) is shown on the left and right.

In an attempt to identify distinct DBPs expressed by *B. burgdorferi*, a Western blot-type assay with biotin-labeled Dcn was used as the probe. Proteins from whole-cell *B. burgdorferi* lysates were separated by SDS-PAGE under reducing conditions and transferred to a nitrocellulose membrane. After blocking additional protein-binding sites with a solution containing 3% nonfat dry milk, biotin-labeled Dcn was allowed to bind to proteins on the membrane, followed by binding of horseradish peroxidase-conjugated avidin to the biotin-labeled Dcn. DBPs were visualized by chemiluminescence. This assay revealed the presence of two DBPs with apparent molecular masses of 19 and 20 kDa in the mixture of proteins from *B. burgdorferi* N40 (FIG. 9A, FIG. 9B). SDS-PAGE followed by staining with Coomassie brilliant blue indicated that these proteins constitute a small portion of the total proteins of *B. burgdorferi*. The two DBPs run directly beneath OspC (the prominent band at ~21 kDa) but are hardly visible, if at all, by Coomassie blue stain. When proteins from the high-passage, non-Dcn-binding B31 strain were analyzed in the same manner, no DBPs could be detected.

The inventors also attempted the inhibition of binding of biotin-labeled Dcn to *B. burgdorferi* proteins in the Western blot-type assay. The membrane was preincubated with the same unlabeled proteins as those used in attempts to block bacterial attachment to Dcn substrate or to inhibit the binding of $^{125}$I-labeled Dcn to intact spirochetes. The same type of specificity was observed in all three assays. Furthermore, the presence of isolated GAG chain or core protein did not interfere with binding of biotin-labeled Dcn to *B. burgdorferi* proteins. Taken together, these data suggest that the 19- and 20-kDa proteins identified as DBPs are responsible for binding of $^{125}$I-labeled Dcn to intact spirochetes and mediate adherence of bacteria to Dcn substrates.

Previous studies have revealed that *B. burgdorferi* is predominantly an extracellular pathogen and that the spirochetes are often found in intimate association with collagen fibers (Barthold el al., 1992; 1993; 1991; Duray, 1992). On the basis of this association, the inventors hypothesized that *B. burgdorferi* may express adhesins that specifically recognize a component of collagen fibers. In the skin, a tissue where *B. burgdorferi* is consistently found, the collagen network is composed mainly of collagen types I and III and the proteoglycan Dcn, which is associated with the collagen fibers.

*B. burgdorferi* adhered to substrata composed of Dcn but did not adhere to collagens type I or III. These data suggest that Dcn is a possible target for *B. burgdorferi* adherence in the skin. Previously, *B. burgdorferi* adherence to heparin Isaacs, 1994) and $α_{IIb}β_3$ integrin (Coburn et al., 1994; 1993) has been reported. Furthermore, heparin inhibits the adherence of *B. burgdorferi* to cultured HeLa cells (Isaacs, 1994) but, as shown in this study, does not affect the binding of Dcn to the spirochete. *B. burgdorferi* most likely possesses several mechanisms of host tissue adherence; however, it is unlikely that any of the previously described adherence mechanisms are responsible for the observed colonization of collagen fibers in the dermis.

*B. burgdorferi* also binds to soluble Dcn in a process that exhibits saturation kinetics and occurs in a time- and concentration-dependent manner. Maximal binding was achieved more quickly when Dcn was in solution than when it was immobilized onto microtiter wells. The reason for this discrepancy is unknown. Both the binding of soluble $^{125}$I-labeled Dcn and the attachment of spirochetes to a Dcn substrate were effectively inhibited by Dcn. Other extracellular matrix proteins had only marginal effects, suggesting a high degree of specificity. Furthermore, neither isolated core protein nor GAG chain alone or in combination could inhibit binding.

The Borrelia binding site on the Dcn molecule has not been identified. Presumably, Dcn binds both collagen and borrelias at once, with the two interactions involving different sites on the proteoglycan. The requirement of intact Dcn adhesin on the spirochete may recognize a conformational motif that is destroyed upon separation of the core protein and the GAG chain.

The $K_d$ for the binding of *B. burgdorferi* to Dcn was estimated to be approximately $3 \times 10^{-7}$ M$^{-i}$, indicating moderate affinity. The number of binding sites, n, was calculated to be approximately $5 \times 10^4$ copies per organism, which is a low copy number. SDS-PAGE analysis also seems to indicate that the DBPs are not abundant *B. burgdorferi* proteins.

By Western blot-type assay, two putative Dcn adhesins with apparent molecular masses of 19 and 20 kDa were identified. The 19-kDa protein may be a truncated product derived from the same gene as the 20-kDa protein; alternatively, the two proteins may be genetically distinct. These data demonstrate that two proteins expressed by *B. burgdorferi* N40 may act as adhesins mediating attachment of spirochetes to dermal collagen via Dcn. Several other *B. burgdorferi* strains, including low-passage Sh-2-82 (Ixodes dammini tick isolate from Shelter Island, N.Y.), B31 (Barbour, 1984), and 297 (Isaacs, 1994), also bind $^{125}$I-labeled Dcn and express a DBP in the 20-kDa molecular mass range.

Example 2
Partial Purification of a Native *B. burgdorferi* DBP

DBP was partially purified by extracting membranes of *B. burgdorferi* strain N-40. To approximately $1 \times 10^9$ organisms/ml phosphate-buffered saline (PBS) was added N-octyl-glucopyranoside to a concentration of 1.5%. The mixture was incubated twenty min at room temperature, rotating end over end. The incubated mixture was spun down at 30,000 rpm for 5 min, and the supernatant containing the extracted membrane constituents was removed. The supernatant was dialyzed against PBS overnight at 4° C., changing the buffer once. The dialyzed membrane supernatant was then filtered thorough a 0.2 μm filter and poured through a Dcn affinity column.

The Dcn affinity column was prepared by first purifying Dcn from fetal bovine skin according to the method described by Choi. Purified Dcn was then covalently linked to CNBr-activated Sepharose® 4B (Pharmacia, Uppsala, SWEDEN), according to the manufacturer's instructions. The 2.0 ml Dcn column was equilibrated with PBS at room temperature, and the membrane preparation was poured through the column, followed by a 10 column volume wash with PBS. Protein bound to the Dcn column was eluted with 1 M NaCl, and eight 0.5 ml fractions were collected.

Twenty microliters of each collected fraction was electrophoresed in duplicate 5–15% gradient SDS polyacrylamide gels. One gel was stained with Coomassie Blue, and showed one major band at about 20 kDa. The second gel was transferred to nitrocellulose and probed with Dcn labeled with NHS-LC-Biotin (Pierce, Rockford, Ill.) according to the manufacturer's instructions. This biotinylated Western blot showed two Dcn-bound bands, one at about 18–19 kDa, and another at about 20 kDa.

A portion of the lower gel band, e.g., the 18–19 kDa band, was cut from the Coomassie Blue stained gel and transferred to a 5–20% gradient polyacrylamide gel together with endopeptidase. The separated proteins were transferred to PVDF (Immunoblon®, Pharinacia), stained with Coomassie Blue and destained in approximately 50% methanol/ 10% acetic acid. The resulting band at approximately 18 kDa was cut from the membrane and sent for commercial sequencing the Baylor College of Medicine Core Protein Facility (Houston, Tex.).

Example 3
Localization of DBP to *B. burgdorferi* Membranes

Figure 13:
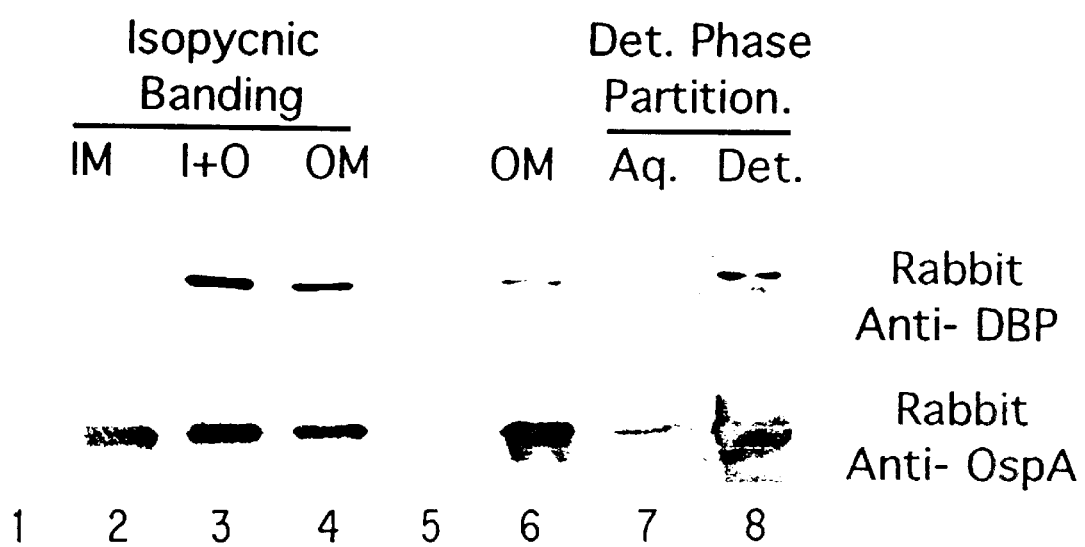
FIG. 13. Membrane localization of candidate borrelia vaccine antigens. *B. burgdorferi*. B31 total membranes were separated into inner- (IM, lane 2) and outer-membranes (OM, lane 4) using published isopycnic centrifugation techniques (Bledsoe et al., 1994). An intermediate density fraction includes both membranes (I+O, lane 3). Outer membranes (lane 6) were further fractionated by Triton X-114® detergent phase partitioning (Brandt et al., 1990) into amphiphilic (Det., lane 8) and hydrophilic (Aq., lane 7) constituents. After resolution by SDS-PAGE and transfer to a nitrocellulose membrane, the localization of DBP in these fractions was determined by immunoblotting with anti-rDBP serum (upper panel, A). As a control the localization of the well-characterized OspA was also determined using anti-OspA serum (lower panel, B). DBP was found predominantly in the OM fraction, unlike OspA which appears here in both membranes as also shown by others (Bledsoe et al., 1994). By detergent phase portioning DBP appears to be amphiphilic as are OspA and other borrelia membrane lipoproteins (Brandt et al., 1990).

The proposed adhesive function of DBP, and its role as a target for growth-inhibitory antibodies, imply that DBP is localized to the borrelia outer membrane. To provide additional biochemical support for this *B. burgdorferi* B3 total membranes were separated into inner and outer membranes (IM, OM) by a recently published isopycnic centrifugation technique (Bledsoe et al., 1994). By detergent phase portioning DBP appears to be amphiphilic (FIG. 13) as are OspA and other borrelia membrane lipoproteins (Brandt et al., 1990). To confirm the presence of lipid on these proteins *B. burgdorferi* B31 was metabolically labeled with $^3$H-palmitate (Brandt et al., 1990), lysed, and used in an immunoprecipitation assay with rabbit anti-rDBP and antirOspA. Both DBP and OspA were found to incorporate $^3$H. Thus DBP is a lipoprotein as predicted by its sequence and membrane fractionation properties.

Example 4
Isolation of a Nucleic Acid Sequence Encoding DBP

The nucleotide sequence encoding DBP was obtained from a λZAP™ expression library prepared from *B. burgdorferi* strain 297. The *B. burgdorferi* DNA expression library was screened with digoxigenin-labeled Dcn to identify clones encoding DBP. Positive clones were sequenced, and an approximate 0.6 kb open reading frame identified. One clone, containing the 2.5 kb insert and the approximately 0.6 kb open reading frame was deposited with the American Type Culture Collection (ATCC) on Apr. 24, 1995, and has the accessio No. ATCC69791. This clone was used to express DBP, and the expressed protein was shown to bind Dcn by affinity chromatography and also by dot blot assay with a labeled Dcn probe. The expressed DBP was also shown to prevent the adherence of *B. burgdorferi* to Dcn.

A λZAPT™ expression library was obtained from Dr. Robin Isaacs of the V.A. Medical Center in Jackson, Miss. The library had been constructed using *B. burgdorferi* strain 297 DNA according to the manufacturer's instructions (Stratagene, La Jolla, Calif.). The library was created from DNA recovered from a *B. burgdorferi* 297 (p3) culture and included genomic and plasmid elements. The DNA was partially digested with Sau3A and partially end-filled to enable ligation into the vector digested with xho1 and partially filled in. The initial library contained about 2.1×10$^5$ clones with greater than 95% recombinants. The average insert size was in the range of 2–4 kb.

The library was plated in six 90-mm plates and plaques were lifted onto HAFT nitrocellulose filters (Millipore, Bedford, Mass.) according to the protocol described by Sambrook et al., (1989). The filters were incubated in TBST (0.15 M NaCl, 0.02 M Tris HCI, 0.05% Tween 20, pH 7.4) containing 3% (w/v) bovine serum albumin (BSA) for 2 hours at room temperature. The filters were washed with TBST three times for 5 min at room temperature. The washed filters were incubated with 1 μg of digoxigenin-labeled Dcn (prepared as described above) per ml of TBST for one h at room temperature, then washed as described above and incubated with 1:1000 anti-digoxigenin-POD Fab fragments in TBST for one h at room temperature. The antibody marker was developed by washing and incubating in chloronapthol solution [30 mg of 4-chloro-1-napthol (Bio-Rad, Hercules, Calif.) in 10 ml of methanol, chilled at −20° C. for ten min then 50 ml TBS (0.15 M NaCl, 0.02 M Tris HCl, pH 7.5) and 100 μl of 30% H$_2$O$_2$ was added] at room temperature for 5–20 min until color development was complete.

Positive plaques were pulled and stored in SM as described (Sambrook et al., 1989). The plaques were screened with digoxigenin-labeled Dcn as described above until a pure plaque was obtained (additional 24 rounds). DNA of the clones expressing DBP was transferred to a pBlueScript® sequencing vector following the manufacturer's instructions enclosed with the λZAPII™ Vector. The DNA insert was sequenced using the dideoxy sequencing method.

The sequence of the 2.5 kb (SEQ ID NO:1) insert is shown in FIG. 10A and FIG. 10B, with the approximate 0.6 kb open reading frame (SEQ ID NO:3) and the deduced amino acid sequence of DBP (SEQ ID NO:2) beginning with the ATG sequence at nucleotide 1471 and ending with the TCG at nucleotide 2031. The amino acid sequence is shown in FIG. 11.

Example 5
Identification of DBPs in borrelia Isolates

One aspect of the present invention, is the identification of borrelias using the DBP compositions disclosed herein as diagnostic indicators of borrelial infection. As shown in Table 2, an assay of DBP in borrelias using Western hybridization analyses, it was possible to identify the presence of DBPs in at least 13 strains of *B. burgdorferi*, 5 strains of *B. garinii*, and at least three strains of *B. afzelii*. These methods represent important diagnostic tools for the identification of bacteria in clinical isolates.

Example 6
Nucleic Acid Sequences Encoding Strain Variants of DBP

Figure 14:
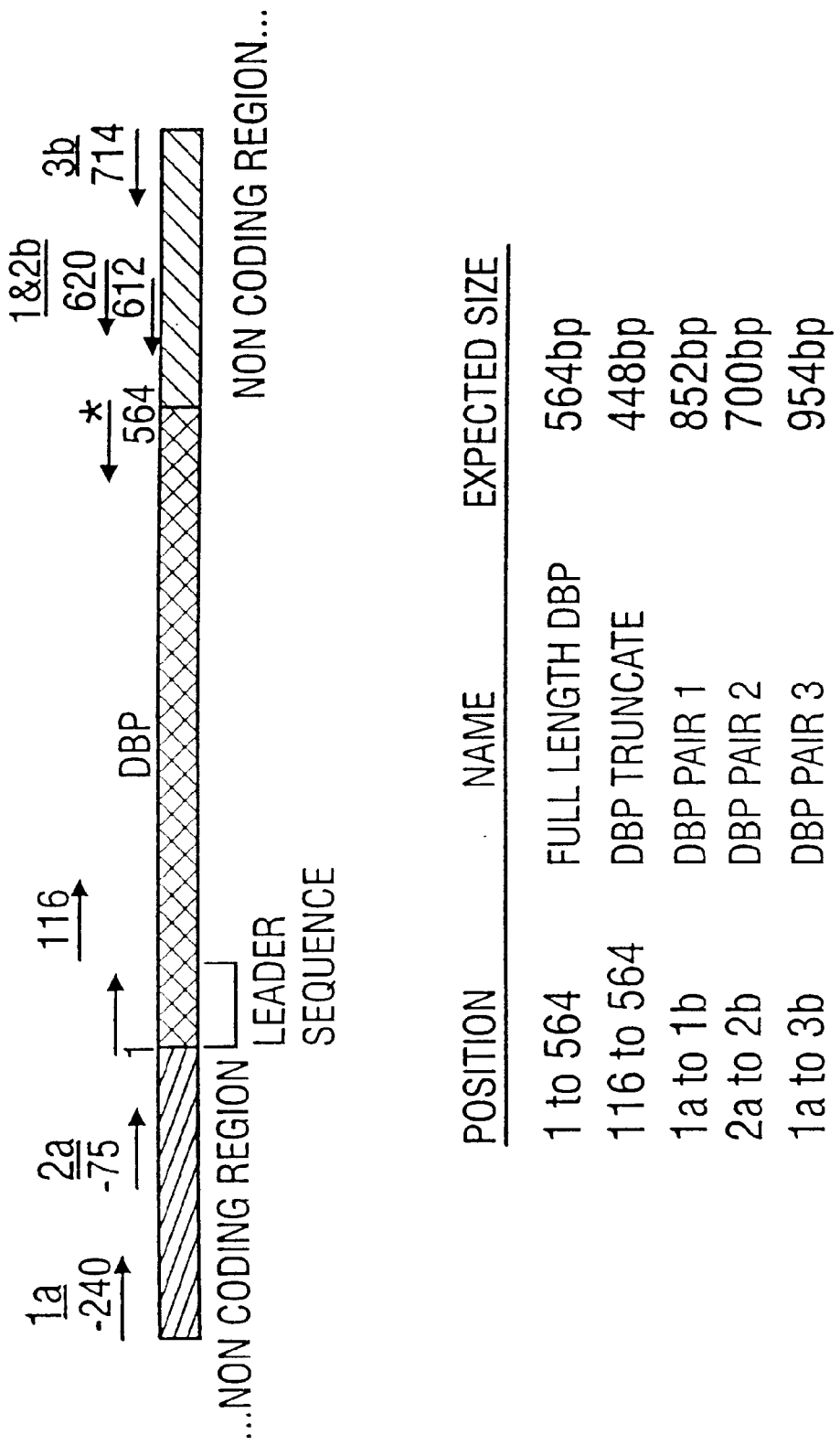
FIG. 14. Diagrammatic representation of oligonucleotide primers for the amplification of dbp genes. Oligonucleotides were designed based on the DNA sequence 5', 3', and within the coding region of the dbp gene (i.e., based on the sequence of BG26:pB/2.5(5). Numbering on the diagram is with respect nucleotide #1 representing the first base of the initiation codon ATG in the dbp gene. Five combinations of these oligonucleotides were used as primer pairs for PCR™ amplification studies with genomic DNA templates from various borrelia strains. The sizes, in base pairs, of the dbp gene segments expected, based on the strain 297 sequence, from these amplification are indicated.

Using the sequence of DBP derived from *B. burgdorferi* strain 297, oligonucleotide amplification primers were constructed to amplify various regions of the gene, as shown in FIG. 14. The primers used are summarized in Table 3.

TABLE 2

Assay of DBP in borrelias By Western Blot

| Strain | Origin | DBP | Source |
|---|---|---|---|
| *B. burgdorferi* | | | |
| N40 | tick | + | S. Norris |
| N40 | tick | + | S. Norris |
| Sh2 | tick | + | S. Norris |
| Sh2 | tick | + | S. Norris |
| B31 | tick | + | S. Norris |
| B31 | tick | −/+ | S. Norris |
| HB19 | blood | − | J. Leong |
| HB19 | blood | − | J. Leong |
| CA3 | tick | + | R. Lane |
| CA7 | tick | + | R. Lane |
| CA8 | tick | + | R. Lane |
| CA20 | tick | + | J. Leong |
| LP4 | skin | + | J. Leong |
| LP5 | skin | + | J. Leong |
| LP7 | skin | + | J. Leong |
| G39/40 | tick | + | J. Leong |
| 297 | CSF | + | R. Isaacs |
| 25015 | tick | + | M. Hanson |
| *B. garinii* | | | |
| PBi | CSF | + | J. Leong |
| PBi | CSF | + | J. Leong |
| G2 | CSF | + | J. Leong |
| PBr | CSF | + | M. Hanson |
| B4-91 | CSF | + | M. Hanson |
| Ip90 | tick | + | M. Hanson |
| *B. afzelii* | | | |
| PKo | skin | + | M. Hanson |
| ACA1 | skin | + | M. Hanson |
| PGau | skin | + | M. Hanson |

TABLE 3

Primers Used in DBP Gene Amplification

| SEQ ID NO: | NAME | PRIMER SEQUENCE |
|---|---|---|
| 4 | BM-1-F | 5'-CGCGGATCCATGATTAAATGTAATAAT-3' |
| 5 | BN-10-F | 5'-CGCGGATCCACCAATCTTCTTAAACTA-3' |
| 6 | BG-26-F | 5'-CGCGGATCCGGACTAACAGGAGCAACA-3' |
| 7 | V-73 RP | 5'-GCGCTGCAGTTATACCCCACTACCCGT-3' |
| 8 | BA-145-F | 5'-CGCGGATCCCGACTTCTCTTAGGAGGT-3' |
| 9 | END-P | 5'-GCGCTGCAGTTACGATTTAGCAGTGCT-3' |

The oligonucleotide primers were used in PCR™ to amplify portions of the DBP from the following strains of *B. burgdorferi*: N40, SH2, HB19, B31 (low passage); HPB31

(high passage), and 297. Amplification was carried out for 30 cycles of 94° C. for one min; 50° C. for 2 min; and 72° C. for three min using standard PCR™ conditions. (100 microliters total volume: 71.5 microliters water; 10 microliters 10×PCR™ buffer; 5 microliters of 5 mM MgCl$_2$; 2 microliters DNA; 2 µl each dNTP; 1.5 microliters of each primers; and 0.5 microliters of Taq Polymerase (GIBCO). Each mixture was covered with 100 microliters of mineral oil and PCR™ cycles begun).

Five primer combinations were tested with each strain of bacteria as described in Table 4.

TABLE 4

PRIMER COMBINATIONS

| → | ← | PROD | N40 | SH2 | B31 | HB19 | HPB31 | 297 |
|---|---|---|---|---|---|---|---|---|
| BM-1F | END-P | 579 bp | − | + | − | − | + | + |
| BN10F | END-P | 549 bp | − | + | + | + | + | + |
| BG26F | V73RP | 159 bp | − | + | − | − | − | + |
| A145F | END-P | 147 bp | − | ND | ND | ND | ND | − |
| BG26F | END-P | 504 bp | + | + | − | + | + | + |

ND = not determined.

The amplification primers derived from the nucleotide sequence of DBP of *B. burgdorferi* strain 297 produced products for each of the variant strains tested, although the ability of specific primers to amplify a product in each strain varied considerably. This implies variation between strains of the bacteria in the nucleic acid sequence encoding DBP.

Using the amplified nucleic acid products described above as hybridization probes, the full length sequences encoding DBP for each strain is isolated. The clones having nucleic acid inserts which hybridize to the above probes are confirmed as encoding DBP by assaying their expressed protein for binding to Dcn, e.g., using the biotinylated Dcn binding assay described.

DBP Compositions Block Adherence of borrelias to Decorin

Microtiter test wells were coated with purified Dcn prepared as described for Example 1 and shaken at 4° C., covered, overnight. (One microgram of Dcn in 50 µl PBS, 50 µl/well.) Control wells were coated with 1% BSA in PBS. Dcn coated wells were also incubated with 1% BSA in PBS for one hour at room temperature to block uncovered sites.

Recombinant DBP was obtained by growing BG26:pB/2.5(5) in LB medium containing 100 µg/ml ampicillin overnight at 37° C. with shaking. 20 ml of the grown bacteria was placed in 1l of LB medium containing 100 µg/ml ampicillin and shaken at 37° C. overnight till reaching an optical density of about 0.6–0.8 at A$_{600}$. IPTG was added to a concentration of 0.2 mM, and the mixture was shaken at 37° C. for about 2–3 hr. The cells were broken in a French press and the debris was pelleted at 40,000 rpm for about 15 min.

The supernatant was filtered through a 0.45 µm filter and 5 µl of the filtered supernatant was added to a 2 ml Dcn affinity column previously equilibrated in PBS. The column was washed with 10 volumes of PBS and the bound protein was eluted with 1 M NaCl. A 5–15% acrylamide gradient gel was prepared, and 20 µl of each fraction was added and the gel run to determine those fractions having the DBP. Those fractions containing the protein were pooled, and the pool dialyzed against PBS overnight at 4° C., changing the buffer at least once. The protein concentration of the dialyzed sample was determined by Lowry assay.

The coated microtiter plate was washed 3 times with 200 µl PBS containing 0.1% BSA, incubating about five min at room temperature on a shaker. DBP was diluted in PBS containing 0.1% BSA. 50 µl of the appropriate dilution was added to the well, and the plate was incubated for about 45 min at room temperature and on a shaker. The liquid was decanted and drained.

*B. burgdorferi* strain N40 was then added to the wells. Twenty five (25) microliters of bacteria (1×10$^9$ organisms/ml) in PBS containing 0.1% BSA was added to each well and incubated 45 min at room temperature. The solution was decanted and drained, and the wells washed three times with PBS containing 0.1% BSA to remove unattached bacteria.

Anti-*B. burgdorferi* rabbit serum (1:1000, 100 µl/well) was added and incubated for one h. (Rabbits were inoculated with 1×10$^8$ organisms per ml of washed *B. burgdorferi* strain B31, and serum was collected 3 weeks post-infection). After washing 3 times in PBS containing 0.1% BSA, the second antibody, 100 µl of 1:1000 goat anti-rabbit alkaline phosphatase conjugate (BioRad, Hercules, Calif.) diluted in PBS containing 0.1% BSA was added and incubated for one h at room temperature. Sigma 104 phosphatase substrate (Sigma), 100 microliters of a 1 mg/ml stock dissolved in 1 M diethanolamine, 0.5 mM MgCI$_2$, pH 9.8, was added and incubated at 37° C. for 30 min. A$_{405}$ was calculated as a measure of binding to Dcn.

The results of the study are shown in Table 5, where the reported A$_{405}$ is the mean of three replicates. DBP was successful in blocking adherence of *B. burgdorferi* microorganisms to Dcn in a dose-dependant manner.

TABLE 5

DBP BLOCKS *B. burgdorferi* ADHESION

| DBP (µg) | + Dcn (A405) | + BSA (A405) |
|---|---|---|
| 0.0 | 0.380 | 0.098 |
| 0.5 | 0.208 | 0.127 |
| 2.5 | 0.119 | 0.165 |
| 5.0 | 0.141 | 0.131 |

Example 7

Inhibitory Activity of anti-rDBP Serum Towards in vitro Growth of Borrelia Strains of Diverse Origin Two other borrelia proteins, OspA and OspB, believed to be surface-exposed have been shown to be targets for bacterial killing by specific antibodies in the absence of complement (Sadziene et al., 1993). Accessibility to bacteriostatic or bactericidal antibodies is one measure of a protein's exposure at the surface of a cell. Rabbit antisera were serially diluted in 96 well plates, 10$^5$ mid-log phase borrelia in BSK II medium were added per well, the mixture was incubated for three days, and cell viability (motility) was assessed microscopically. Growth inhibition activity was detected in anti-rDBP serum to a dilution of ~1:5,000 (Table 6) and in anti-rOspA serum, used as a positive control, to ~1:50,000 for *B. burgdorferi* sensu stricto strains including the homologous strain 297. Borrelia incubated in serum raised against a *Streptococcus pneumoniae* protein, PspA, were fully motile. Significantly, serum raised against DBP from *B. burgdorferi* sensu stricto strain 297 was able to inhibit the growth of many heterologous strains including those of the other major phylogenetic groups of Lyme disease spirochetes (Table 8). It should be noted that even though DBP is much less abundant that OspA on in vitro-grown spirochetes, it is still an effective target for DBP-specific antibodies. If OspA is poorly expressed in vivo DBP may be a relatively more effective target for killing.

Example 8
Recombinant Expression of DBPs Using dbp Constructs

To overexpress the dbp-derived peptides of the present invention, DNA fragments encoding either the native or genetically-modified dbp gene of *B. burgdorferi* or dbp-derived nucleic acid segments encoding either DBP epitopes, truncated DBPs or nucleic acid segments encoding mutated DBPs or DBP-derived epitopes are cloned into appropriate expression vectors. Such vectors may contain a multiple restriction enzyme cloning site that situates the nucleic acid segment of interest such that its expression is controlled from an inducible promoter. Methods for determining orientation of the inserted segment, induction of the promotor, growth conditions, and restriction enzyme analysis, and recovery of the produced protein are well-known to those of skill in the art. Expression and quantitation of the peptides are determinable via standard methods such as SDS-PAGE, Western blot analysis, and protein determination assays.

A particular aspect of the present invention is the production of recombinant proteins in large quantity. Such methods are well-known to those of skill in the art, and have been described in detail hereinabove. In an overall and general sense, the production of a large number of recombinant proteins may be produced in either prokaryotic or eukaryotic cells using various expression systems depending upon the particular construct, and the particular advantages of the various expression systems available for such protein production. Particular aspects of the present invention include the use of the following expression systems:

Recombinant proteins so prepared find utility in the present invention in a variety of embodiments, including compositions for immnunoassay reagents, antigen preparation for generation of immune responses in susceptible animals, vaccine formulations, and substrates for antibody production for use in passive and active immunization methods.

An example of a general procedure useful in the large-scale preparation of recombinant DBPs from a prokaryotic source, the following methods may be employed:

Saturated overnight cultures of *E. coli* JM101 supE, endA, sbcB15, hsd R4, rpsL, thi Δ(lac-proAB) (F'traD36 $proAB^+$ $lacI^q$ ZΔM15), *E. coli* JM105 supE thi Δ(lac-proAB) (F'traD36$proAB^+$ $lacI^q$ ZΔM15), TG1 (supE hsdΔ5 thi $\Delta(lac\text{-}proAB)^+$ ($F^+$traD36proAB $lacI^q$ lacZΔM15)) (Carter et al., 1985), or XL1-Blue cells (Stratagene, La Jolla, Calif.) harboring expression plasmids are diluted 1:50 in Luria Broth (Gibco BRL, Grand Island, N.Y.) supplemented with ampicillin and allowed to grow until the culture reached an $OD_{600}$ of 0.6–0.7. Isopropyl-1-thio-β-D-galactopyranoside (IPTG; Gibco BRL, Grand Island, N.Y.) (final concentration 0.2 mM) is added to the cells and growth continued for another 2.5–5 hr at 37° C. The bacteria are collected by centrifugation and the bacterial pellets are resuspended in phosphate buffered saline (PBS; 10 mM phosphate, 0.14 M NaCl, pH 7.4). The cells are lysed by passage through a French press (SLM Instrument Inc., Urbana, Ill.) twice at 20,000 LB/in. The bacterial lysate is centrifuged at 102,000×g for 10 minutes to remove bacterial debris. The supernatant containing the soluble proteins is filtered through a 0.45 μM membrane (Nalgene, Rochester, N.Y.) and retained for further purification.

The present invention also concerns preparation of truncated DBPs expressed in recombinant systems. One such example is the construction of truncated DBPs which still retain the ability to bind decorin. In a preferred embodiment, a vector was constructed to express proteins as fusions to the leader peptide and posttranslational modification sequence of the major *E. coli* lipoprotein, Lpp. Using the T7 promoter expression vector pET-30b (Novagen, Inc., Madison, Wis.) the NdeI-EcoRI restriction fragment containing the beginning of the translational region expressed from the T7 promoter was replaced with a synthetic sequence expressing the leader peptide of the Lpp protein and a peptide specifying lipoprotein posttranslational modifications generating the new vector pT7Lpp1. A fragment of the dbp gene spanning amino acids Gly26 through Ser187 was amplified by PCR™ with priner-added BamHI and HindIII sites. This fragment encoding a truncated DBP protein was cloned into pT7Lpp1 to generate pMSH24. This plasmid was shown to express truncated DBP as a chimeric lipoprotein when transformed into the *E. coli* host strain BL21(DE3)pLysS. Further, this truncated DBP retained the ability to bind Dcn in the tagged-Dcn blotting assay.

Example 9

Passive Immunization Using DBP Antibodies

The antibody compositions disclosed herein find particular utility in the passive immunization of animals to prevent bacterial adhesion to the ECM component Dcn, and related proteoglycans. Native DBP, truncated DBPs, and site-specifically mutagenized DBP proteins are contemplated to be particularly useful as antigens to immunize animal donors, and particularly mammalian donors such as humans. The immunoglobulin fraction (Ig) from the blood plasma of the donors can be purified and systemically administered to a target population. Those individuals at high risk for developing borrelia infections include, but are limited to, patients in intensive care units, immunocompromised patients, surgery patients, children, and persons in areas having high incidence of ixodid tick infestations such as the northeastern, midwestern, and western pacific United States. Two particular references which describe those at risk from borrelioses include Steere, 1994 and a report by the Centers for Disease Control, 1994.

The anti-DBP Ig produced by immunization with peptides of the present invention find particular utility in several areas:

1) blocking the adhesion of bacteria to Dcn-coated substrata;
2) assisting the immune system in clearance by opsonization; and
3) lysing of bacteria by activation of the classical complement pathway.

Materials and Methods

Low-passage *B. burgdorferi* B3 1, which is infectious for mice, was used to demonstrate passive immunization using antibody compositions disclosed herein. This strain reacts with anti-$rDBP_{297}$ and is killed by these antibodies in vitro. C3H/H3J mice, a widely used strain (Barthold et al., 1993) susceptible to both infection and disease were challenged with an intradermal inoculum of $10^4$ spirochetes (100 $LD_{50}$) and passively immunized just before challenge with rabbit sera against rDBP, rOspA, or rPspA.

At two weeks post-challenge tissue samples (bladder, heart, synovial fluid) are placed in BSKII medium and evidence of borrelial outgrowth from these tissues is assessed microscopically after 2 and 3 wk of in vitro culture. Protection is judged to be complete when no spirochetes are seen upon examination of 10–20 high power fields of samples from all three cultures.

Results

One means of demonstrating that accessibility of DBP to antibodies is not an artifact of in vitro manipulation is to demonstrate passive protection from borrelia challenge with these antibodies. Even though common strains of inbred mice (such as C3H/HeJ, C3H/HeN, and Balb/cByJ, Barthold et al., 1993) may differ in the severity of disease elicited by borrelia, their sensitivities to infectious borrelia strains is more uniform.

Figure 12A:
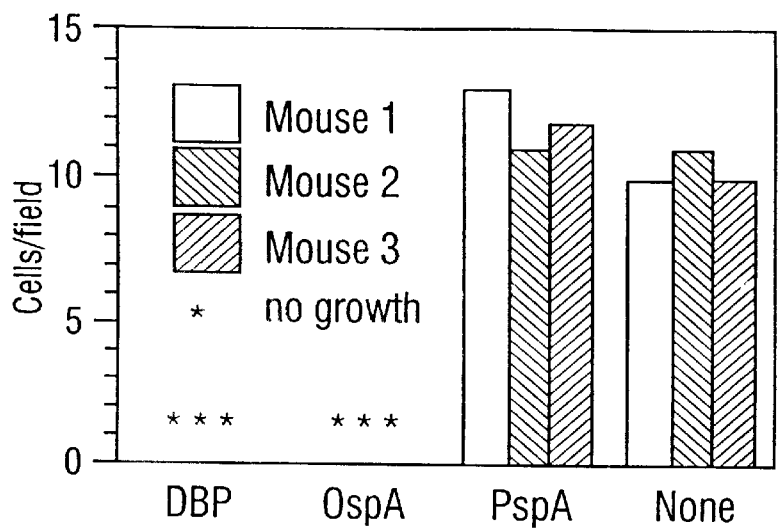
FIG. 12A. Protection of mice from challenge with *B. burgdorferi* by passive administration of anti-DBP serum. Groups of five C3H/HeJ mice were challenged with an intradermal inoculum of $10^4$ *B. burgdorferi* strain B31 (approx. 100 ID$_{50}$) and passively immunized just before challenge with 0.1 ml of rabbit sera against *E. coli* -expressed recombinant PspA (irrelevant streptococcal antigen; neg. control), or no serum. At two weeks post-challenge tissue samples (bladder, FIG. 12A; ear, FIG. 12B; and joint, FIG. 12C) were placed in BSKII medium and evidence of borrelial outgrowth from these tissues was assessed microscopically after 2 wk of in vitro culture at 34° C.; 10–20 high power fields of samples of the cultures were examined before judging tissues to be uninfected. The number of visible borrelia per microscopic field in organ cultures from each mouse are shown. Bladder tissue is a very sensitive indicator of borrelial infection, while joint and skin are also sources of borrelial infection, thus all three tissue samples were routinely assayed. Complete protection was judged when no spirochetes were recoverable from all three tissue sites. Partial or intermediate detection was determined when no borrelias were detectable in joint and skin samples, but a few remaining bacteria were present in bladder tissue.
Figure 12B:
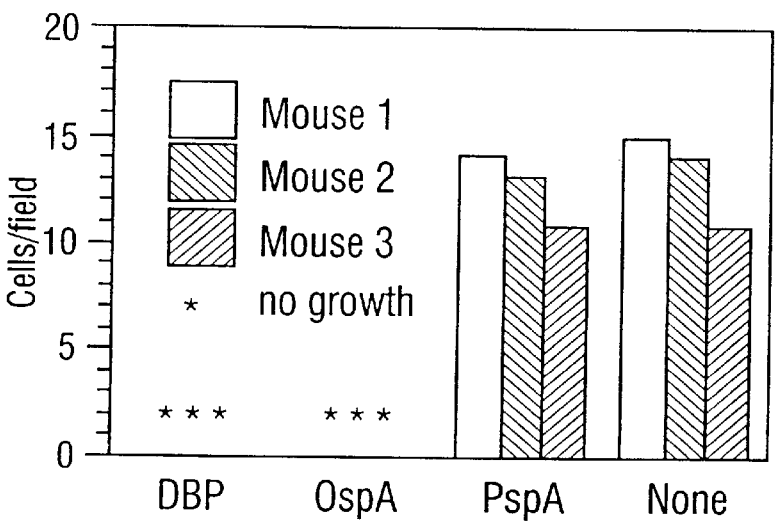
FIG. 12B. Protection of mice from challenge with *B. burgdorferi* by passive administration of anti-DBP serum. Results of study described in legend to FIG. 12A using ear tissue.
Figure 12C:
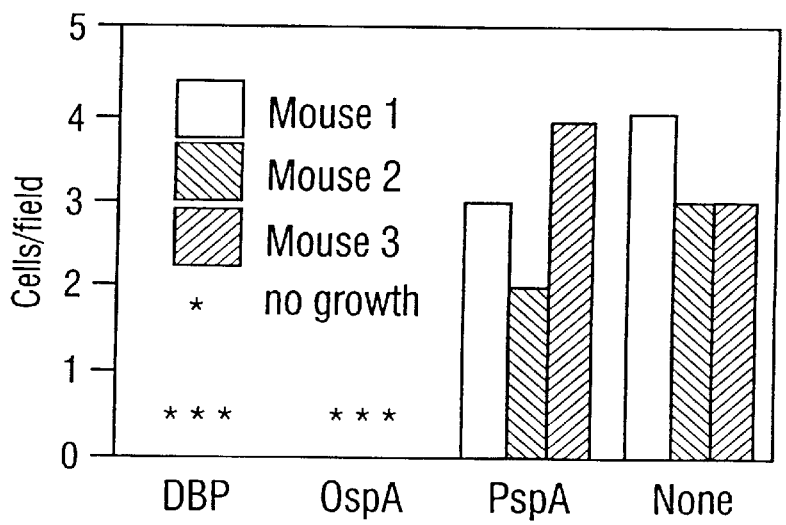
FIG. 12C. Protection of mice from challenge with *B. burgdorferi* by passive administration of anti-DBP serum. Results of study described in legend to FIG. 12A using joint tissue.

As shown in FIG. 12A, FIG. 12B, and FIG. 12C anti-DBP serum confers protection against *B. burgdorferi* B31 even though this is strictly a strain heterologous from the source of antigen, *B. burgdorferi* 297. These results also confirm that DBP remains a target for growth inhibition in vivo, at least for the duration the rabbit antibodies remained in circulation in the test mice.

Example 10

Materials and Methods

Active Immunization Using DBP Compositions

Groups of five mice (Balb/c and C3H/HeJ) were immunized with 20 μg rDBP or soluble protein extract of *E. coli* JM101/pBSII, or 5 μg rOspA lipoprotein in complete Freund's adjuvant (CFA), and boosted with protein in incomplete Freund's adjuvant (IFA) at 4 wk. At two week intervals sera were collected and analyzed for reactivity with the immunizing antigen by ELISA. At the time of challenge these serum ELISA titers were in excess of 1:100,000 indicating all antigen preparations were highly immunogenic by this immunization regimen. Challenge doses and assessment of infection were as described in FIG. 12A, FIG. 12B, and FIG. 12C.

Results

Figure 15A:
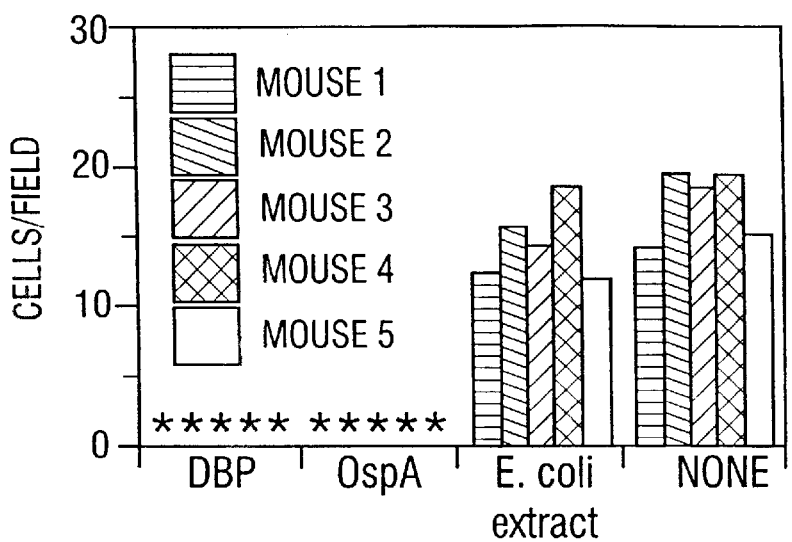
FIG. 15A. Protection of mice from challenge by immunization with rDBP. Balb/c mice were immunized with 20 μg rDBP or soluble protein extract of *E. coli* JM101/pBsII (the host strain for rDBP expression), or 5 μg rOspA lipoprotein incomplete Freund's adjuvant (CFA), and boosted with protein in incomplete Freund's adjuvant (IFA) at 4 wk. Mice were challenged at week 8. Challenge dose and assessment of infection were as described herein. Shown are the results for bladder tissue.
Figure 15B:
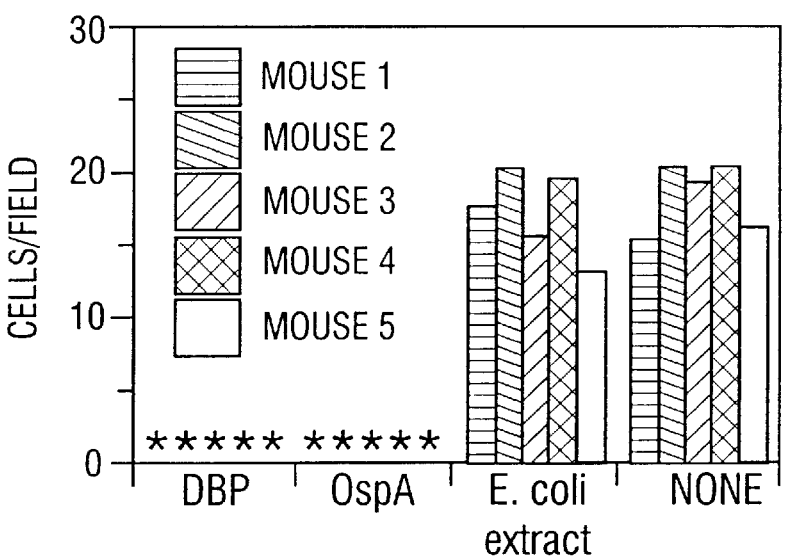
FIG. 15B. Protection of mice from challenge by immunization with rDBP. Balb/c mice were immunized as described in the legend to FIG. 15A. Shown are the results for ear tissue.
Figure 15C:
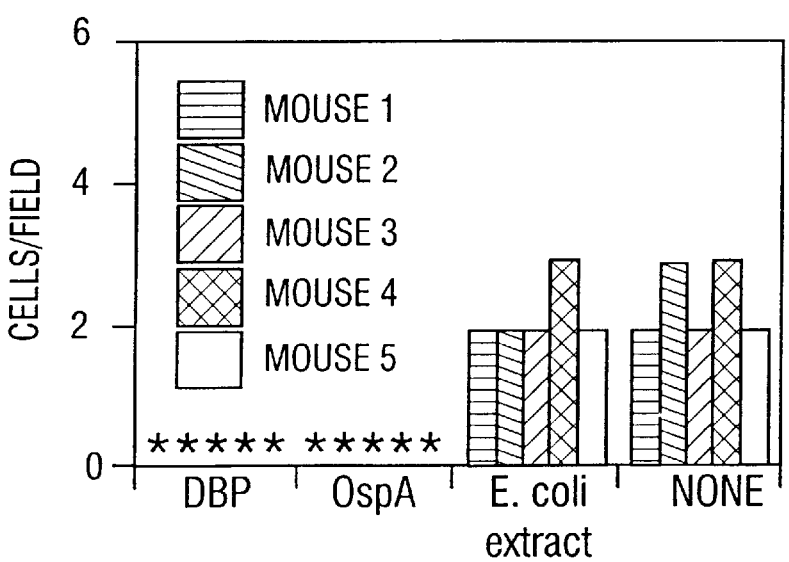
FIG. 15C. Protection of mice from challenge by immunization with rDBP. Balb/c mice were immunized as described in the legend to FIG. 15A. Shown are the results for joint tissue.
Figure 15D:
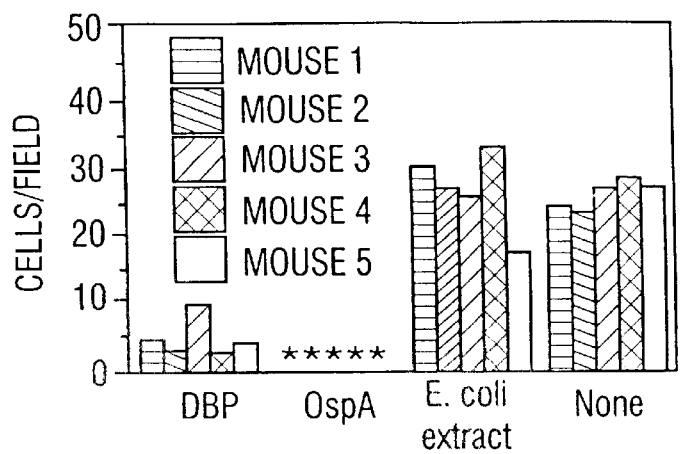
FIG. 15D. Protection of mice from challenge by immunization with rDBP. C3H/HeJ mice were immunized with 20 μg rDBP or soluble protein extract of *E. coli* JM101/pBsII (the host strain for rDBP expression), or 5 μg rOspA lipoprotein incomplete Freund's adjuvant (CFA), and boosted with protein in incomplete Freund's adjuvant (IFA) at 4 wk. Mice were challenged at week 8. Challenge dose and assessment of infection were as described. Shown are the results for bladder tissue.
Figure 15E:
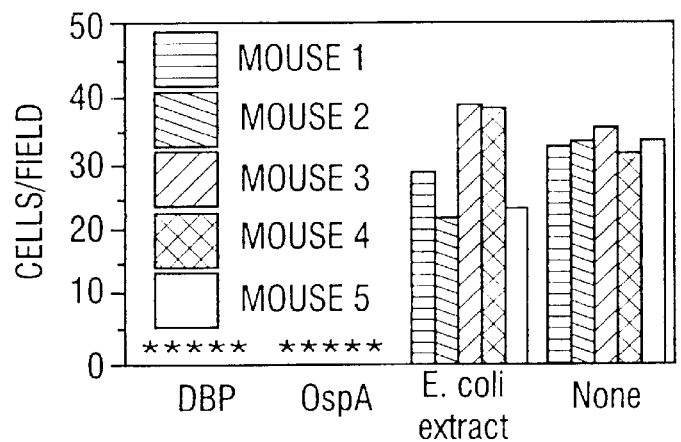
FIG. 15E. Protection of mice from challenge by immunization with rDBP. C3H/HeJ mice were immunized as described in the legend to FIG. 15D Shown are the results for ear tissue.
Figure 15F:
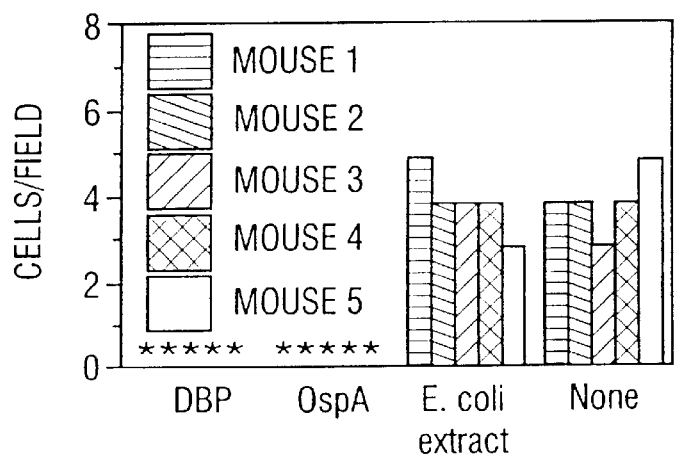
FIG. 15F. Protection of mice from challenge by immunization with rDBP. C3H/HeJ mice were immunized as described in the legend to FIG. 15D. Shown are the results for joint tissue.

The rDBP antigen preparation was able to confer complete protection for Balb/c mice (FIG. 15A, FIG. 15B, and FIG. 15C). Protection was also seen with rOspA, but not with the irrelevant *E. coli* antigen extract. Interestingly, spirochetes were absent form skin and joint tissue of rDBP-immunized C3H (H-$2^k$ haplotype) and Balb/c (H-$2^d$ haplotype) mice in MHC-restricted responses to certain B cell epitopes of rDBP (FIG. 15D, FIG. 15E, and FIG. 15F). It was shown that native DBP is a lipoprotein, and this posttranslational modification, absent on the rDBD antigen preparation used in these studies, may also influence the quality of the immune response. Serum against rDBP raised in rabbits completely protected C3H mice (FIG. 12A, FIG. 12B, and FIG. 12C). Protection against the heterologous B31 strain was seen using rDBP derived from strain 297.

The sensitivity of *B. burgdorferi* to growth in the presence of various antibodies in the absence of complement were assessed using a titration assay performed in microtiter plates (Sadziene et al., 1993) (Table 7). Rabbit antisera were serially diluted in 96-well plates in 0.1 ml BSKII medium, $10^5$ borrelia in the mid-log phase of growth in 0.1 ml BSKII medium were added per well, the mixture was incubated for three days, and cell viability (motility) was assessed by microscopy. The results shown were those using rabbit serum raised against rDBP derived from *B. burgdorferi* sensu stricto strain 297. This serum was strongly inhibitory to growth of all three *B. burgdorferi* sensu stricto strains, as well as several of the *B. garinii* and *B. afzelii* strains. One *B. afzelii* strain, PGau, was slightly inhibited at a 1:50 serum dilution. Strain 25015 was also slightly inhibited by 1:25 anti-DBP serum. The strains inhibited by anti-DBP serum fall into at least four OspA serogroups, and have diverse geographic origins. Serum against an irrelevant antigen, PspA, was not inhibitory. Borrelia strains were obtained from the laboratories of Drs. Steve Norris, John Leong, Alan Barbour, Robert Lane, Robin Isaacs, David Dorward, and Steve Barthold.

Table 8 illustrates that post-infection administration of anti-DBP serum aborts infection. C3H/HeJ mice (three per group) were challenged as above (FIG. 12A, FIG. 12B, and FIG. 12C) given one administration of 0.1 ml serum against OspA, DBP, PspA, or no serum, just prior to challenge (day 0), or at days 2, 4, 7, or 10 post-challenge. Mice were sacrificed at day 17 and infection was assessed as before (FIG. 12A, FIG. 12B, and FIG. 12C). Anti-DBP serum was effective at least out to day four (no spirochetes can be cultured from any organ), while anti-OspA serum was ineffective at day 2, or at later times.

Identification of candidate dbp alleles from *B. burgdorferi, B. afzelii,* and *B. garinii* was accomplished using oligonucleotides diagrammed in FIG. 14 as primers for PCR™ amplifications of dbp gene fragments from borrelia strains representing the three major phylogenetic groups of Lyme disease spirochetes. Portions of the PCR™ amplification reactions were electrophoresed on 1% agarose gels and the approximate sizes of the DNA products were estimated relative to size standards. Where a given primer pair yielded an amplification product of the size expected from the strain 297 sequence this is indicated with a check mark. In some cases additional amplification products were also obtained. All amplifications were initiated with a 15 sec denaturation at 96° C., followed by annealing, then by a 30 sec extension period at 72° C. "Full length" and "truncate" products of the dbp gene with primers within the DBP coding sequence were obtained using a 15 sec annealing period at 42° C. Longer amplification products with primer pairs 1, 2, and 3 outside of the DBP coding sequence were obtained with a 15 sec annealing period at either 45° C. or 49° C. The indicated products were detected after 30 cycles of amplification in the presence of Taq polymerase (Perkin Elmer).

Example 11

Post-Infection Administration of Anti-rDBP Serum Aborts Infection

A major concern for OspA-based vaccines, the leading candidate antigen for a Lyme disease vaccine, is that antibodies against this protein are effective only if present at high levels prior to infection. This suggests that an infection-induced memory response to OspA will be of little or no benefit. However, other borrelia surface proteins required for growth and persistence in vivo may not suffer this limitation as vaccine immunogens. Many bacterial pathogens including borrelias initiate infection following adhesion to specific macromolecules of the host target tissue. These adhesins are exposed at the bacterial surface. Adhesins are effective vaccines against human and animal diseases, as demonstrated in several animal models. Several of the recently developed acellular pertussis vaccines include the *B. pertussis* adhesins pertactin, FHA, and fimbriae (Cherry, 1992). The following example illustrates the effectiveness of DBP in passive immunization studies.

C3H/HeJ mice (three per group) were challenged with an intradermal inoculum of $10^4$ spirochetes (100 $ID_{50}$) and passively immunized with one administration just before challenge with 0.1 ml rabbit sera against rDBP, rOspA, or rPspA (day 0), or at days 2, 4, 7, or 10 post-challenge. Mice were sacrificed at day 17 and infection was assessed by culture of skin, bladder, and joint tissues as before.

As shown in Table 7 anti-DBP serum was effective until day four and beyond, while anti-OspA serum was ineffective after day 2. This shows that DBP, even after a period of four days to grow and adapt to in vivo conditions present in the host remains a target for antibody-mediated elimination. This was not the case for Osp. It is possible this post-infection therapeutic effects can be extended to later in the infection process if multiple doses of antibody, or antibody from the homologous species, are administered to gain more favorable pharmacokinetics. The studies measured only infection rather than disease, however, antibody levels which are not sufficient to eliminate all borrelia may in fact be sufficient to prevent disease pathologies.

Significantly, these results indicate that an infection-induced memory immune response to a priming vaccination with DBP may be effective at eliminating infection or disease.

Example 12

Isolation of Nucleic Acid Sequences Encoding DBPs from *B. burgdorferi*, *B. afzelii*, and *B. garinii*

Oligonucleotides diagrammed in FIG. 14 were used as primers for PCR™ amplifications of dbp gene fragments from borrelia strains representing the three major phylogenetic groups of Lyme disease spirochetes. Primers derived from the dbp gene of strain 297 are able to function in the PCR™ to amplify candidate dbp alleles of the expected size from seven of eight strains tested under a limited set of different amplification conditions. Using a western blot-like assay with tagged Dcn for assessment of Dcn binding activity, all strains shown in Table 8 were found to express a DBP of approximately the same size, 20 kDa+/−2 kDa. Thus these strains were predicted to contain alleles of the dbp gene of strain 297 as confirmed by PCR™. Strains having variant dbp alleles not yet amplified by the conditions described for FIG. 14, such as PBi, may yield detectable PCR™ products under less stringent annealing conditions, or with other combinations of these primers, or both. Determining the nucleotide sequences of these alleles will allow elucidation of the most highly conserved regions which presumably would be common among all genes expressing DBP. These common sequences would then be used to facilitate design of new primers to allow amplification of these strain variants. Alternately, these PCR™ products could be used to identify DNA fragments containing dbp strain variants by Southern hybridization, and ultimately derive molecular clones of these genes.

All mice were challenged s.c. with $10^4$ *B. burgdorferi* B31 (~100 $ID_{50}$ doses) at Day 0. Mice were given a single passive administration (0.1 ml, i.p.) at the time of challenge (Day 0), or at various times afterwards. At Day 17, seven days after the final serum administration, mice were sacrificed, and skin (ear) bladder and joint (tibiotarsal) tissues were placed into culture to assess infection.

TABLE 6

In vitro Growth Inhibitory Activity of Rabbit Anti-rDB$_{297}$ Serum Against Diverse Borrelia Strains

| Strain | Origin | OspA Serogroup[b] | Growth Inhibition by Anti-rDBP$_{297}$ | |
|---|---|---|---|---|
| | | | Growth Inhibition | Titer |
| *D. burgdorferi* | | | | |
| B31 | Tick, USA | 1 | +++ | 5,120 |
| 297 | CSF, USA | 1 | +++ | 5,120 |
| Sh-2 | Tick, USA | 1 | +++ | 5,120 |
| *B. afzelii* | | | | |
| PKo | Skin, Germany | 2 | +++ | 12,800 |
| PGau | Skin, Germany | 2 | +/− | ~1:50[c] |
| ACA I | Skin, Sweden | 2 | − | <1:50[d] |
| *B. garinii* | | | | |
| PBr | CSF, Germany | 3 | +++ | 12,800 |
| PBi | CSF, Germany | 4 | ++ | 800 |
| B4 91 | Skin, Norway | ? | − | <100[d] |
| G2.22 | CSF, Germany | ? | − | <50[d] |
| Ip90 | Tick, Russia | X | − | <50[d] |
| 25015 Group[a] 25015 | Tick, USA | ? | +/− | ~1:25[c] |

[a]Phylogenetically distinct from *B. burgdorferi* sensu stricto: Casjens et al., 1995; Kolbert et al., 1995.
[b]OspA serogroup system of Wilske et al., 1993.
[c]Reduction in spirochete number and motility at lowest serum dilution tested.
[d]No growth inhibition at lowest serum dilution tested.

TABLE 7

Effect of Post-Challenge Passive Administration of Antisera on Borrelia Infection in C3H/HeJ Mice

| | Number of Mice Infected at Each Day of Serum Administration | | | | |
|---|---|---|---|---|---|
| Antiserum | 0 | 2 | 4 | 7 | 10 |
| DBP | 0/3 | 0/3 | 0/3 | 3/3 | 3/3 |
| OspA | 0/3 | 3/3 | 3/3 | — | — |
| PspA | 3/3 | — | — | — | — |
| none | 3/3 | — | — | — | — |

TABLE 8

Amplification of a DBP Allele from Various Borrelia Species

| Species | Strain | Expected DBP Full Length 564 bp | DBP Truncate 448 bp | DBP Pair 1 852 bp | DBP Pair 2 700 bp | DBP Pair 3 954 bp |
|---|---|---|---|---|---|---|
| *B. burgdorferi* | B31 | − | + | − | + | − |
| | 297 | + | + | + | + | + |
| | SH2 | + | + | + | + | + |

TABLE 8-continued

Amplification of a DBP Allele from Various Borrelia Species

| Species | Strain | Expected | DBP Full Length 564 bp | DBP Truncate 448 bp | DBP Pair 1 852 bp | DBP Pair 2 700 bp | DBP Pair 3 954 bp |
|---|---|---|---|---|---|---|---|
| B. afzelli | ACA-1 | | + | − | − | + | − |
| | pGAU | | + | + | − | − | − |
| B. garinii | IP90 | | + | + | − | − | − |
| | B491 | | + | − | − | − | − |
| | pBi | | − | − | − | − | − |

Example 13
Preparation of DBP-Specific Proteoglycan Derivatives

Another aspect of the invention is the preparation of novel compositions comprising proteoglycans and/or their derivatives which recognize the native DBPs and synthetically-modified DBP-derived epitopes disclosed herein. Such compositions are useful in the preparation of therapeutic formulations for preventing bacterial adhesion in an animal, and particularly, in humans. Novel ligands mimicking native Dcn present in the ECM serve as chemopreventatives in bacterial infection by effectively saturating the MSCRAMM components present on the bacterial cell surface.

REFERENCES

The following literature citations as well as those cited above are incorporated in pertinent part by reference herein for the reasons cited in the above text:

U.S. Pat. No. 3,791,932.
U.S. Pat. No. 3,949,064.
U.S. Pat. No. 4,174,384.
U.S. Pat. No. 4,196,265.
U.S. Pat. No. 4,271,147.
U.S. Pat. No. 4,554,101.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 4,683,195.
U.S. Pat. No. 4,683,202.
U.S. Pat. No. 4,952,496.
U.S. Pat. No. 5,168,050.

Abraham et al., "Adherence of *Streptococcus pyogenes, Escherichia coli,* and *Pseudomonas aeruginosa* to Fibronectin-Coated and Uncoated Epithelial Cells," *Infect. Immun.,* 41:1261–1268, 1983.

Allen and Choun, "Large Unilamellar Liposomes with Low Uptake into the Reticuloendothelial System," *FEBS Lett.,* 223:4246, 1987.

Barbour, "Isolation and Cultivation of Lyme Disease Spirochetes," *Yale J. Biol Med.,* 47:521–525, 1984.

Barthold and Bockenstedt, *Infect. Immun.,* 61:4696–4702, 1993.

Barthold et al., "Animal Model: Chronic Lyme borreliosis in the Laboratory Mouse," *Am. J. Pathol.,* 143:959–971, 1993.

Barthold et al., "Kinetics of *Borrelia burgdorferi* Dissemination and Evolution of Disease After Intradermal Inoculation of Mice," *Am. J. Pathol.,* 139:263–273, 1991.

Barthold et al., "Lyme borreliosis in the Laboratory Mouse," *In: Lyme Disease: Molecular and Immunology Approaches,* S. E. Schutzer (ed.), Cold Spring Harbor Press, Plainview, N.Y., p. 223–242, 1992

Barthold et al., *Infect. Immun.,* 63:2255–2261, 1995.

Bayer and Wilchek, "The use of the avidin-biotin complex as a tool for molecular biology" In Glick, D., "Methods of Biochemical Analysis," John Wiley and Sons, New York, 1980.

Bianco et al., *J. Histochem. Cytochem.,* 38:1549–1563, 1990.

Bidanset et al., "Binding of the Proteoglycan Decorin to Collagen Type VI," *J. Biol. Chem.,* 267:5250–5256, 1992.

Bledsoe et al., *J. Bacteriol.,* 176:7447–7455, 1994.

Blockgerger et al., *J. Biol. Chem.,* 267:347–352, 1992.

Bolivar et al., *Gene,* 2:95, 1997.

Bornstein and Sage, *Ann. Rev. Biochem.,* 49:957–1003, 1980.

Brandt et al., *Infect. immun.,* 58:983–991, 1990.

Brown and Vogel, *Matrix,* 9:468–478, 1989.

Campbell, "Monoclonal Antibody Technology, Laboratory Techniques in Biochemistry and Molecular Biology," Bol. 13, Burden and Von Kinippenberg, Eds. pp 75–83, Elsevier, Amsterdam, 1984.

Capecchi, "High efficiency transformation by direct microinjection of DNA into cultured mammalian cells," *Cell,* 22(2):479–488, 1980.

Carter et al,. *Nucl. Acids Res.,* 12:4431–4443, 1985.

Casjens et al,. *J. Bacteriol,* 177:2769, 1995.

Centers for Disease Control, "lyme Disease, United States, 1994," *Morbid. Mortal. W. Rep.,* 44(24):459–463, 1994.

Chang et al., *Nature,* 375:615, 1978.

Cherry, *Vaccine,* 10:1033–1038, 1992.

Choi et al., *J. Biol. Chem.,* 264:2876–2884, 1989.

Choi et al., "Characterization of the Dermatan Sulfate Proteoglycans, DS-PGI and DS-PGII, From Bovine Articular Cartilage and Skin Isolated by Octyl-Sepharose Chromatography," *J. Biol. Chem.,* 264:2876–2884, 1989.

Chopra et al., *Biochem. J.,* 232:277–279, 1985.

Chou and fasman, "Conformational Parameters for Amino Acids in Helical, β-Sheet, and Random Coil Calculated from Proteins," *Biochemistry,* 13(2):211–222, 1974b.

Chou and Fasman, "Empirical Predictions of Protein Conformation," *Ann. Rev. Biochem.,* 47:251–276, 1978b.

Chou and Fasman, "Prediction of β-Turns," *Biophys. J.,* 26:367–384, 1979.

Chou and Fasman, "Prediction of Protein Conformation," *Biochemistry,* 13(2):222–245, 1974a.

Clapp, "Somatic gene therapy into hematopoietic cells. Current status and future implications," *Clin. Perinatol.,* 20(1):155–168, 1993.

Coburn et al., "Diverse Lyme Disease Spirochetes Bind Integrin $\alpha_{IIb}\beta_3$ on Human Platelets," *Infect. Immun.,* 62:5559–5567, 1994.

Coburn et al., "Integrin α$_{IIb}$β$_3$ Mediates Binding of the Lyme Disease Agent *Borrelia burgdorferi* to Human Platelets," *Proc. Natl. Acad. Sci. USA,* 90:7059–7063, 1993.

Couvreur, "Polyalkyleyanoacrylates as Colloidal Drug Carriers," *Crit. Rev. Ther. Drug Carrier Syst.,* 5:1–20, 1988.

Couvreur et al., "Nanocapsules, a New Lysosomotropic Carrier," *FEBS Lett.,* 84:323–326, 1977.

Cox et al., *J. Virol.,* 67(9):5664–5667, 1993.

Curiel et al., "Adenovirus enhancement of transferrin-polylysine-mediated gene delivery," *Proc. NatL. Acad. Sci. USA,* 88(19):8850–8854, 1991.

Day et al., *Biochem. J.,* 248:801–805, 1987.

Dreher et al., *Eur. J. Cell Biol.,* 53:296–304, 1990.

Duray, "Target Organs of *Borrelia burgdorfieri* Infections: Functional Responses and Histology," In: *Lyme Disease: Molecular and Immunologic Approaches,* S. E. Schutzer (ed.), Cold Spring Harbor Press, Plainview, N.Y., p. 11–30, 1992.

Eglitis and Anderson, "Retroviral vectors for introduction of genes into mammalian cells," *Biotechniques,* 6(7):608–614, 1988.

Fiers et al., *Nature,* 273:113, 1978.

Fikrig et al., *J. Exp. Med.,* 181:215–221, 1995.

Fikrig et al., *Science,* 250:553–556, 1990.

Fisher et al., *Connect. Tissue Res.,* 21:43–50, 1989.

Fisher et al., *J. Biol. Chem.,* 258:6588–6594, 1983.

Fisher et al., *J. Biol. Chem.,* 262:9702–9708, 1987.

Fisher et al., *J. Biol. Chem.,* 264:45714576, 1989.

Fröman et al., "Binding of *Escherichia coli* to Fibronectin: A Mechanism of Tissue Adherence," *J. Biol. Chem.,* 259:14899–14905, 1984.

Fromm et al., "Expression of genes transferred into monocot and dicot plant cells by electroporation," *Proc. Natl. Acad. Sci. USA,* 82(17):5824–5828, 1985.

Funderburgh et al., *Dev. Biol.,* 116:267–277, 1986.

Fynan et al., "DNA vaccines: protective immunizations by parenteral, mucosal, and gene gun inoculations," *Proc. Natl. Acad. Sci. USA,* 90(24):11478–11482, 1993.

Gabizon and Papahadjopoulos, "Liposomes formulations with prolonged circulation time in blood and enhanced uptake by tumors," *Proc. Natl. Acad. Sci. USA,* 85:6949–6953, 1988.

Goding, "Monoclonal Antibodies: Principles and Practice," pp. 60–74. 2nd Edition, Academic Press, Orlando, Fla., 1986.

Goeddel et al., *Nature,* 281:544, 1979.

Goeddel et al., *Nucl. Acids Res.,* 8:4057, 1980.

Graham and van der Eb, "Transformation of rat cells by DNA of human adenovirus 5," *Virology,* 54(2):536–539, 1973.

Harlow and Lane, "Antibodies: a Laboratory Manual," Cold Spring Harbor Laboratory, Cold Spring Harbor, N.Y. 1988.

Häupl et al., "Persistence of *Borrelia burgdorferi* in Ligamentous Tissue From a Patient With Chronic Lyme borreliosis," *Arthritis Rheum.,* 36:1621–1626, 1993.

Hedborn and Heinegard, *J. Biol. Chem.,* 264:6898–6905, 1989.

Henry-Michelland et al., "Attachment of Antibiotics to Nanoparticles; Preparation, Drug-Release and Antimicrobial Activity in vitro," *Int. J. Phann.,* 35:121–127, 1987.

Hess et al., *J. Adv. Enzyme Reg.,* 7:149, 1968.

Hitzeman et al., *J. Biol. Chem.,* 255:2073, 1980.

Ho et al., "Site-Directed Mutagenesis by Overlap Extension Using the Polymerase Chain Reaction," *Gene,* 77:51–59, 1989.

Holland et al., *Biochemistry,* 17:4900, 1978.

Hunter, "Radioimmunoassay," In: *Handbook of Experimental Immunology,* D. M. Weir (ed.), Blackwell Scientific Publications, Ltd., Oxford, U.K., p. 14.1–14.40, 1978.

Isaacs, "*Borrelia burgdorferi* Bind to Epithelial Cell Proteoglycans," *J. Clin. Invest.,* 93:809–819, 1994.

Itakura et al., *Science,* 198:1056, 1977.

Jameson and Wolf, *Compu. Appl. Biosci.,* 4(1):181–6, 1988.

Jones, *Genetics,* 85:12 1977.

Keller et al., *J. Am. Med. Assoc.,* 271:1764–1768, 1994.

Kingsman et al., *Gene,* 7:141, 1979.

Kohler and Milstein, *Eur. J. Immunol.,* 6:511–519, 1976.

Kohler and Milstein, *Nature,* 256:495–497, 1975.

Kolbert et al., *Res. Microbiol.,* 146:5, 1995.

Kreis and Vale (eds.), *Guidebook to the Extracellular Matrix and Adhesion Proteins,* A Sambrook and Tooze Publication at Oxford University Press, p. 48–56. 1993.

Krumdieck et al., "The Proteoglycan Decorin Binds Clq and Inhibits the Activity of the Cl Complex," *J. Immunol.,* 149:3695–3701, 1992.

Krusius and Ruoslahti, *Proc. Natl. Acad. Sci. USA,* 83:7683–7687, 1986.

Kuby, "Immunology" 2nd Edition. W. H. Freeman & Company, New York, 1994.

Kyte and Doolittle, *J. Mol. Biol.,* 157(1):105–132, 1982.

Laemmli, "Cleavage of Structural Proteins During the Assembly of the Head of Bacteriophage T4," *Nature (London),* 227:680–685, 1970.

Lovrich et al., *Infect. Immun.,* 63:2113–2119, 1995.

Maloy, et al., "Microbial Genetics" 2nd Edition. Jones and Bartlett Publishers, Boston, Mass., 1994.

Maniatis et al., "Molecular Cloning: a Laboratory Manual," Cold Spring Harbor Laboratory, Cold Spring Harbor, N.Y., 1982.

Maxe et al., "Specific Attachment of *Staphylococcus aureus* to Immobilized Fibronectin," *Infect. Immun.,* 54:695–704, 1986.

McBride et al., *Genomics,* 6:219–225, 1990.

Nakamura et al., "Enzyme Immunoassays: Heterogenous and Homogenous Systems," Chapter 27., 1987.

Neame et al., *J. Biol. Chem.,* 264:8653–8661, 1989.

Oldberg et al., *EMBO J.,* 8:2601–2606, 1989.

Patthy, *J. Mol. Biol.,* 198:567–577, 1987.

Patti et al., "The *Staphylococcus aureus* Collagen Adhesin is a Virulence Determinant in Experimental Septic Arthritis," *Infect. Immun.* 62:152–161, 1994.

Plaas et al., *J. Biol. Chem.,* 265:20634–20640, 1990.

Pringle and Dodd, *J. Histochem. Cytochem.,* 38:1405–1411, 1990.

Probert and LeFebvre, 95th Gen. Mtg. Am. Soc. Microbiol., Abstr. #E-56, 1995.

Prokop and Bajpai, "Recombinant DNA Technology I" *Ann. N.Y. Acad. Sci.,* Vol. 646, 1991.

Ramachandran and Reddi, "Biochemistry of Collagen," Plenum Press, New York, 1976.

Sadziene et al., *J. Infect. Dis.,* 167:165–172, 1993.

Sambrook et al., "Molecular Cloning: A Laboratory Manual," 2nd Edition, Chapter 12.6, Cold Spring Harbor Laboratory, Cold Spring Harbor, N.Y., 1989.

Schaible et al., *Proc. Natl. Acad. Sci. USA,* 87:3768–3772, 1990.

Schaible et al., *Vaccine,* 11:1049–1054, 1993.

Schwan et al., *Proc. Natl. Acad. Sci. USA,* 92:2909–2913, 1995.

Segal, "Biochemical Calculations" 2nd Edition. John Wiley and Sons, New York, 1976.

Steere, *New Engl. J. Med.,* 321:586–596, 1989.

Steere, *Proc. Nat. Acad. Sci. USA.,* 91:2378–2383, 1994.
Stinchcomb et al., *Nature,* 282:39, 1979.
Studier et al., "Use of T7 RNA Polymerase to Direct Expression of Cloned Genes" *Methods Enzymol* 185: , 1990.
Tang et al., *Nature,* 356:152–154, 1992.
Tschemper et al., *Gene,* 10:157, 1980.
Ulmer et al., "Heterologous Protection Against Influenza by Injection of DNA Encoding a Viral Protein," *Science,* 259:1745–1749, 1993.
Urioste et al., *J. Exp. Med.,* 180:1077–1085, 1994.
Van Nhieu et al., "Bacterial Internalization Medicated by $\beta_1$ Chain Integrins is Determined by Ligand Affinity and Receptor Density," *EMBO J.,* 12:1887–1895, 1993.
Vanderrest and Garrone, *FASEB. J.,* 5:2814–2823, 1991.
Vogel and Heinegard, *J. Biol. Chem.,* 260:9298–9306, 1985.
Vogel and Trotter, *Collagen Rel. Res.,* 7:105–114, 1987.
Vogel et al., *Biochem. J.,* 223:587–597, 1984.
Wagner et al., "Coupling of adenovirus to transferrin-polylysine/DNA complexes greatly enhances receptor-mediated gene delivery and expression of transfected genes," *Proc. Natl. Acad. Sci. USA,* 89(13):6099–6103, 1992.
Wang et al., *J. Exp. Med.,* 177:699, 1993.
Wang et al., *J. Immunol.,* 150:3022, 1993.
Whitton et al., *J. Virol.,* 67:(1)348–352, 1993.
Wilske et al., *Infect. Immun.,* 61:2182–2191, 1993.
Wilske et al., *J. Clin. Microbiol.,* 31:340, 1993.
Wilske et al., *Scand. J. Infect. Dis. Suppl.,* 77:108–129, 1991.
Wolf et al., *Compu. Appl. Biosci.,* 4(1):187–91, 1988.
Wong and Neumann, "Electric field mediated gene transfer," *Biochim. Biophys. Res. Commun.* 107(2):584–587, 1982.
Yamaguchi et al., "Negative Regulation of Transforming Growth Factor-$\beta$ by the Proteoglycan Decorin," *Nature (London),* 346:281–284, 1990.
Yang and Russel, *PNAS,* 87:4144–4148, 1990.
Zimmer et al., "Lyme Carditis in Immunodeficient Mice During Experimental Infection of *Borrelia burgdorfeni,*" *Virchows Arch. A Pathol. Anat.,* 417:129–135, 1990.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 2653 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1471..2031

(xi) SEQUENCE DESCRIPTION: SEQ ID NO:1:

```
CTCGATCTAT TTTTTAAATA TAATAAAATT AATAAAAATA AGTGGTAAAA GGAGAAAAGA      60

ATATTTAAAA CAAAATATAT TCTGTTGCCA GTAATAACAT TATTGTGTAA TATGTATAGT     120

GAGGTATTTA CTCAAAGAGC AAGAAACAAA AATCAAAAAA ATCGTTGTTA ACGAACAAAA     180

TGAAAGATTA AAACGCTTAA TAAAAGCTTA TGGAAAAATA CATCTAGTAA AAGTTTAAAA     240

GACATGACAA TTAAAGTAAA AAACAAAATA GCCTCAGGAG CAAGCAAAAA AGGATACTTC     300

TTTAAAGGCC TAAAGGGTAT TTTTATGCCT TTTAAGCCTG CCAATCCTTA TACTCCTAAT     360

TAAAAAAAAT AAAGCAATAT CAAAATAGTC AAAATACTCA AAAGAGAAGC CAATAAATTG     420

CGGGAGATGG CTTCTCTTTT ATTTTTAAGA CCTAATTATT TTAGACTTTG ATTCAATTTG     480

CAAAATAACC AATTTGAAAT ATTTTGGCAA ACTGGAAACA AGTCTTAAAA TACAAGCCAG     540

ATTGATAGAA ACTTGTAATT CCAAACAATG TTACTGCTAT ATTTGCATAA AACAAATTCA     600

CACTAACAAT AAAAATAATA AAATAAAACT TAAACTGATA CGCTTTTAAA ATAAAAGTTT     660

TAAACTTTAG TACAAATCTA GACATTATAT TAACTTTTTA CATCAACATA CTAACTAATT     720

TATTTTATTT TATTTTTCAT AAAGTGGGCT AAAATTTAAA TTTAACTAAA TTTAATAGAA     780

GGAGGAAAAA ATGAAAATTG GAAAGCTAAA TTCAATAGTT ATAGCCTTGT TTTTTAAACT     840

ATTGGTCGCA TGTAGTATTG GATTAGTAGA AAGAACAAAT GCAGCTCTTG AATCGCTCTA     900

AGGATTTAAA AACAAAATTT TAAAAATAAA AAAAGATGCC ACGGGAAAAG GTGTACTTTT     960
```

```
TGAAGCTTTT ACAGGTCTTA AAACCGGTTC CAAGGTAACA AGTGGTGGAC TAGCCTTAAG    1020

AGAAGCAAAA GTACAAGCCA TTGTTGAAAC AGGAAAGTTC CTTAAGATAA TAGAAGAAGA    1080

AGCTTTAAAG CTTAAAGAAA CTGGAAACAG TGGTCAATTC TTGGCTATGT TTGACTTAAT    1140

GCTTGAGGTT GTAGAATCGC TAGAAGACGT TGGAATAATA GGCTTAAAAG CCCGTGTTTT    1200

AGAGGAATCT AAAAATAATC TATAAACACA GCTGAAAGAT TGCTTGCGGC TAAAGCTCAA    1260

ATAGAAAATC AACTTAAAGT GGTTAAGGAA AAACAAAATA TTGAAAATGG TGGAGAGAAA    1320

AAAAATAACA AAAGCAAAAA AAAGAAATAA ATATTAAAAA TATTGTCATT AGAATGGACT    1380

AAAAGTAAAA TTTTTGGCTC GTCCTAATAT TTACAATTTA ATAATATTGG TTTATTGCTT    1440

TTATCTAAAA TACAAAAAAA GGATAATGTT ATG ATT AAA TGT AAT AAT AAA ACT    1494
                                  Met Ile Lys Cys Asn Asn Lys Thr
                                   1               5

TTT AAC AAT TTA CTT AAA CTA ACT ATA CTT GTT AAC CTA CTT ATA TCA    1542
Phe Asn Asn Leu Leu Lys Leu Thr Ile Leu Val Asn Leu Leu Ile Ser
 10              15                  20

TGT GGA CTA ACA GGA GCA ACA AAA ATC AAA TTA GAA TCA TCA GCT AAA    1590
Cys Gly Leu Thr Gly Ala Thr Lys Ile Lys Leu Glu Ser Ser Ala Lys
 25              30                  35                  40

GCC ATT GTA GAT GAA ATA GAT GCA ATT AAA AAA AAG GCT GCT TCT ATG    1638
Ala Ile Val Asp Glu Ile Asp Ala Ile Lys Lys Lys Ala Ala Ser Met
                 45                  50                  55

GGT GTA AAT TTT GAT GCC TTT AAA GAT AAA AAA ACG GGT AGT GGG GTA    1686
Gly Val Asn Phe Asp Ala Phe Lys Asp Lys Lys Thr Gly Ser Gly Val
             60                  65                  70

TCA GAA AAT CCA TTC ATA CTT GAA GCA AAA GTG CGA GCT ACT ACA GTA    1734
Ser Glu Asn Pro Phe Ile Leu Glu Ala Lys Val Arg Ala Thr Thr Val
         75                  80                  85

GCG GAA AAA TTC GTA ATA GCA ATA GAG GAG GAA GCT ACT AAA CTT AAA    1782
Ala Glu Lys Phe Val Ile Ala Ile Glu Glu Glu Ala Thr Lys Leu Lys
     90                  95                 100

GAA ACT GGA AGT AGT GGT GAA TTC TCA GCA ATG TAT GAT TTA ATG TTT    1830
Glu Thr Gly Ser Ser Gly Glu Phe Ser Ala Met Tyr Asp Leu Met Phe
105                 110                 115                 120

GAA GTC TCA AAA CCA TTA CAA GAA TTG GGA ATA CAA GAG ATG ACA AAA    1878
Glu Val Ser Lys Pro Leu Gln Glu Leu Gly Ile Gln Glu Met Thr Lys
                125                 130                 135

ACA GTC TCA ATG GCA GCT GAA GAG AAT CCT CCA ACT ACA GCT CAA GGA    1926
Thr Val Ser Met Ala Ala Glu Glu Asn Pro Pro Thr Thr Ala Gln Gly
            140                 145                 150

GTG CTT GAA ATT GCA AAA AAA ATG AGA GAA AAA TTA CAA AGG GTT CAC    1974
Val Leu Glu Ile Ala Lys Lys Met Arg Glu Lys Leu Gln Arg Val His
        155                 160                 165

AAG AAA AAC CAA GAC ACC TTA AAG AAA AAA AAT ACC GAA GAC AGC ACT    2022
Lys Lys Asn Gln Asp Thr Leu Lys Lys Lys Asn Thr Glu Asp Ser Thr
    170                 175                 180

GCT AAA TCG TAATAAACAC CATTTTTATA TGCAACTCAA AATAATAGAC             2071
Ala Lys Ser
185

CAAACAACCA CCTGTGTTGG GCTGTTTGGT CTTACAATTT AAATGTTAAT TCTGCAATGC    2131

AAAAAACAAA TATTAAGCTC TTCAACCAGC ATTCAAAAGC TAAAATTAAG GTTAAAGCAA    2191

TTAACCCAAA GGATTTAAAA TTTAAAAAAT ACTGTAATAA ACATTAAAAG TTATAAAATG    2251

TAATTATTAT TTTCAAACAA AATAATTAAA TATCCTTTTT GATGTTATTT GGAATTTCTT    2311

TCCTTTAGAC TTTAAATCAA GACTGTCGTA AAGCACCTTA TTATTATCCA TTACAAGAAA    2371
```

```
ATGCACAAAA ACCCGACTTT ACCTTAACTC TGTTATTTCA AACTCTCAGC CAGCTTTAGG    2431

CAAATAAAGT GGACTCTCGT ATCTAACCTT GGAAAATATT TTATAACAAC TAAGAATTTT    2491

ACATGGATTT AAAATATAAC AATCCTTTCT AATGTAGCCT AATTCCAAAA ACCGCTGATA    2551

ATTTAAATTA ACGTCTTTTG CTGTAAAATC AAACCCCTTT AAAACAAATA TCAATAGTGC    2611

AAAGACAAAA AATAACATCG GACTTTTGAA TGTCTTTAAA CA                      2653
```

(2) INFORMATION FOR SEQ ID NO:2:

(i) SEQUENCE CHARACTERISTICS:
        (A) LENGTH: 187 amino acids
        (B) TYPE: amino acid
        (D) TOPOLOGY: linear (xi) SEQUENCE DESCRIPTION: SEQ ID NO:2:

```
Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
                20                  25                  30

Ile Lys Leu Glu Ser Ser Ala Lys Ala Ile Val Asp Glu Ile Asp Ala
            35                  40                  45

Ile Lys Lys Lys Ala Ala Ser Met Gly Val Asn Phe Asp Ala Phe Lys
    50                  55                  60

Asp Lys Lys Thr Gly Ser Gly Val Ser Glu Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser
            180                 185
```

(2) INFORMATION FOR SEQ ID NO:3:

(i) SEQUENCE CHARACTERISTICS:
        (A) LENGTH: 561 base pairs
        (B) TYPE: nucleic acid
        (C) STRANDEDNESS: single
        (D) TOPOLOGY: linear (xi) SEQUENCE DESCRIPTION: SEQ ID NO:3:

```
ATGATTAAAT GTAATAATAA AACTTTTAAC AATTTACTTA AACTAACTAT ACTTGTTAAC     60

CTACTTATAT CATGTGGACT AACAGGAGCA ACAAAAATCA AATTAGAATC ATCAGCTAAA    120

GCCATTGTAG ATGAAATAGA TGCAATTAAA AAAAAGGCTG CTTCTATGGG TGTAAATTTT    180

GATGCCTTTA AAGATAAAAA AACGGGTAGT GGGGTATCAG AAAATCCATT CATACTTGAA    240

GCAAAAGTGC GAGCTACTAC AGTAGCGGAA AAATTCGTAA TAGCAATAGA AGAGGAAGCT    300

ACTAAACTTA AGGAAACTGG AAGTAGTGGT GAATTCTCAG CAATGTATGA TTTAATGTTT    360
```

```
GAAGTCTCAA AACCATTACA AGAATTGGGA ATACAAGAGA TGACAAAAAC AGTCTCAATG      420

GCAGCTGAAG AGAATCCTCC AACTACAGCT CAAGGAGTGC TTGAAATTGC AAAAAAAATG      480

AGAGAAAAAT TACAAAGGGT TCACAAGAAA AACCAAGACA CCTTAAAGAA AAAAAATACC     540

GAAGACAGCA CTGCTAAATC G                                                561
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:4:

```
CGCGGATCCA TGATTAAATG TAATAAT                                          27
```

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:5:

```
CGCGGATCCA CCAATCTTCT TAAACTA                                          27
```

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:6:

```
CGCGGATCCG GACTAACAGG AGCAACA                                          27
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:7:

```
GCGCTGCAGT TATACCCCAC TACCCGT                                          27
```

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:8:

```
CGCGGATCCC GACTTCTCTT AGGAGGT                                          27
```

(2) INFORMATION FOR SEQ ID NO:9:

(i) SEQUENCE CHARACTERISTICS:
        (A) LENGTH: 27 base pairs
        (B) TYPE: nucleic acid -continued

```
        (C) STRANDEDNESS: single
        (D) TOPOLOGY: linear (xi) SEQUENCE DESCRIPTION: SEQ ID NO:9:

GCGCTGCAGT TACGATTTAG CAGTGCT                                          27
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An isolated decorin binding protein or decorin binding peptide that comprises an amino acid sequence of at least about 10 contiguous amino acids from SEQ ID NO:2.

2. The protein or peptide of claim 1, wherein said protein or peptide comprises an amino acid sequence of at least about 15 contiguous amino acids from SEQ ID NO:2.

3. The protein or peptide of claim 2, wherein said protein or peptide comprises an amino acid sequence of at least about 25 contiguous amino acids from SEQ ID NO:2.

4. The protein or peptide of claim 3, wherein said protein or peptide comprises an amino acid sequence of at least about 50 contiguous amino acids from SEQ ID NO:2.

5. The protein or peptide of claim 4, comprising a decorin binding protein that comprises an amino acid sequence of at least about 100 contiguous amino acids from SEQ ID NO:2.

6. The protein or peptide of claim 1, comprising a decorin binding protein that comprises the amino acid sequence of SEQ ID NO:2.

7. The protein or peptide of claim 1, wherein said protein or peptide is isolated from a bacterium.

8. The protein or peptide of claim 7, wherein said protein or peptide is a Borrelia decorin binding protein or peptide.

9. The protein or peptide of claim 8, wherein said protein or peptide is a B. burgdorferi, B. garinii, or B. afzelii decorin binding protein or peptide.

10. The protein or peptide of claim 9, wherein said protein or peptide is a B. burgdorferi decorin binding protein or peptide.

11. The protein or peptide of claim 10, wherein said protein or peptide is a B. burgdorferi strain 297 decorin binding protein or peptide.

12. An isolated bacterial protein having the ability to bind decorin, biglycan, fibromodulin, epiphycan, or lumican, wherein said bacterial protein comprises an amino acid sequence of at least about 10 contiguous amino acids from SEQ ID NO:2.

13. The protein of claim 12, wherein said bacterial protein is a Borrelia bacterial protein.

14. The protein of claim 13, wherein said bacterial protein is a B. burgdorferi, B. garinii, or B. afzelii bacterial protein.

15. A composition comprising an isolated decorin binding protein or decorin binding peptide that includes an amino acid sequence of at least about 10 contiguous amino acids from SEQ ID NO:2.

16. The composition of claim 15, comprising a decorin binding protein or peptide that includes an amino acid sequence of between about 15 and about 187 contiguous amino acids from SEQ ID NO:2.

17. The composition of claim 16, comprising a decorin binding protein or peptide that includes an amino acid sequence of between about 15 and about 150 contiguous amino acids from SEQ ID NO:2.

18. The composition of claim 17, comprising a decorin binding protein or peptide that includes an amino acid sequence of between about 15 and about 100 contiguous amino acids from SEQ ID NO:2.

19. The composition of claim 18, comprising a decorin binding peptide that includes an amino acid sequence of between about 15 and about 50 contiguous amino acids from SEQ ID NO:2.

20. The composition of claim 15, comprising a decorin binding protein or peptide of between about 50 and about 150 amino acids in length.

21. The composition of claim 15, comprising a decorin binding peptide of between about 15 and about 50 amino acids in length.

22. The composition of claim 15, comprising a decorin binding protein of between about 150 and about 187 amino acids in length.

23. The composition of claim 15, wherein said decorin binding protein or peptide is a recombinant protein or peptide.

24. The composition of claim 15, further comprising a pharmaceutically-acceptable excipient.

\* \* \* \* \*